US009345429B2

(12) United States Patent
Suzuki et al.

(10) Patent No.: US 9,345,429 B2
(45) Date of Patent: May 24, 2016

(54) IMAGE PROCESSING DEVICE, IMAGE PROCESSING SYSTEM, IMAGE PROCESSING METHOD, AND PROGRAM

(71) Applicant: Sony Corporation, Tokyo (JP)

(72) Inventors: Masaru Suzuki, Tokyo (JP); Shinichiro Gomi, Tokyo (JP)

(73) Assignee: Sony Corporation (JP)

( * ) Notice: Subject to any disclaimer, the term of this patent is extended or adjusted under 35 U.S.C. 154(b) by 17 days.

(21) Appl. No.: 14/366,540

(22) PCT Filed: Dec. 13, 2012

(86) PCT No.: PCT/JP2012/082374
§ 371 (c)(1),
(2) Date: Jun. 18, 2014

(87) PCT Pub. No.: WO2013/099628
PCT Pub. Date: Jul. 4, 2013

(65) Prior Publication Data
US 2015/0125030 A1  May 7, 2015

(30) Foreign Application Priority Data

Dec. 27, 2011  (JP) ................................. 2011-285560

(51) Int. Cl.
*G06K 9/00* (2006.01)
*G06K 9/46* (2006.01)
(Continued)

(52) U.S. Cl.
CPC ............ *A61B 5/441* (2013.01); *G06K 9/00362* (2013.01); *G06T 5/005* (2013.01); *G06T 7/0081* (2013.01); *A61B 2576/02* (2013.01)

(58) Field of Classification Search
CPC . A61B 5/441; A61B 2576/02; G06K 9/00362
USPC ............................ 382/103, 190, 276, 293, 294
See application file for complete search history.

(56) References Cited

U.S. PATENT DOCUMENTS 6,208,749 B1 * 3/2001 Gutkowicz-Krusin ... A61B 5/442
356/303
6,711,286 B1 * 3/2004 Chen ...................... G06K 9/346
358/515
(Continued)

FOREIGN PATENT DOCUMENTS

JP           2993611 B2    12/1999
JP       2001-283204 A    10/2001
(Continued)

OTHER PUBLICATIONS

International Search Report from International Publication PCT/JP2012/082374 mailed Mar. 12, 2013.

*Primary Examiner* — John Strege
(74) *Attorney, Agent, or Firm* — Lerner, David, Littenberg, Krumholz & Mentlik, LLP

(57) ABSTRACT

The present technique relates to an image processing device, an image processing system, an image processing method, and a program that enable simple and accurate detection of regions showing a detection object such as a body hair in images.
A body hair region detection unit includes: a projective transform unit that generates a projected image by projectively transforming a first image generated by photographing a body hair into the coordinate system of a second image generated by photographing the body hair from a different direction from the first image; a difference image generation unit that generates a difference image between the second image and the projected image; and a region detection unit that detects a candidate region formed with pixels having difference values equal to or larger than a predetermined threshold value in the difference image, and divides the region corresponding to the candidate region in the second image into a body hair region showing the body hair and a non-body-hair region outside the body hair region. The present technique can be applied to devices that analyze skin conditions, for example.

20 Claims, 42 Drawing Sheets

(51) Int. Cl.
　　*G06K 9/66* (2006.01)
　　*A61B 5/00* (2006.01)
　　*G06T 5/00* (2006.01)
　　*G06T 7/00* (2006.01)

(56) References Cited

U.S. PATENT DOCUMENTS

| | | |
|---|---|---|
| 6,963,661 B1 | 11/2005 | Hattori et al. |
| 7,362,881 B2 | 4/2008 | Hattori et al. |
| 7,706,572 B2 | 4/2010 | Hattori et al. |
| 8,331,653 B2 | 12/2012 | Seki et al. |
| 2005/0196034 A1* | 9/2005 | Hattori et al. ............ 382/154 |
| 2006/0269111 A1* | 11/2006 | Stoecker ............ G06F 19/321 382/128 |
| 2010/0103175 A1 | 4/2010 | Okutomi et al. |

FOREIGN PATENT DOCUMENTS

| | | |
|---|---|---|
| JP | 2005-084012 A | 3/2005 |
| JP | 2006-053756 A | 2/2006 |
| JP | 2010-082245 A | 4/2010 |
| WO | 2008-050904 A1 | 5/2008 |

* cited by examiner

FIG. 37
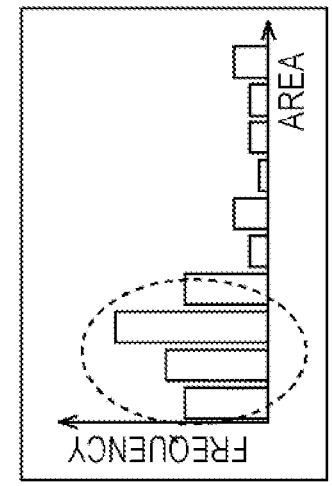
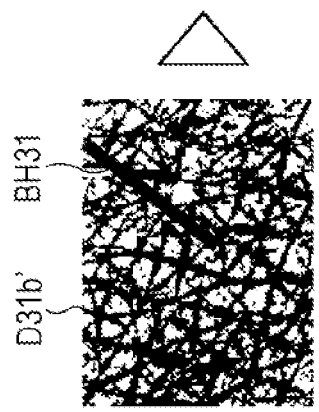
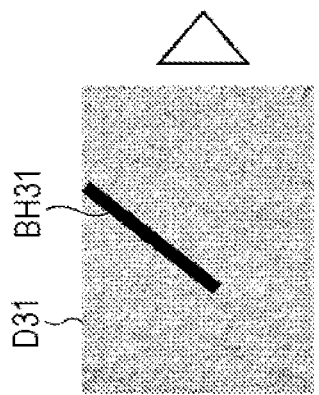

IMAGE PROCESSING DEVICE, IMAGE PROCESSING SYSTEM, IMAGE PROCESSING METHOD, AND PROGRAM

CROSS-REFERENCE TO RELATED APPLICATION

The present application is a national phase entry under 35 U.S.C. §371 of International Application No. PCT/JP2012/082374 filed Dec. 13, 2012, published on Jul. 4, 2013 as WO 2013/099628 A1, which claims priority from Japanese Patent Application No. JP 2011-285560, filed in the Japanese Patent Office on Dec. 27, 2011.

TECHNICAL FIELD

The present technique relates to image processing devices, image processing systems, image processing methods, and programs, and more particularly, to an image processing device, an image processing system, an image processing method, and a program that can be suitably used in cases where a predetermined object in images is detected.

BACKGROUND ART

In a case where a skin condition is analyzed by using an image generated by photographing the skin, it is difficult to accurately detect the shapes of sulci cutis and cristae cutis if a body hair is shown in the image. As a result, analysis precision becomes lower. In view of this, the use of an image from which body hairs have been removed has been considered, so as to increase the precision of skin condition analyses. Therefore, it is essential to accurately detect body hair regions in an image.

Meanwhile, there has been a suggested technique for separating body hair pixels constituting a body hair region in an image from background pixels constituting the regions that are not the body hair region (see Patent Document 1, for example). Specifically, by the technique disclosed in Patent Document 1, body hair pixels are detected by performing binarization to turn pixels into pixels equal to or greater than the mode of the pixel values in the image and pixels smaller than the mode, or body hair pixels are detected by extracting the contour of a body hair with a Sobel filter.

CITATION LIST

Patent Document

Patent Document 1: JP 2010-82245 A

SUMMARY OF THE INVENTION

Problems to be Solved by the Invention

However, the pixels smaller than the mode of pixel values include many pixels that are not body hair pixels. Also, an image contains many contours other than body hairs. Therefore, it is assumed that the error in body hair region detection in images will become large according to the technique disclosed in Patent Document 1.

Therefore, the present technique aims to readily and accurately detect a region that shows a detection object such as a body hair in an image.

Solutions to Problems

An image processing device of a first aspect of the present technique includes a detection object region detection unit that detects a region showing a detection object in an image generated by photographing the detection object. The detection object region detection unit includes: a projective transform unit that generates a projected image by projectively transforming a first image generated by photographing the detection object into the coordinate system of a second image generated by photographing the detection object from a different direction from the first image; a difference image generation unit that generates a difference image between the second image and the projected image; and a region detection unit that detects a candidate region formed with pixels having difference values equal to or larger than a predetermined threshold value in the difference image, and divides the region corresponding to the candidate region in the second image into a detection object region showing the detection object and a non-detection-object region outside the detection object region.

The image processing device may further include a detection object removal unit that removes the detection object from an image generated by photographing the detection object. The detection object removal unit may include: the detection object region detection unit; and a removal unit that removes the detection object from one of the first image and the second image by projecting at least pixels in a region corresponding to a region showing the detection object in the one of the first image and the second image onto pixels in the one of the images to replace the corresponding pixels based on a result of the detection performed by the detection object region detection unit, the pixels projected being in the other one of the first image and the second image.

The removal unit may remove the detection object from the second image by projecting at least pixels in a region in the first image corresponding to the detection object region in the second image onto the second image, and replacing the corresponding pixels.

The removal unit may remove the detection object from the first image by projecting at least pixels in the non-detection-object region in the second image onto the first image, and replacing the corresponding pixels.

The detection object removal unit may select two images from three or more images generated by photographing the detection object from different directions from one another, newly generate an image having the detection object removed therefrom by using the selected two images, and repeat the process of newly generating an image having the detection object removed therefrom by using the newly generated image and one of the remaining images until there are no remaining images.

The detection object region detection unit may further include: a feature point extraction unit that extracts a feature point of the first image and a feature point of the second image; an association unit that associates the feature point of the first image with the feature point of the second image; and a projection matrix calculation unit that calculates a projection matrix generated by projecting the first image onto the coordinate system of the second image based on at least part of the pair of the feature point of the first image and the feature point of the second image associated with each other by the association unit. The projective transform unit may generate the projected image by using the projection matrix.

The projection matrix calculation unit may calculate a plurality of the projection matrices based on a plurality of pairs of the feature points, the projective transform unit may generate a plurality of the projected images by using the respective projection matrices, the difference image generation unit may generate a plurality of the difference images between the second image and the respective projected images, and the region detection unit may detect the candidate region by using the difference image having the smallest difference from the second image among the difference images.

The region detection unit may separate the detection object region from the non-detection-object region by comparing an image in the region of the second image corresponding to the candidate region with surrounding images.

The detection object region detection unit may detect the detection object region in each of three or more images generated by photographing the detection object from different directions from one another. The image processing device may further include a region combination unit that combines the detection object region in an image selected from the three or more images with a region generated by projecting the detection object regions of the remaining images onto the coordinate system of the selected image.

An image processing method of the first aspect of the present technique includes the steps of: generating a projected image by projectively transforming a first image generated by photographing a detection object into the coordinate system of a second image generated by photographing the detection object from a different direction from the first image; generating a difference image between the second image and the projected image; detecting a candidate region formed with pixels having difference values equal to or larger than a predetermined threshold value in the difference image; and dividing the region corresponding to the candidate region in the second image into a detection object region showing the detection object and a non-detection-object region outside the detection object region, the steps being carried out by an image processing device.

A program of the first aspect of the present technique includes the steps of: generating a projected image by projectively transforming a first image generated by photographing a detection object into the coordinate system of a second image generated by photographing the detection object from a different direction from the first image; generating a difference image between the second image and the projected image; detecting a candidate region formed with pixels having difference values equal to or larger than a predetermined threshold value in the difference image; and dividing the region corresponding to the candidate region in the second image into a detection object region showing the detection object and a non-detection-object region outside the detection object region.

An image processing system of a second aspect of the present technique includes: a photographing unit that photographs a detection object; and a detection object region detection unit that detects a region showing the detection object in an image captured by the photographing unit. The detection object region detection unit includes: a projective transform unit that generates a projected image by projectively transforming a first image generated by photographing the detection object with the photographing unit into the coordinate system of a second image generated by photographing the detection object with the photographing unit from a different direction from the first image; a difference image generation unit that generates a difference image between the second image and the projected image; and a region detection unit that detects a candidate region formed with pixels having difference values equal to or larger than a predetermined threshold value in the difference image, and divides the region corresponding to the candidate region in the second image into a detection object region showing the detection object and a non-detection-object region outside the detection object region.

The image processing system may further include a detection object removal unit that removes the detection object from an image generated by photographing the detection object with the photographing unit. The detection object removal unit may include: the detection object region detection unit; and a removal unit that removes the detection object from one of the first image and the second image by projecting at least pixels in a region corresponding to a region showing the detection object in the one of the first image and the second image onto pixels in the one of the images to replace the corresponding pixels based on a result of the detection performed by the detection object region detection unit, the pixels projected being in the other one of the first image and the second image.

The detection object removal unit may select two images from three or more images generated by photographing the detection object with the photographing unit from different directions from one another, newly generate an image having the detection object removed therefrom by using the selected two images, and repeat the process of newly generating an image having the detection object removed therefrom by using the newly generated image and one of the remaining images until there are no remaining images.

The detection object region detection unit may further include: a feature point extraction unit that extracts a feature point of the first image and a feature point of the second image; an association unit that associates the feature point of the first image with the feature point of the second image; and a projection matrix calculation unit that calculates a projection matrix generated by projecting the first image onto the coordinate system of the second image based on at least part of the pair of the feature point of the first image and the feature point of the second image associated with each other by the association unit. The projective transform unit may generate the projected image by using the projection matrix.

The detection object region detection unit may detect the detection object region in each of three or more images generated by photographing the detection object with the photographing unit from different directions from one another. The image processing device may further include a region combination unit that combines the detection object region in an image selected from the three or more images with a region generated by projecting the detection object regions of the remaining images onto the coordinate system of the selected image.

The photographing unit may include: lenses that are two-dimensionally arrayed; and imaging elements. The imaging elements may be provided for each one of the lenses, with positions of the imaging elements relative to the respective lenses being the same. The image processing system may further include an image generation unit that generates images captured by the imaging elements having the same positions relative to the lenses.

The photographing unit may capture an image reflected in a mirror that radially surrounds at least part of a region including the detecting object, and the image processing system may further include: an image cutout unit that cuts out a plurality of images from the image generated by the photographing unit capturing the image reflected in the mirror; and a geometric distortion correction unit that performs geometric distortion correction on the cut-out images.

The first image and the second image may be images captured by the photographing unit taking a closeup image of the detection object.

An image processing device of a third aspect of the present technique includes: a projective transform unit that generates a projected image by projectively transforming a first image generated by photographing a body hair into the coordinate system of a second image generated by photographing the body hair from a different direction from the first image; a difference image generation unit that generates a difference image between the second image and the projected image; a region detection unit that detects a candidate region formed with pixels having difference values equal to or larger than a predetermined threshold value in the difference image, and divides the region corresponding to the candidate region in the second image into a body hair region showing the body hair and a non-body-hair region outside the body hair region; and a removal unit that removes the body hair from one of the first image and the second image by projecting at least the pixels in the region corresponding to the region showing the body hair in the one of the first image and the second image based on a result of the detection performed by the region detection unit, and replacing the corresponding pixels.

In the first aspect of the present technique, a projected image is generated by projectively transforming a first image generated by photographing a detection object into the coordinate system of a second image generated by photographing the detection object from a different direction from the first image, and a difference image between the second image and the projected image is generated. A candidate region formed with pixels having difference values equal to or larger than a predetermined threshold value is detected in the difference image, and the region corresponding to the candidate region in the second image is divided into the detection object region and a non-detection-object region outside the detection object region.

In the second aspect of the present technique, a detection object is photographed, a projected image is generated by projectively transforming a first image generated by photographing the detection object into the coordinate system of a second image generated by photographing the detection object from a different direction from the first image, and a difference image between the second image and the projected image is generated. A candidate region formed with pixels having difference values equal to or larger than a predetermined threshold value is detected in the difference image, and the region corresponding to the candidate region in the second image is divided into the detection object region and a non-detection-object region outside the detection object region.

In the third aspect of the present technique, a projected image is generated by projectively transforming a first image generated by photographing a body hair into the coordinate system of a second image generated by photographing the body hair from a different direction from the first image, and a difference image between the second image and the projected image is generated. A candidate region formed with pixels having difference values equal to or larger than a predetermined threshold value is detected in the difference image, the region corresponding to the candidate region in the second image is divided into a body hair region showing the body hair and a non-body-hair region outside the body hair region. The body hair is removed from one of the first image and the second image by projecting at least the pixels in the region corresponding to the region showing the body hair in the one of the first image and the second image based on a result of the body hair detection, and replacing the corresponding pixels.

Effects of the Invention

According to the first or second aspect of the present technique, a region showing a detection object such as a body hair in an image can be readily and accurately detected.

According to the third aspect of the present technique, a region showing a body hair in an image can be readily and accurately detected. Furthermore, according to the third aspect of the present technique, a body hair in an image can be accurately removed.

BRIEF DESCRIPTION OF DRAWINGS

FIG. 37 is a diagram for explaining the problem in a case where a body hair is not removed from a skin image, and the cosmetic analysis process is performed.

MODES FOR CARRYING OUT THE INVENTION

The following is a description of modes (hereinafter referred to as embodiments) for carrying out the present technique. Explanation will be made in the following order.

1. First embodiment (an example in which body hair regions are detected by using skin images captured from two directions)

2. Second embodiment (an example in which a body hair is removed from a skin image by using skin images captured from two directions)

3. Third embodiment (an example in which body hair regions are detected by using skin images captured from three or more directions)

4. Fourth embodiment (an example in which a body hair is removed from a skin image by using skin images captured from three or more directions)

5. Fifth embodiment (an example in which skin is photographed by one photographing device from different directions with the use of a mirror)

6. Sixth embodiment (an example in which skin is photographed from different directions with the use of microlenses)

7. Seventh embodiment (an example application to cosmetic analysis)

8. Modifications

<1. First Embodiment>

Referring first to FIGS. 1 through 12, a first embodiment of the present technique is described.

[Structure Example of Image Processing System 101]

Figure 1:
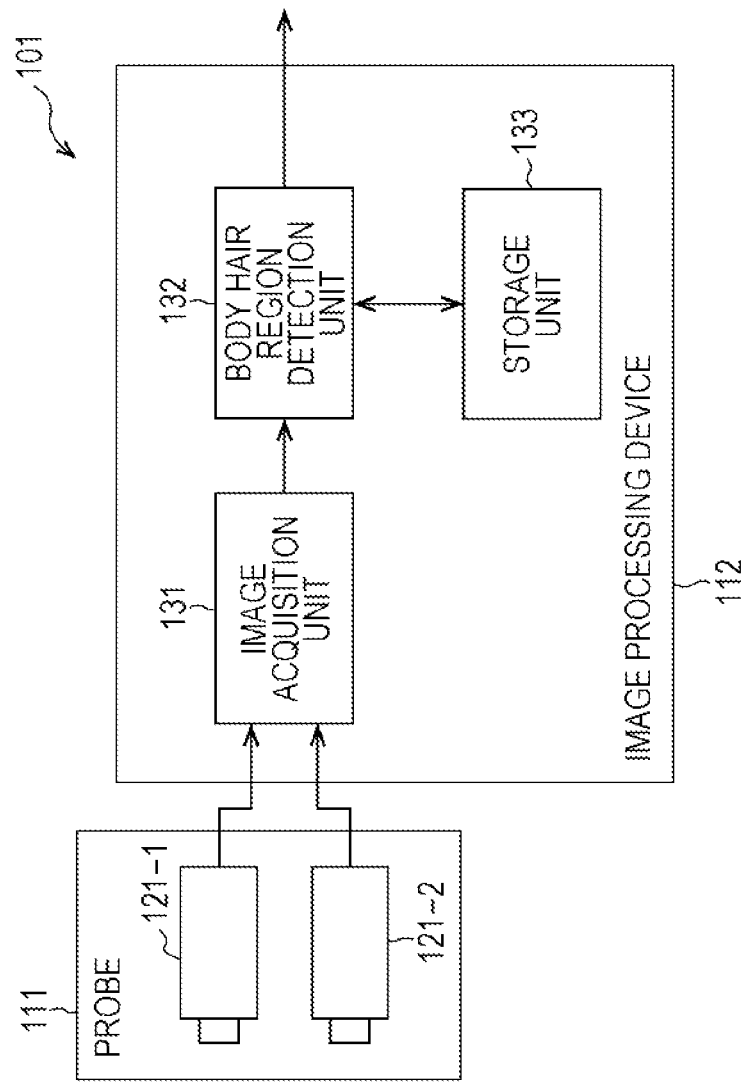
FIG. 1 is a block diagram showing a first embodiment of an image processing system to which the present technique is applied.

FIG. 1 is a block diagram showing an example of functional structure of an image processing system 101 as a first embodiment of an image processing system to which the present technique is applied.

The image processing system 101 is designed to include a probe 111 and an image processing device 112. The image processing system 101 is a system that detects a region that shows a body hair (hereinafter referred to as a body hair region) in an image formed by bringing the probe 111 into contact or close proximity with the skin of a person (hereinafter referred to as a skin image).

The probe 111 is designed to include two photographing devices: photographing devices 121-1 and 121-2. The photographing devices 121-1 and 121-2 may be formed with cameras that are capable of taking closeup images from very short distances (several mm to several cm, for example). The photographing devices 121-1 and 121-2 can be formed with other photographing means than cameras.

The photographing devices 121-1 and 121-2 are placed inside the probe 111 so that the same region of the skin of a person can be photographed from different directions while a predetermined portion of the probe 111 is in contact with or proximity to the skin of the person. The photographing devices 121-1 and 121-2 supply respective captured skin images to the image processing device 112.

The conditions for positioning the photographing devices 121-1 and 121-2 are now described.

The photographing devices 121-1 and 121-2 are positioned so that the respective photographing regions at least partially overlap with each other. The photographing devices 121-1 and 121-2 are also positioned so as to differ from each other in at least the azimuth angle or the depression angle of the center line of the optical axis with reference to the surface of the skin of the person to be photographed. Accordingly, the same region of the skin of the person can be simultaneously photographed from different directions by the photographing devices 121-1 and 121-2. Here, the center line of the optical axis of the photographing device 121-1 and the center line of the optical axis of the photographing device 121-2 do not necessarily intersect each other.

Figure 2:
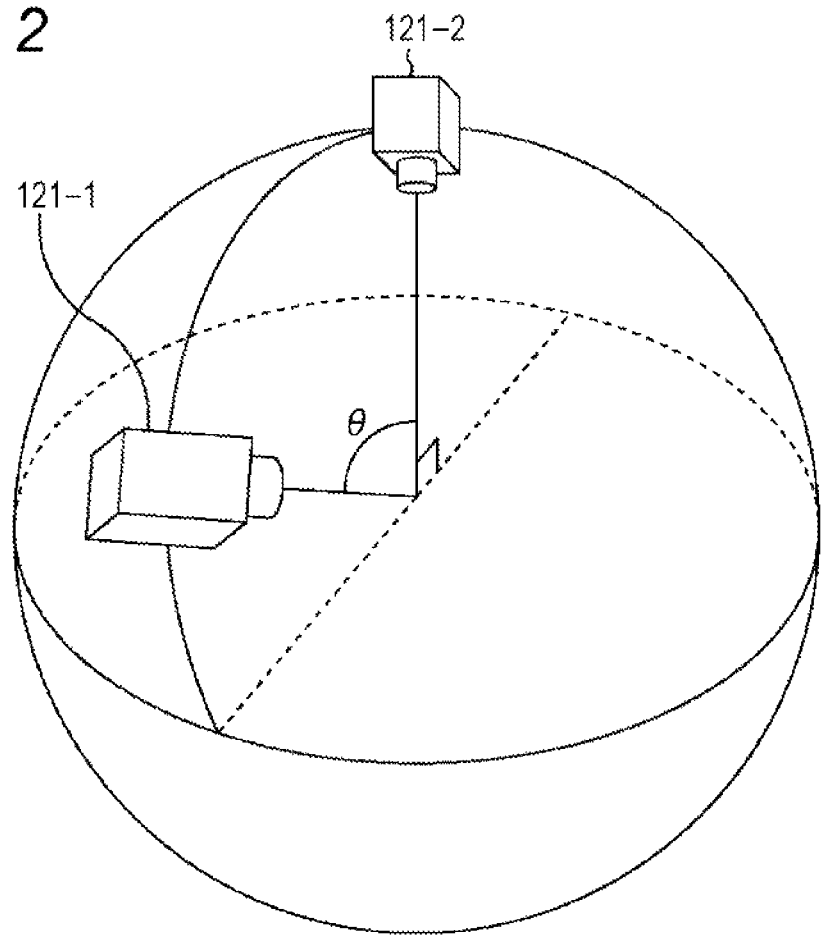
FIG. 2 is a diagram showing an example of ideal positioning of photographing devices in a case where photographing is performed from two directions.
Figure 3:
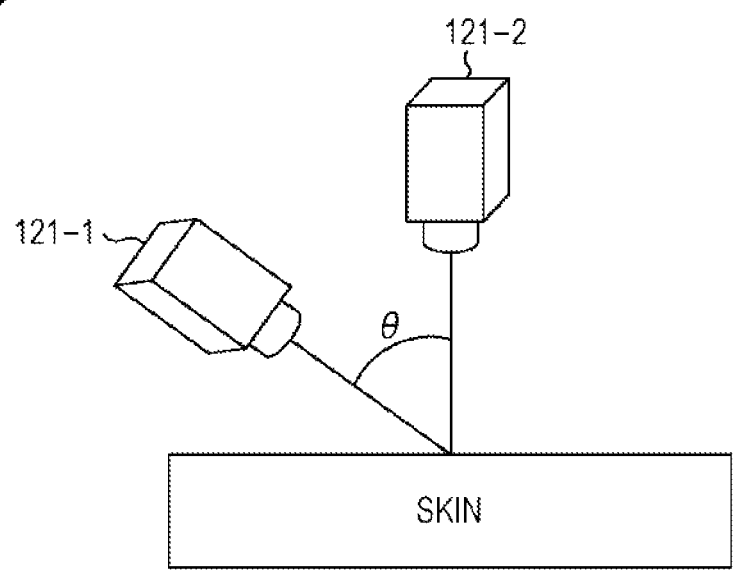
FIG. 3 is a diagram showing an example of ideal positioning of photographing devices in a case where photographing is performed from two directions.

FIGS. 2 and 3 show an example of ideal positioning of the photographing devices 121-1 and 121-2. FIG. 2 is a diagram showing a positional relationship between the photographing devices 121-1 and 121-2, using auxiliary lines. FIG. 3 is a diagram showing the positional relationship between the photographing devices 121-1 and 121-2 of FIG. 2 seen from the side.

The center line of the optical axis of the photographing device 121-1 intersects with the center line of the optical axis of the photographing device 121-2 on the surface of the skin of a person, and the photographing device 121-1 is placed in a direction obliquely upward seen from the intersection point. Accordingly, the photographing device 121-1 can photograph the skin region shared with the photographing device 121-2 from an obliquely upward direction.

Meanwhile, the photographing device 121-2 is placed above the skin so that the center line of the optical axis becomes perpendicular to the surface of the skin or the depression angle of the center line of the optical axis becomes 90 degrees. As a result, the photographing device 121-2 can photograph the skin from directly above, and can obtain a skin image without distortion.

The angle θ between the center line of the optical axis of the photographing device 121-1 and the center line of the optical axis of the photographing device 121-2 is determined by the distance of the body hair from the skin surface and the thickness of the body hair. The angle θ is set at 45 degrees, for example. The depression angle of the center line of the optical axis of the photographing device 121-1 is (90 degrees—θ).

Hereinafter, the photographing device 121-1 and the photographing device 121-2 will be referred to simply as the photographing devices 121 when there is no need to distinguish them from each other.

Referring back to FIG. 1, the image processing device 112 is designed to include an image acquisition unit 131, a body hair region detection unit 132, and a storage unit 133.

The image acquisition unit 131 acquires skin images captured by the photographing device 121-1 and the photographing device 121-2, and supplies the skin images to the body hair region detection unit 132.

The body hair region detection unit 132 detects body hair regions in the acquired skin images, and outputs the skin images and information indicating the detection results to a device in a later stage.

The storage unit 133 stores appropriately the data and the like necessary for the processing in the image processing device 112.

[Structure Example of Body Hair Region Detection Unit 132]

Figure 4:
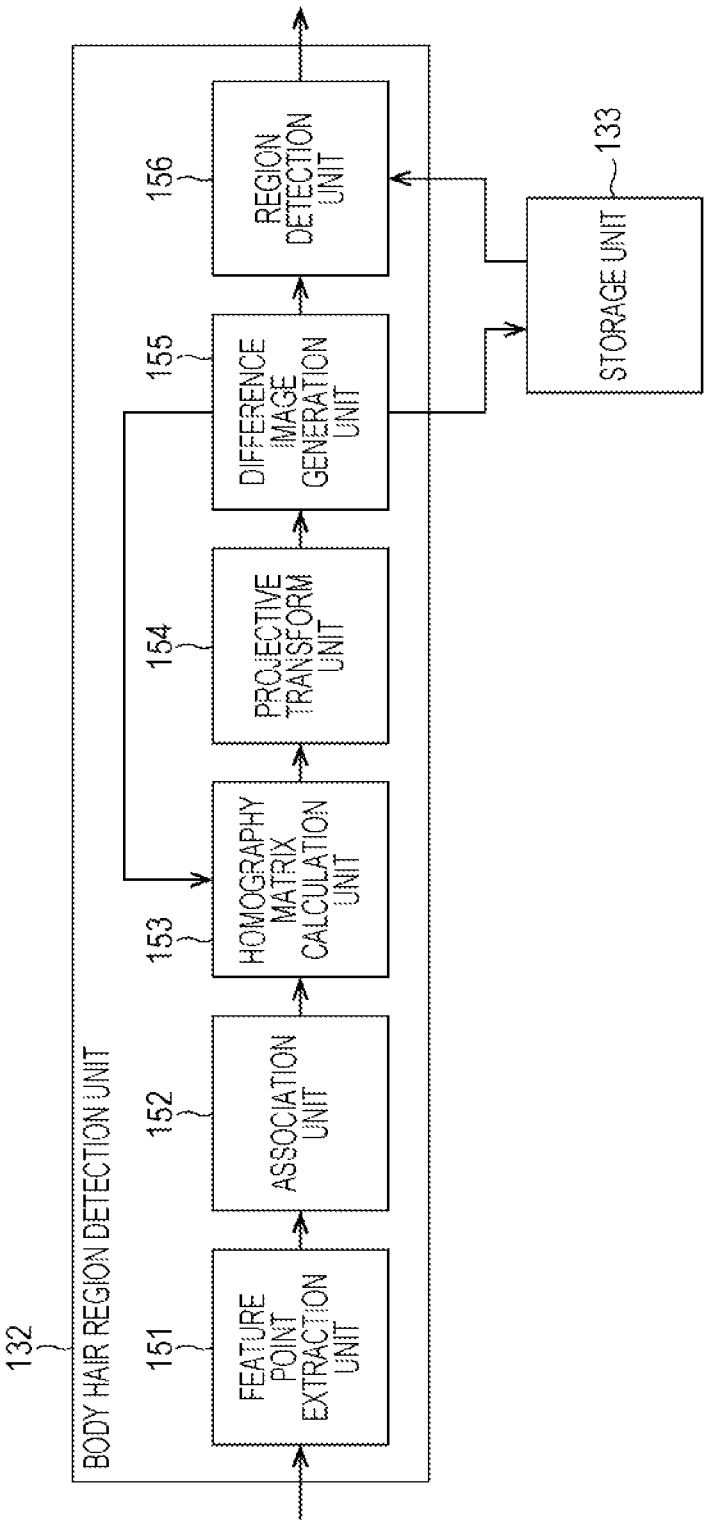
FIG. 4 is a block diagram showing an example structure of a body hair region detection unit.

FIG. 4 is a block diagram showing an example of functional structure of the body hair region detection unit 132.

The body hair region detection unit 132 is designed to include a feature point extraction unit 151, an association unit 152, a homography matrix calculation unit 153, a projective transform unit 154, a difference image generation unit 155, and a region detection unit 156.

The feature point extraction unit 151 extracts feature points of respective skin images. The feature point extraction unit 151 supplies the skin images and information indicating the extracted feature points to the association unit 152.

The association unit 152 associates two skin images with each other in terms of feature points, and detects pairs of feature points that are estimated to be identical. The association unit 152 supplies the skin images and information indicating the results of the feature point pair detection to the homography matrix calculation unit 153.

Based on at least part of the feature point pairs between the two skin images, the homography matrix calculation unit 153 calculates a homography matrix for projectively transforming one skin image (hereinafter also referred to as the projection original image) to the coordinate system of the other skin image (hereinafter also referred to as the projection destination image). The homography matrix calculation unit 153 supplies the skin images, the homography matrix, and information indicating the pairs of feature points used in calculating the homography matrix to the projective transform unit 154.

Using the homography matrix, the projective transform unit 154 projectively transforms the projection original image. The projective transform unit 154 supplies the skin images (the projection original image and the projection destination image), the image generated by the projective transform (hereinafter referred to as the projectively transformed image), the homography matrix, and the information indicating the pairs of feature points used in calculating the homography matrix, to the difference image generation unit 155.

The difference image generation unit 155 generates a difference image between the projectively transformed image and the projection destination image. The difference image generation unit 155 stores the difference image, as well as the homography matrix and information indicating the pairs of feature points used in the process of generating the difference image, into the storage unit 133. The difference image generation unit 155 also instructs the homography matrix calculation unit 153 to calculate a homography matrix, if necessary. When completing the generation of the difference image, the difference image generation unit 155 supplies the skin images (the projection original image and the projection destination image) to the region detection unit 156.

The region detection unit 156 detects a body hair region in the projection destination image based on the difference image stored in the storage unit 133. The region detection unit 156 outputs the skin images (the projection original image and the projection destination image), as well as information indicating the result of the body hair region detection, to a later stage. The region detection unit 156 also outputs information indicating at least the homography matrix or the pairs of feature points used in the process of generating the difference image used in detecting the body hair region, to a later stage.

[Body Hair Detection Process by Image Processing System 101]

Figure 5:
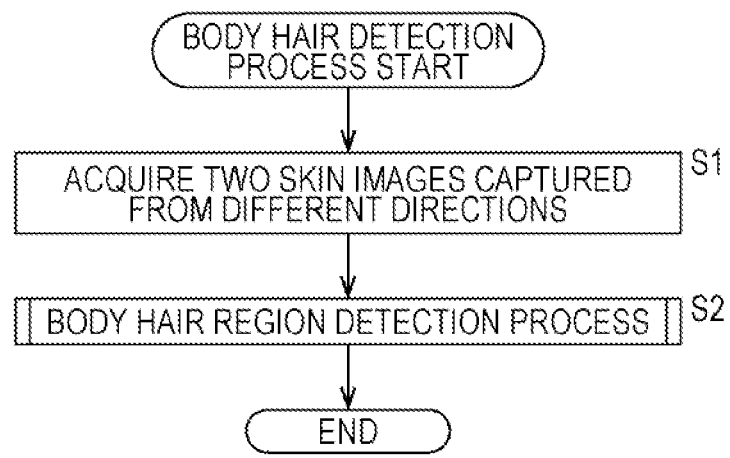
FIG. 5 is a flowchart for explaining a first embodiment of a body hair detection process.

Referring now to the flowchart shown in FIG. 5, the body hair detection process to be performed by the image processing system 101 is described.

Figure 6:
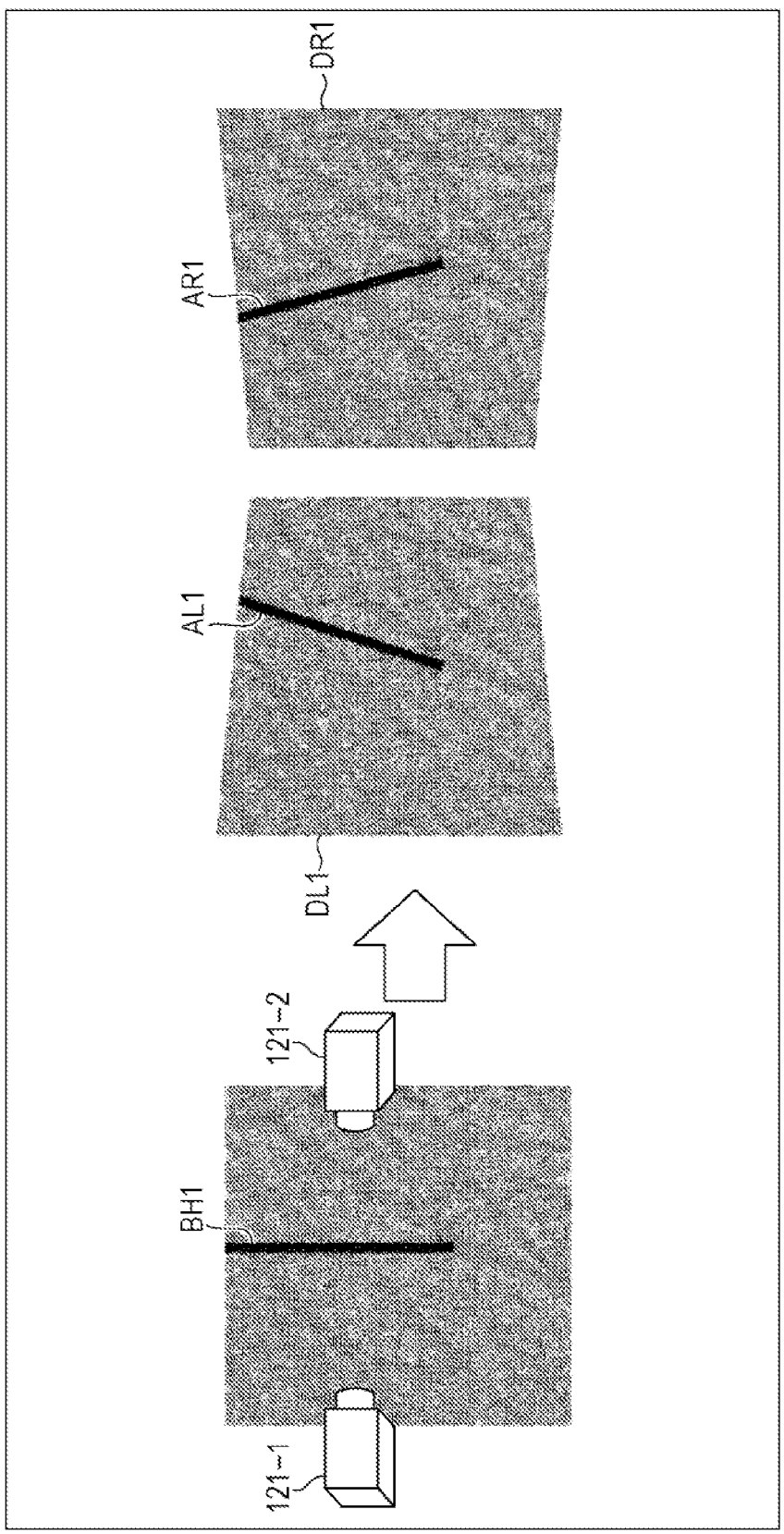
FIG. 6 is a diagram for explaining a specific example of the body hair detection process.

The following is a description of a process to be performed in a case where a region of the skin in which a body hair BH1 exists is photographed in an obliquely downward direction from the left by the photographing device 121-1, and is photographed in an obliquely downward direction from the right by the photographing device 121-2, as shown in FIG. 6, appropriately accompanied with a specific example.

In step S1, the image processing system 101 acquires two skin images captured from different directions. Specifically, the photographing devices 121-1 and 121-2 almost simultaneously photograph the skin of a person from different directions from each other. At this point, the photographing devices 121-1 and 121-2 capture closeup images of the skin from short distances, with the probe 111 being in contact with or close proximity to the skin, for example. The photographing devices 121-1 and 121-2 then supply the skin images obtained as a result of the photographing, to the image acquisition unit 131. The image acquisition unit 131 supplies the acquired skin images to the feature point extraction unit 151 of the body hair region detection unit 132.

For example, as shown in FIG. 6, a skin image including an image DL1 is captured by the photographing device 121-1, and a skin image including an image DR1 is captured by the photographing device 121-2. The image DL1 and the image DR1 are the portions corresponding to the same skin region extracted from the respective skin images captured by the photographing device 121-1 and the photographing device 121-2.

A body hair region AL1 and a body hair region AR1 each showing the body hair BH1 exist in the image DL1 and the image DR1, respectively. Since the image DL1 and the image DR1 are captured from different directions from each other, different skin regions are hidden by the body hair BH1. That is, the skin region hidden by the body hair region AL1 in the image DL1 differs from the skin region hidden by the body hair region AR1 in the image DR1.

The left side of the image DL1 is long while the right side is short, because the left-side region is the closest to the photographing device 121 and is shown as a large region, and regions closer to the right side are shown smaller. The right side of the image DR1 is long while the left side is short for the same reason as above.

In the following, a case where processing is performed on the image DL1 and the image DR1 will be described appropriately as a specific example.

In step S2, the body hair region detection unit 132 performs a body hair region detection process, and then ends the body hair detection process.

Figure 7:
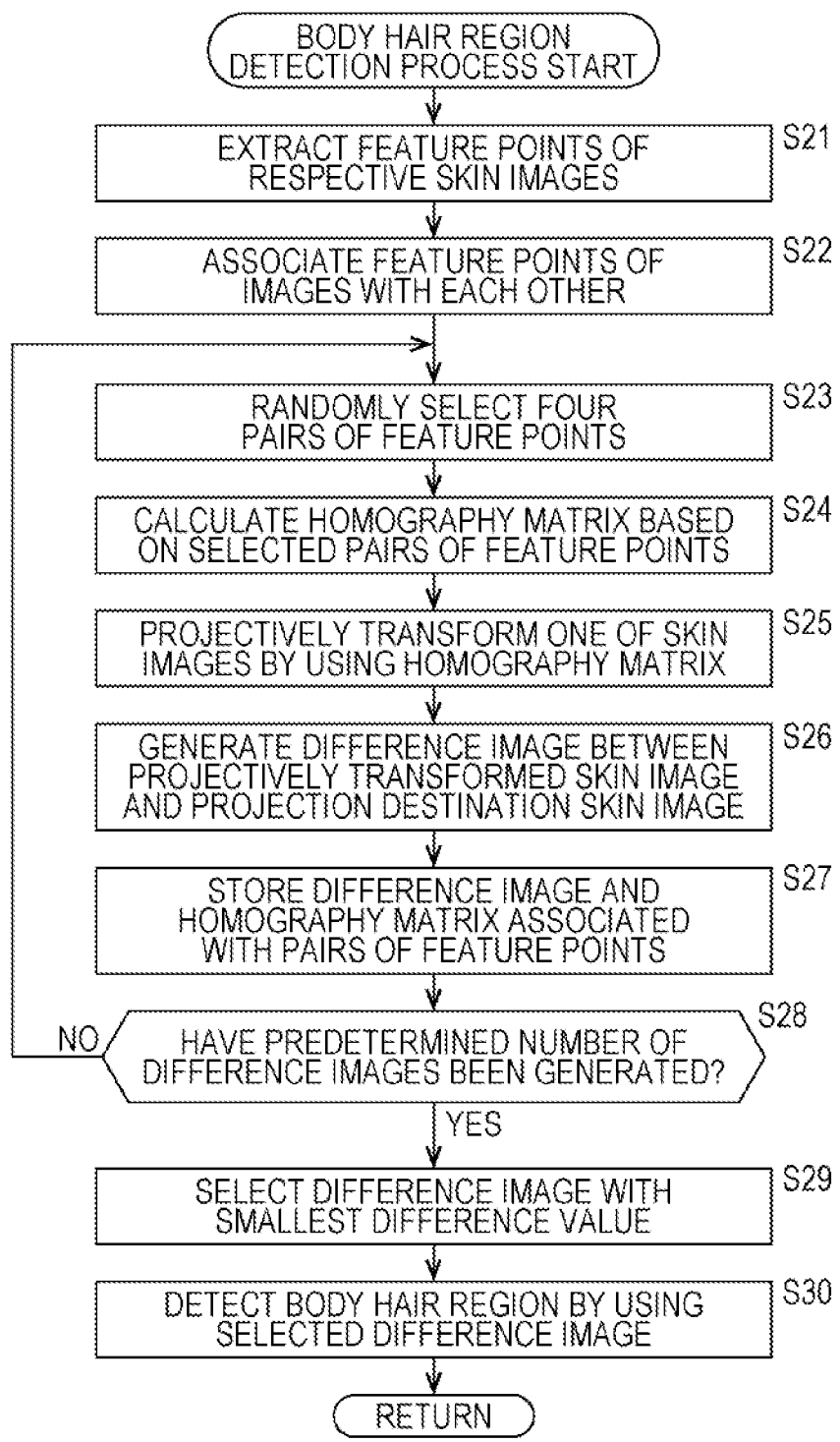
FIG. 7 is a flowchart for explaining a body hair region detection process in detail.

Referring now to the flowchart shown in FIG. 7, the body hair region detection process is described in detail.

In step S21, the feature point extraction unit 151 extracts feature points of the respective skin images. The feature point extraction unit 151 then supplies the skin images and information indicating the extracted feature points to the association unit 152.

The method of extracting the feature points may be any appropriate method. For example, based on information unique to the skin, such as the intersection points between sulci cutis, cristae cutis, pores, sweat glands, and the blood vessel pattern of the skin surface, the feature points can be extracted by using SIFT (Scale Invariant Feature Transform) feature quantities or SURF (Speeded Up Robust Features) feature quantities that do not vary with changes in images caused by rotation, scale changes, or illumination changes.

In step S22, the association unit 152 associates the feature points of the images with each other. Specifically, the association unit 152 detects the pair of feature points that are estimated to be the same among the combinations of the feature points of one of the skin images and the feature points of the other one of the skin images.

In a case where the feature points are extracted based on the SIFT feature quantities, for example, the association unit 152 selects one of the feature points of the image DL1, and calculates intervector distances by using vector information about the SIFT feature quantities between the selected feature point and the respective feature points of the image DR1. The association unit 152 associates the selected feature point of the image DL1 with the feature point of the image DR1 with which the intervector distance is the shortest, to form the pair of the same feature points. The association unit 152 performs this process on all the feature points.

Figure 8:
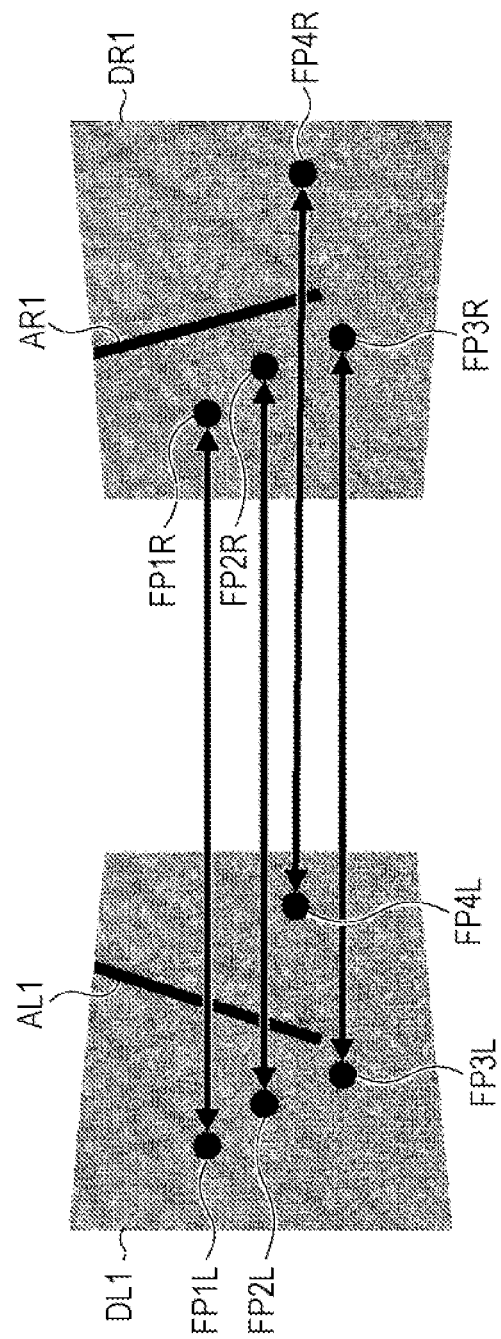
FIG. 8 is a diagram for explaining a method of calculating a homography matrix.

In step S23, the homography matrix calculation unit 153 randomly selects four pairs of feature points. For example, as shown in FIG. 8, the homography matrix calculation unit 153 selects four pairs of feature points: feature points FP1L through FP4L of the image DL1, and feature points FP1R through FP4R of the image DR1 that form pairs with the feature points FP1L through FP4L.

In step S24, the homography matrix calculation unit 153 calculates a homography matrix based on the selected pairs of feature points. For example, based on the four pairs of the feature points shown in FIG. 8, the homography matrix calculation unit 153 calculates a homography matrix $H_{LR}$ for projecting the image DL1 (the projection original image) onto the coordinate system of the image DR1 (the projection destination image). The homography matrix calculation unit 153 then supplies the skin images, the calculated homography matrix, and information indicating the pairs of feature points used in calculating the homography matrix to the projective transform unit 154.

Figure 9:
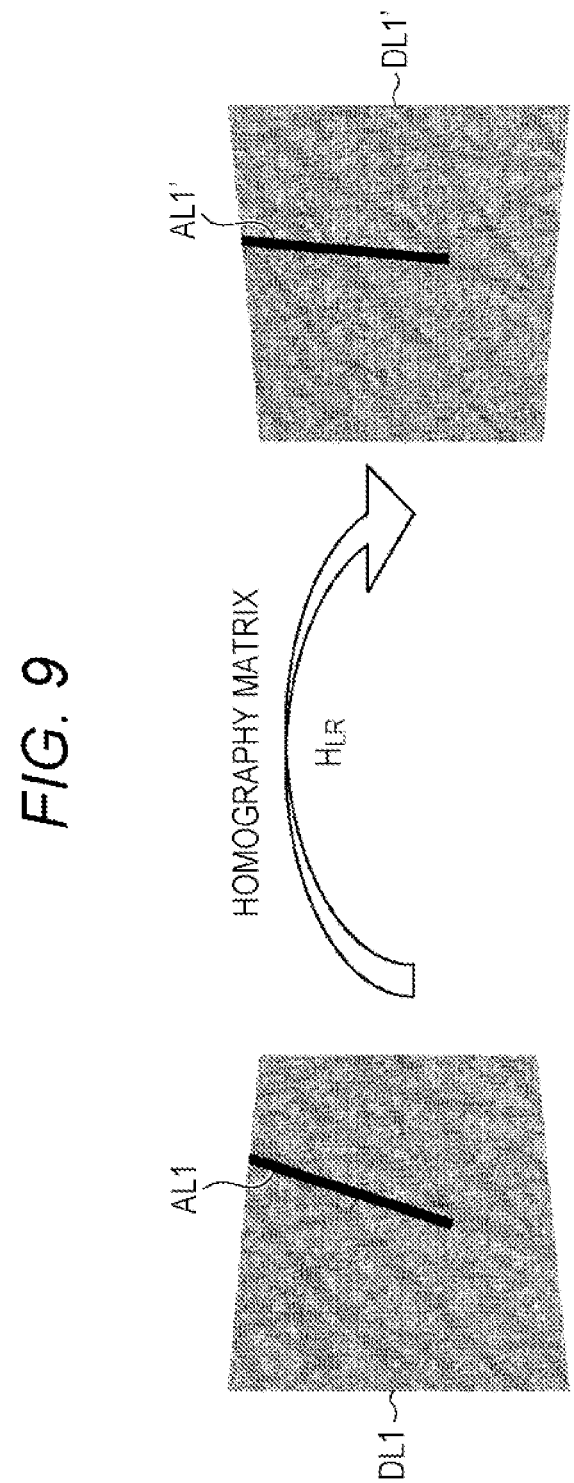
FIG. 9 is a diagram for explaining a specific example of projective transform of a skin image.

In step S25, the projective transform unit 154 projectively transforms one of the skin images by using the homography matrix. For example, as shown in FIG. 9, the projective transform unit 154 projectively transforms the image DL1 (the projection original image) by using the homography matrix $H_{LR}$ calculated by the homography matrix calculation unit 153, to generate an image DL1' (a projectively transformed image). At this point, the body hair region AL1 in the image DL1 is projected as a body hair region AL1' in the image DL1'. The body hair region AL1' is a different region from the body hair region AR1 in the image DR.

The projective transform unit 154 then supplies the skin images (the projection original image and the projection destination image), the projectively transformed image, the homography matrix, and the information indicating the pairs of feature points used in calculating the homography matrix, to the difference image generation unit 155.

Figure 10:
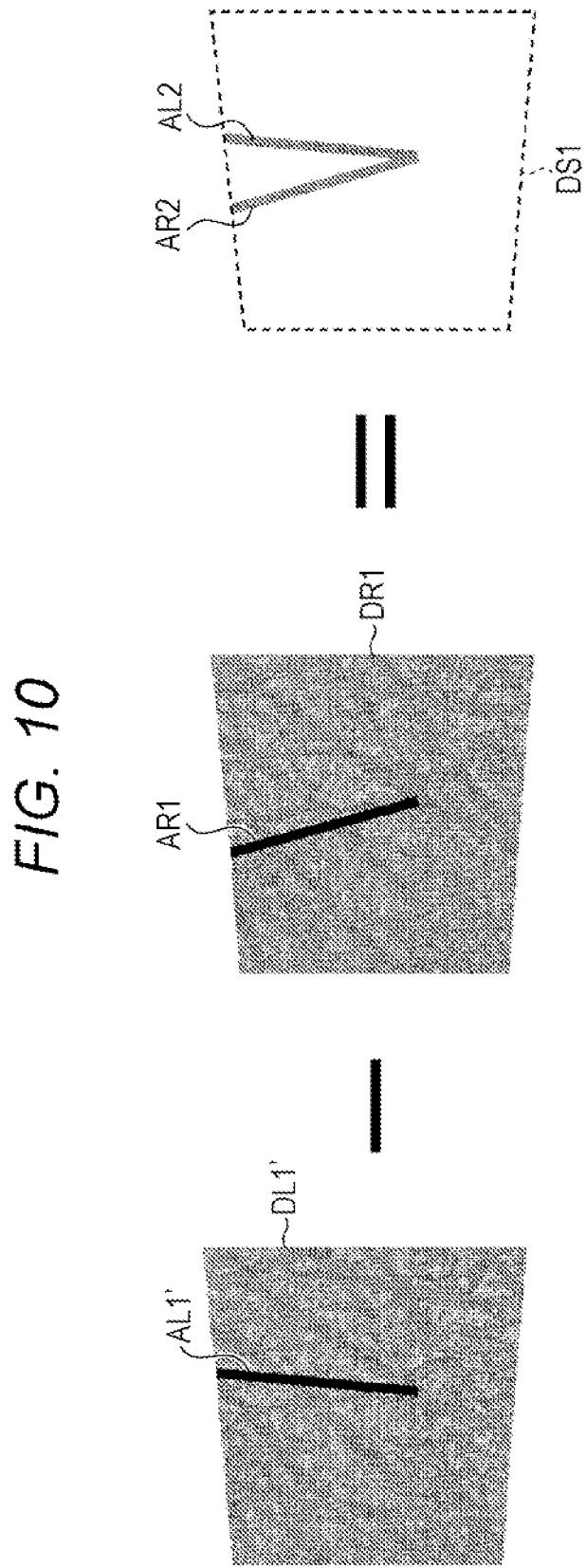
FIG. 10 is a diagram for explaining a method of generating a difference image.

In step S26, the difference image generation unit 155 generates a difference image between the skin image that has been projectively transformed (the projectively transformed image) and the skin image as the projection destination (the projection destination image). For example, as shown in FIG. 10, the difference image generation unit 155 generates a difference image DS1 formed with the absolute values of the difference values in the corresponding pixels between the image DL1' and the image DR. In the difference image DS1, the difference value between a region AL2 corresponding to the body hair region AL1' and a region AR2 corresponding to the body hair region AR1 is larger.

In step S27, the difference image generation unit 155 stores the generated difference image associated with the homography matrix and the information indicating a combination of the four pairs of feature points used in the process of generating the difference image, into the storage unit 133.

In step S28, the difference image generation unit 155 determines whether a predetermined number of difference images have been generated. If it is determined that the predetermined number of difference images have not been generated, the process returns to step S23. At this point, the difference image generation unit 155 instructs the homography matrix calculation unit 153 to calculate a homography matrix.

After that, the procedures of steps S23 through S28 are repeated a predetermined number of times. Specifically, the process of randomly selecting four pairs of feature points, and generating a difference image between a projectively transformed image projectively transformed by using a homography matrix calculated based on the selected pairs of feature points and the projection destination image, is repeated.

If it is determined in step S28 that the predetermined number of difference images have been generated, on the other hand, the process moves on to step S29. At this point, the difference image generation unit 155 supplies the skin images (the projection original image and the projection destination image) to the region detection unit 156.

In step S29, the region detection unit 156 selects the difference image with the smallest difference value. Specifically, the region detection unit 156 selects the difference image with the smallest sum of difference values among the difference images stored in the storage unit 133.

In step S30, the region detection unit 156 detects a body hair region by using the selected difference image. Specifically, the region detection unit 156 first detects a region formed with pixels having difference values equal to or larger than a predetermined threshold value in the selected difference image, as a candidate body hair region. For example, the region in the projection destination image corresponding to the region formed with the region AL2 and the region AR2 in the difference image DS1 in FIG. 10 is detected as the candidate body hair region.

The region AR2 is a region (a body hair region) actually showing a body hair in the projection destination image (the image DR1). Meanwhile, the region AL2 is a region (hereinafter referred to as a non-body-hair region) that does not show a body hair in the projection destination image and shows a body hair in the projectively transformed image (the image DL1'). Normally, a candidate body hair region is detected as a region in which the body hair region and the non-body-hair region are continuous at the root (the base). However, a candidate body hair region corresponding to a body hair that does not have its root (base) shown in skin images is detected as two regions that are a body hair region and a non-body-hair region at a distance from each other.

The region detection unit 156 further divides the candidate body hair region into a region (a body hair region) actually showing a body hair in the projection destination image, and the other region (a non-body-hair region).

Figure 11:
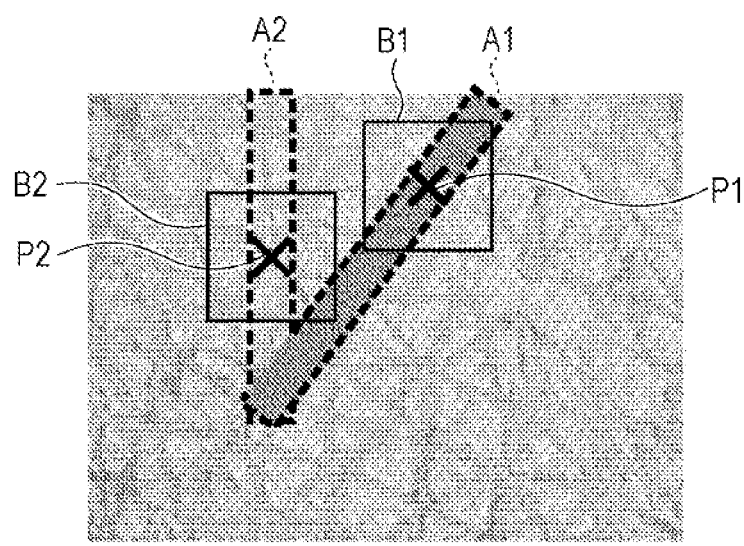
FIG. 11 is a diagram for explaining a method of detecting a body hair region.

The method of separating the body hair region from the non-body-hair region is now described. A separation method to be used in a case where a candidate body hair region formed with a body hair region A1 and a non-body-hair region A2 is detected as shown in FIG. 11 is appropriately described below.

For example, the region detection unit 156 selects one pixel as the current pixel from the candidate body hair region in the projection destination image. The region detection unit 156 further detects the largest pixel value among the respective pixels in a rectangular region of a predetermined size (hereinafter referred to as the current region) having the current pixel at its center. The largest pixel value indicates the largest luminance value in the current region.

In a case where the difference between the pixel value of the current pixel and the largest pixel value is equal to or larger than a predetermined threshold value, the region detection unit 156 determines the current pixel to be a pixel in the body hair region. In a case where the difference between the pixel value of the current pixel and the largest pixel value is smaller than the predetermined threshold value, the region detection unit 156 determines that the current pixel is a pixel in the non-body-hair region.

In a case where a pixel P1 in the body hair region A1 is the current pixel, for example, the pixel P1 is a pixel on a body hair, and has a pixel value close to 0. Therefore, the pixel value difference from the largest pixel value in a current region B1 having the pixel P1 at its center is large. In view of this, the pixel P1 is determined to be a pixel in the body hair region A1. In a case where a pixel P2 in the non-body-hair region A2 is the current pixel, for example, the pixel P2 is a pixel on the skin, and the pixel value difference from the largest pixel value in the current region B2 having the pixel P2 at its center is small. In view of this, the pixel P2 is determined to be a pixel in the non-body-hair region A2.

The length (the number of pixels) of one side of the current region is preferably set at a value that is larger than the largest number of pixels in the thickness direction of a body hair assumed in a skin image and is close to the largest number of pixels. For example, in a skin image that is obtained by taking a closeup image at 70-fold magnification and has a resolution of 1280×1024 pixels, the length of one side of the current region is set at 51 pixels.

The region detection unit 156 repeats the above process until all the pixels in the candidate body hair region have been processed as current pixels, to divide the pixels in the candidate body hair region into pixels in the body hair region and pixels in the non-body-hair region. Images in the candidate body hair region are compared with images in the surrounding regions, so that the candidate body hair region is divided into the body hair region and the non-body-hair region.

Figure 12:
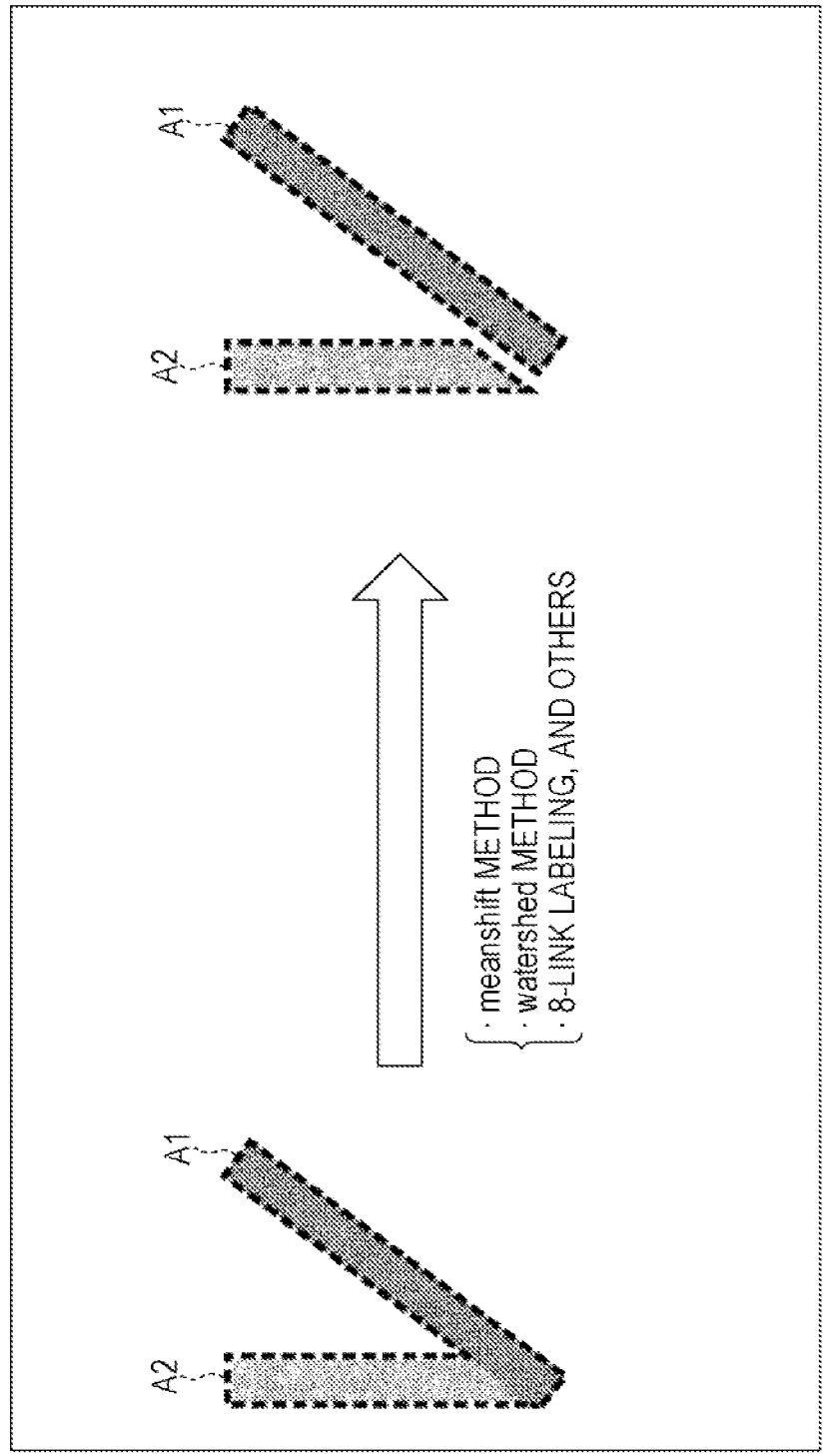
FIG. 12 is a diagram for explaining methods of detecting a body hair region.

The method of separating a body hair region from a non-body-hair region is not limited to the above described method. For example, determination may not be performed on a pixel-by-pixel basis. As shown in FIG. 12, a candidate body hair region may be divided into a region A1 and a region A2, before a check is made to determine which one of the regions is a body hair region or is a non-body-hair region. In this case, only some of the pixels in the respective regions, instead of all of the pixels in the respective regions, are used in the determination.

The region detection unit 156 outputs the skin images (the projection original image and the projection destination image), as well as the information indicating the results of the detection of the body hair region and the non-body-hair region, and the homography matrix used in the process of generating the difference image used in detecting the body hair region, to a later stage.

Hereinafter, the homography matrix used in the process of generating the difference image used in detecting the body hair region will be referred to as an optimum homography matrix. The optimum homography matrix is a homography matrix with the smallest difference between the projectively transformed image and the projection destination image among the calculated homography matrices.

In the above described manner, body hair regions in skin images can be readily and accurately detected.

<2. Second Embodiment>

Referring now to FIGS. 13 through 16, a second embodiment of the present technique is described. The second embodiment of the present technique is the same as the first embodiment, except for further including a function to remove a body hair from skin images.

[Structure Example of Image Processing System 201]

Figure 13:
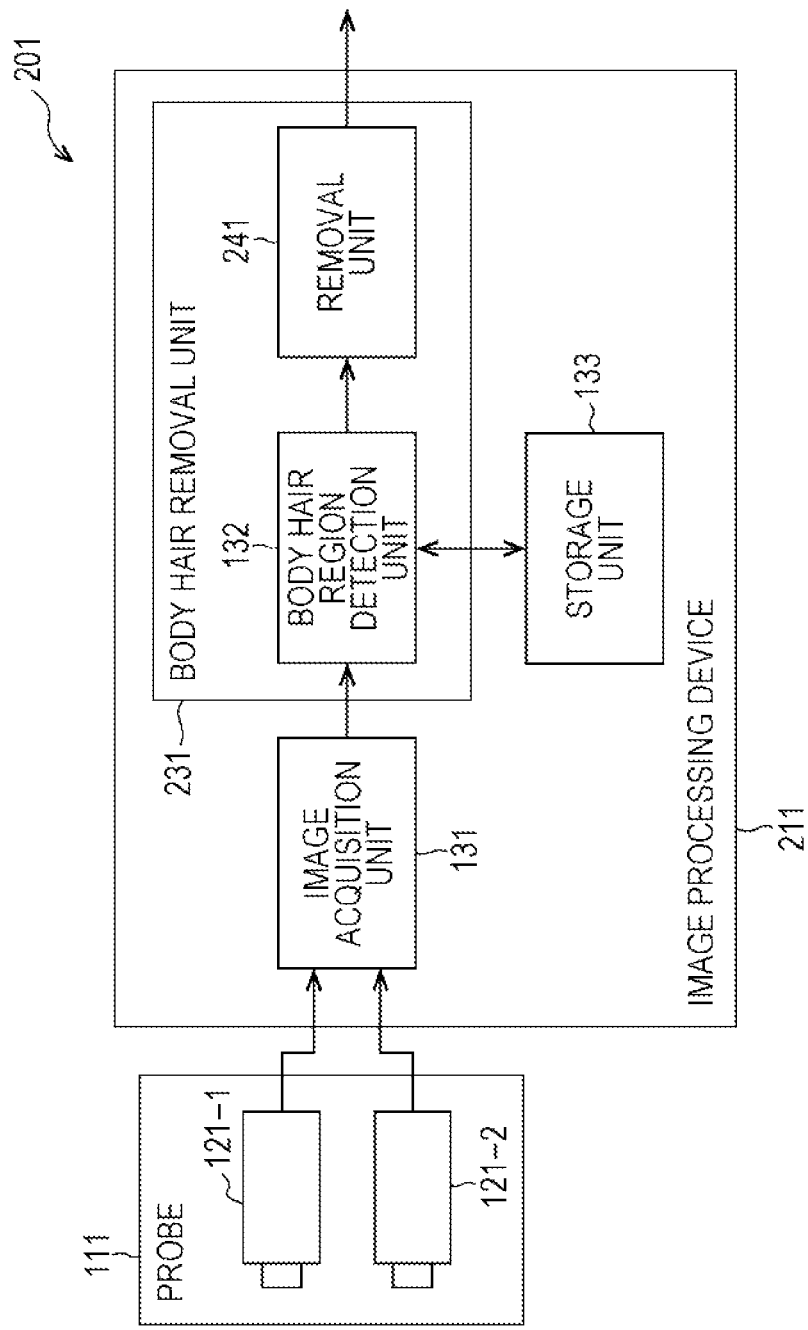
FIG. 13 is a block diagram showing a second embodiment of an image processing system to which the present technique is applied.

FIG. 13 is a block diagram showing an example of functional structure of an image processing system 201 as the second embodiment of an image processing system to which the present technique is applied.

The image processing system 201 is a system formed by adding a function of removing a body hair from skin images to the image processing system 101. In the drawing, the components equivalent to those in FIG. 1 are denoted by the same reference numerals as those used in FIG. 1, and explanation of the components that perform the same processes as above is not repeated herein.

The image processing system 201 differs from the image processing system 101 of FIG. 1 in that the image processing device 112 is replaced with an image processing device 211. Also, the image processing device 211 differs from the image processing device 112 in further including a body hair removal unit 231.

The body hair removal unit 231 is designed to include a body hair region detection unit 132 and a removal unit 241.

Based on the result of body hair region detection by the body hair region detection unit 132, the removal unit 241 generates an image (hereinafter referred to as a body-hair removed image) that is a skin image having the body hair removed therefrom. The removal unit 241 outputs the generated body-hair removed image to a later stage.

[Body Hair Removal Process by Image Processing System 201]

Figure 14:
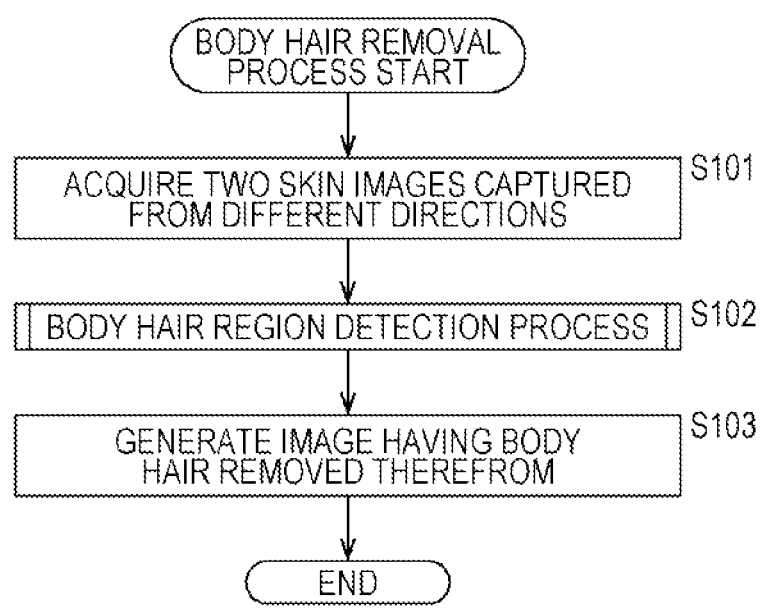
FIG. 14 is a flowchart for explaining a first embodiment of a body hair removal process.

Referring now to the flowchart shown in FIG. 14, the body hair removal process to be performed by the image processing system 201 is described.

In step S101, two skin images captured from different directions are acquired, as in the procedure of step S1 in FIG. 5.

In step S102, a body hair region detection process is performed, as in the procedure of step S2 in FIG. 5. A region detection unit 156 of the body hair region detection unit 132 then supplies the skin images (the projection original image and the projection destination image), as well as information indicating the results of the detection of a body hair region and a non-body-hair region, and the optimum homography matrix, to the removal unit 241.

In step S103, the removal unit 241 generates an image from which a body hair has been removed. Specifically, the removal unit 241 replaces at least the pixels in the body hair region in the projection destination image with the corresponding pixels in the projection original image, to generate a body-hair removed image.

For example, the removal unit 241 calculates the inverse of the optimum homography matrix. Using the inverse of the optimum homography matrix, the removal unit 241 calculates the region in the projection original image corresponding to the non-body-hair region in the candidate body hair region, or the body hair region in the projection original image. The removal unit 241 then projects the pixels outside the body hair region of the projection original image onto the projection destination image by using the optimum homography matrix, to replace pixels in the projection destination image. In this manner, the pixels in the body hair region including part of the non-body-hair region in the projection destination image are replaced with the corresponding pixels in the projection original image, and an image (the body-hair removed image) that is the projection destination image having the body hair removed therefrom is generated.

Figure 15:
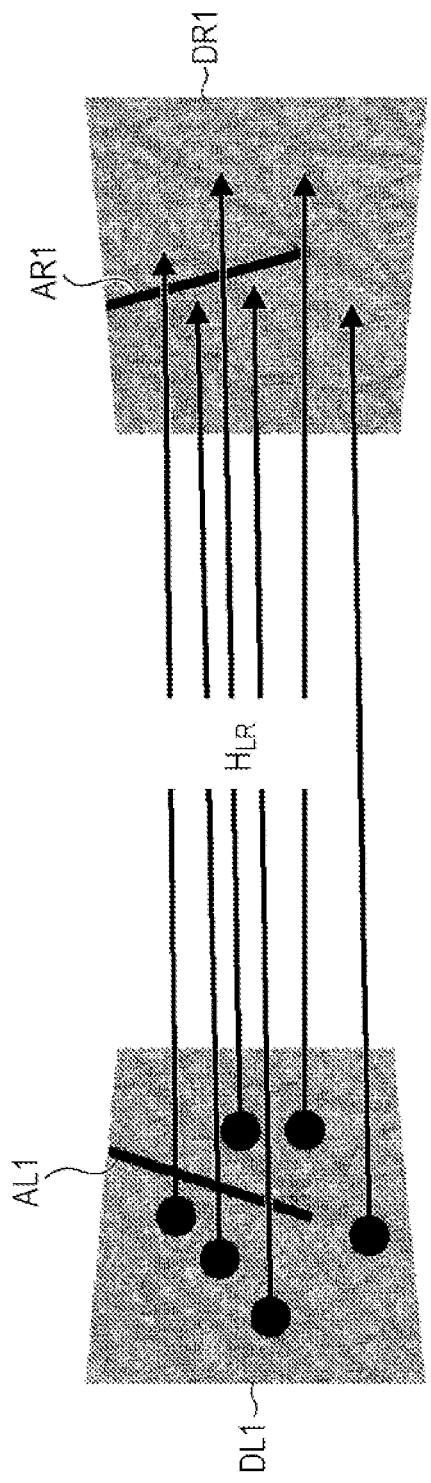
FIG. 15 is a diagram for explaining a first method of removing a body hair from a skin image.

For example, the removal unit 241 projects the pixels outside a body hair region AL1 in an image DL1 on an image DR1 by using an optimum homography matrix $H_{LR}$, as shown in FIG. 15, to replace pixels in the image DR1. As a result, a body hair region AR1 is removed from the image DR1, and a body-hair removed image showing the skin that was hidden by the body hair region AR1, instead, is generated.

Alternatively, the removal unit 241 calculates the region in the projection original image corresponding to the body hair region in the projection destination image by using the inverse of the optimum homography matrix. The calculated region is a different region from the body hair region in the projection original image, and does not show the body hair. The removal unit 241 then projects the pixels inside the region in the calculated projection original image onto the projection destination image by using the optimum homography matrix, to replace pixels in the projection destination image. In this manner, the pixels in the body hair region in the projection destination image are replaced with the corresponding pixels in the projection original image, and an image (the body-hair removed image) that is the projection destination image having the body hair removed therefrom is generated.

Figure 16:
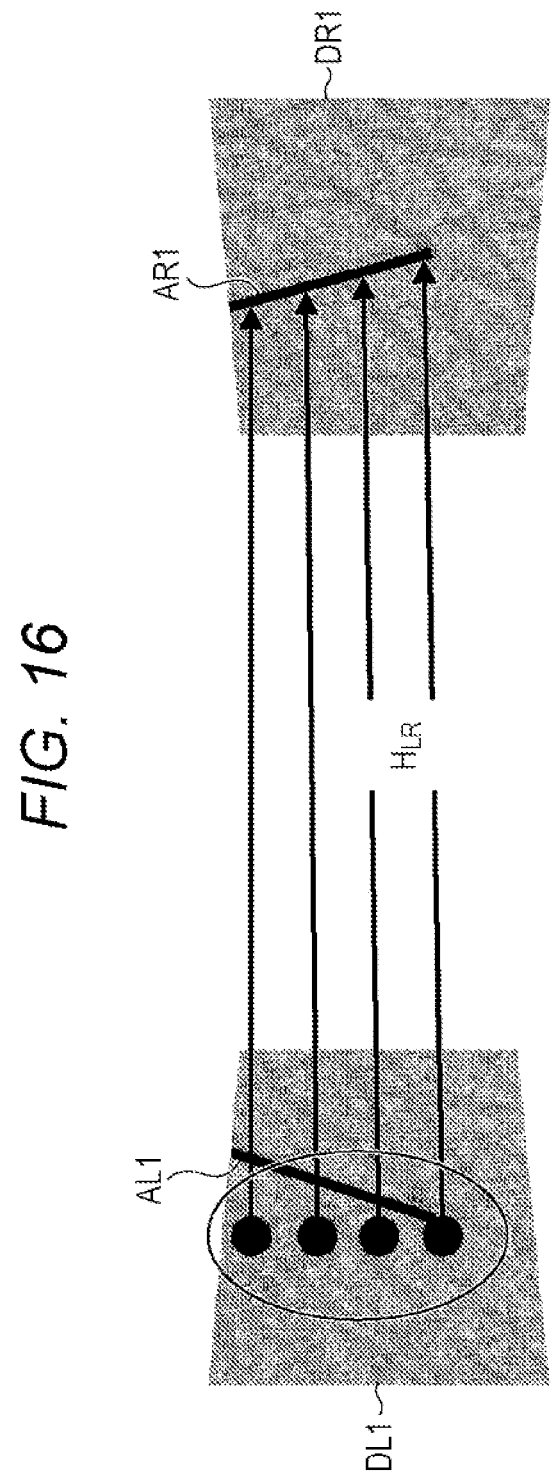
FIG. 16 is a diagram for explaining a second method of removing a body hair from a skin image.

For example, the removal unit 241 calculates the region in the image DL1 corresponding to the body hair region AR1 in the image DR1. As shown in FIG. 16, the removal unit 241 then projects the pixels inside the calculated region in the image DL1 (the pixels surrounded by the circle in the drawing) onto the image DR1 by using the optimum homography matrix, to replace pixels (the pixels in the body hair region AR1) in the image DR1. As a result, the body hair region AR1 is removed from the image DR1, and a body-hair removed image showing the skin that was hidden by the body hair region AR1, instead, is generated.

The latter method can reduce the number of pixels to be projected, and shorten the processing time.

The removal unit 241 then outputs the generated body-hair removed image to a later stage.

In the above manner, a body hair can be readily and certainly removed from skin images.

<3. Third Embodiment>

Referring now to FIGS. 17 through 23, a third embodiment of the present technique is described. In the third embodiment of the present technique, a body hair region is detected by using three or more skin images acquired by photographing the skin from three or more different directions.

Since a body hair is in a linear form, it is preferable to capture skin images from two directions that are perpendicular to the extending direction of the body hair, as described above with reference to FIG. 6. This is because doing so will increase the probability (or the area) that a skin region hidden by the body hair in one skin image is not hidden by the body hair but is shown in the other skin image.

Figure 17:
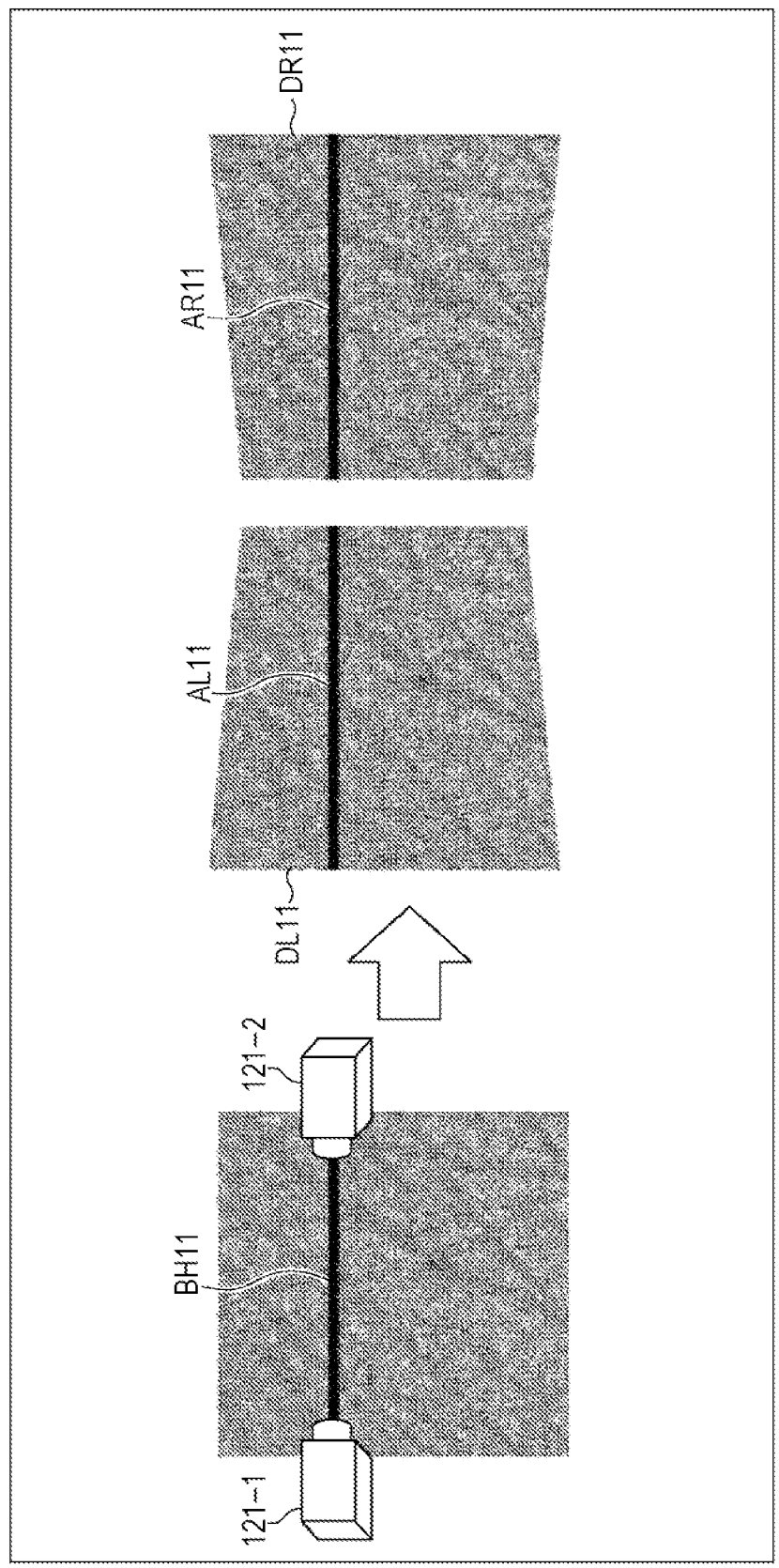
FIG. 17 is a diagram for explaining the problem with photographing a skin from two directions.

However, a body hair does not always extend in one direction but may extend in various manners. Therefore, skin images are not always captured from two directions perpendicular to the extending direction of a body hair. For example, as shown in FIG. 17, there are cases where a photographing device 121-1 and a photographing device 121-2 perform photographing from two directions that are parallel to the extending direction of a body hair BH11 and are the opposite directions from each other. In such a case, the skin regions hidden by the body hair BH11 overlap each other when seen from the two photographing devices. That is, the skin region hidden by a body hair region AL11 in an image DL11 obtained by the photographing device 121-1 overlaps the skin region hidden by a body hair region AR11 in an image DR11 obtained by the photographing device 121-2. In this case, the difference value of the region corresponding to the body hair region in a difference image is small. As a result, it is difficult to accurately detect the body hair region.

In view of this, in the third embodiment of the present technique, the skin is photographed from three or more directions so that a body hair region can be more accurately detected.

[Structure Example of Image Processing System 301]

Figure 18:
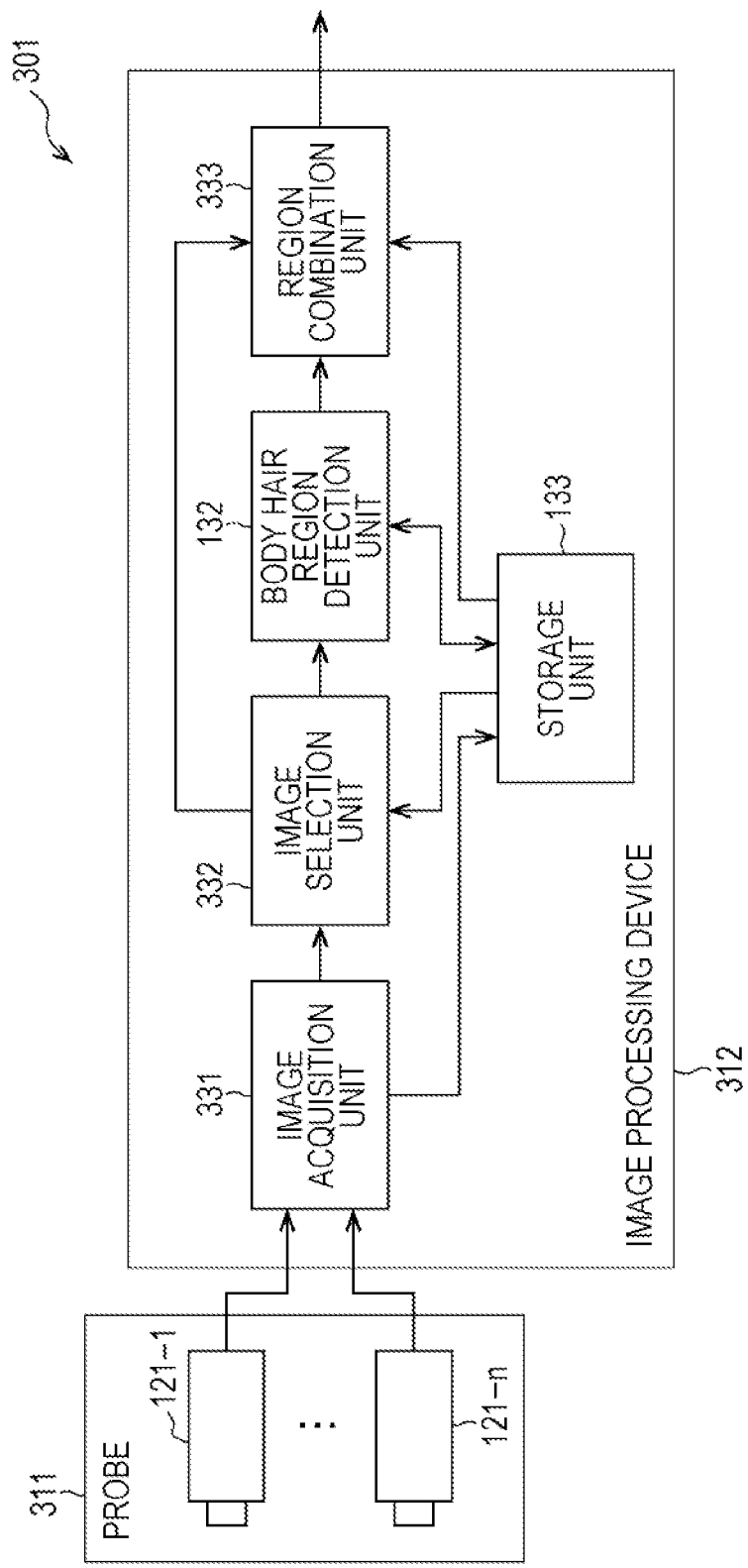
FIG. 18 is a block diagram showing a third embodiment of an image processing system to which the present technique is applied.

FIG. 18 is a block diagram showing an example of functional structure of an image processing system 301 as the third embodiment of an image processing system to which the present technique is applied. In the drawing, the components equivalent to those in FIG. 1 are denoted by the same reference numerals as those used in FIG. 1, and explanation of the components that perform the same processes as above is not repeated herein.

The image processing system 301 is designed to include a probe 311 and an image processing device 312.

The probe 311 differs from the probe 111 of FIG. 1 in the number of installed photographing devices 121. Specifically, n (n being three or greater) photographing devices 121-1 through 121-n are provided in the probe 311.

The photographing devices 121-1 through 121-n are placed inside the probe 311 so that the same region of the skin of a person can be photographed from different directions while a predetermined portion of the probe 311 is in contact with or proximity to the skin of the person. The photographing devices 121-1 through 121-n supply respective captured skin images to the image processing device 312.

The conditions for positioning the photographing devices 121-1 through 121-n are now described.

The photographing devices 121-1 through 121-n are positioned so that there is a region to be photographed by all the photographing devices. Any two of the photographing devices 121 are also positioned so as to differ from each other in at least the azimuth angle or the depression angle of the center line of the optical axis with reference to the surface of the skin of the person to be photographed. Accordingly, the same region of the skin of the person can be simultaneously photographed from different directions by any two photographing devices 121. Here, the center lines of the optical axes of any two photographing devices 121 do not necessarily intersect each other.

Figure 19:
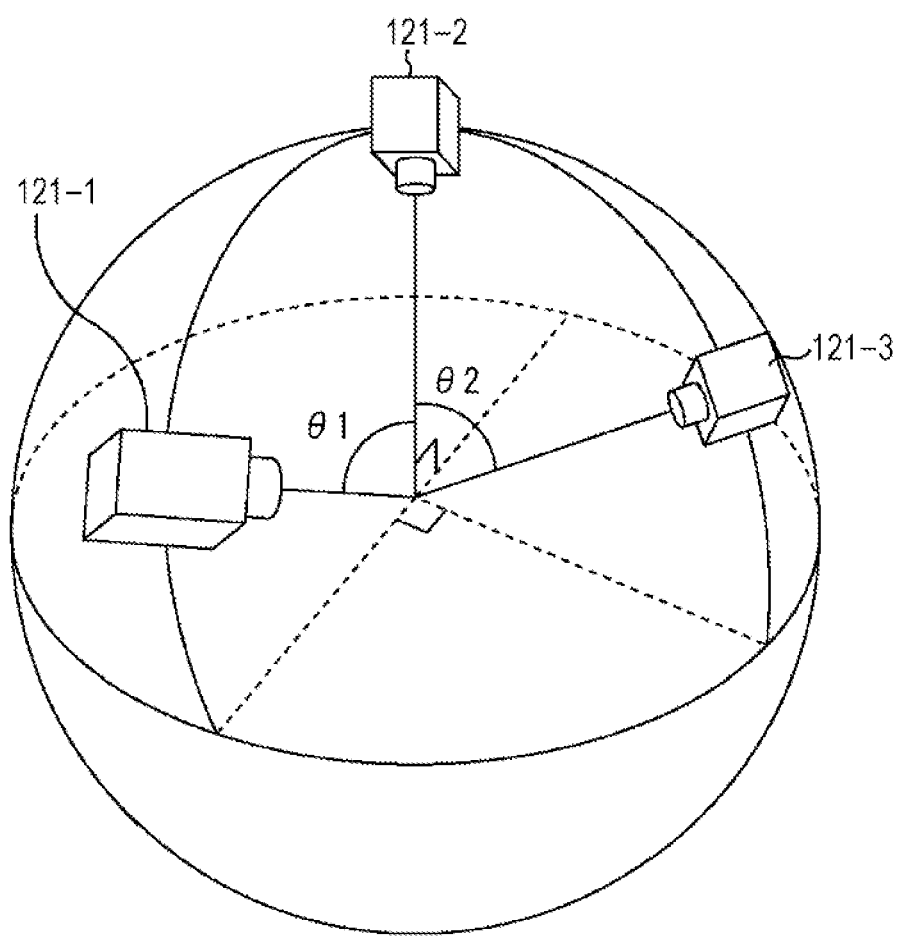
FIG. 19 is a diagram showing an example of ideal positioning of photographing devices in a case where photographing is performed from three directions.

FIG. 19 shows an example of ideal positioning in a case where three photographing devices 121 are used.

The photographing device 121-1 and the photographing device 121-2 are located in the same positions as those shown in FIG. 2. The center line of the optical axis of the photographing device 121-3 intersects with the center lines of the optical axes of the photographing device 121-1 and the photographing device 121-2 on the surface of the skin of a person, and is placed in a direction obliquely upward seen from the intersection point.

The center line of the optical axis of the photographing device 121-1 and the center line of the optical axis of the photographing device 121-3 differ from each other in azimuth angle by 90 degrees. Further, the angle θ1 between the center line of the optical axis of the photographing device 121-2 and the center line of the optical axis of the photographing device 121-1 is the same as the angle θ2 between the center line of the optical axis of the photographing device 121-2 and the center line of the optical axis of the photographing device 121-3.

Referring back to FIG. 18, the image processing device 312 differs from the image processing device 112 of FIG. 1 in that the image acquisition unit 131 is replaced with an image acquisition unit 331, and an image selection unit 332 and a region combination unit 333 are added.

The image acquisition unit 331 acquires skin images photographed by the photographing devices 121-1 through 121-*n*, and stores the skin images into the storage unit 133. The image acquisition unit 331 also notifies the image selection unit 332 of the acquisition of the skin images.

The image selection unit 332 selects two of the skin images stored in the storage unit 133 as the current images, and supplies the selected skin images to the body hair region detection unit 132. When the body hair regions in all the skin images have been detected, the image selection unit 332 notifies the region combination unit 333 to that effect.

The body hair region detection unit 132 detects body hair regions in the skin images selected by the image selection unit 332, and supplies information indicating the detection results to the region combination unit 333.

The region combination unit 333 selects, from the skin images stored in the storage unit 133, a skin image (hereinafter referred to as a detection object image) from which a body hair region is to be eventually detected. The region combination unit 333 calculates body hair regions formed by projecting the body hair regions detected from the respective skin images other than the detection object image onto the coordinate system of the detection object image. The region combination unit 333 further calculates an eventual body hair region by combining the body hair region in the detection object image and the body hair regions projected from the respective skin images onto the coordinate system of the detection object image. The region combination unit 333 then outputs the detection object image and the result of the detection of the eventual body hair region to a later stage.

[Image Processing by Image Processing System 301]

Figure 20:
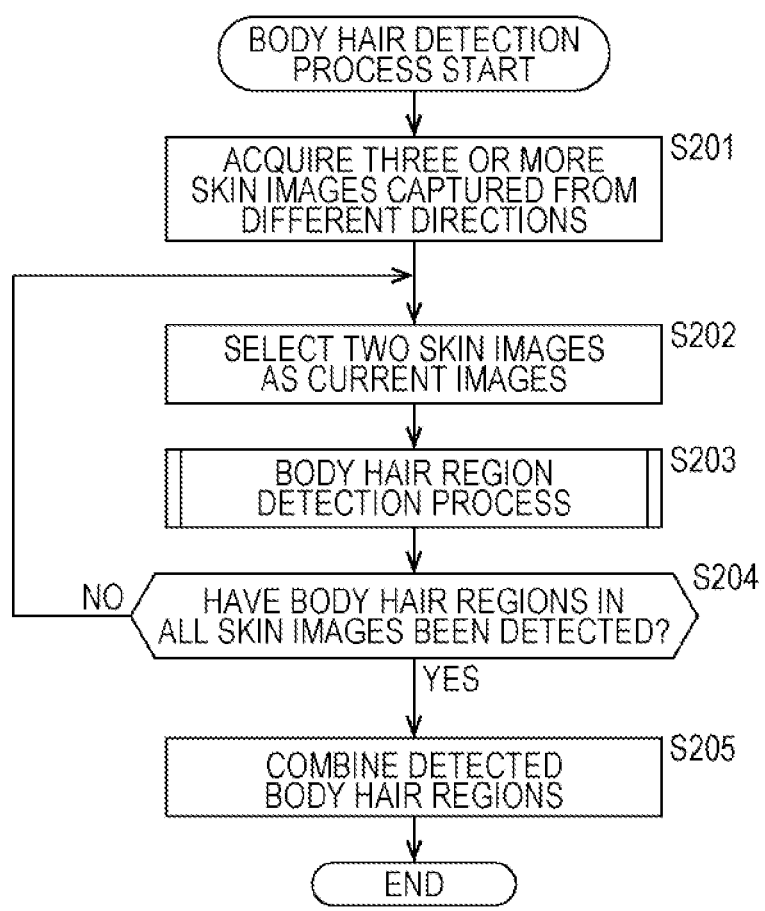
FIG. 20 is a flowchart for explaining a second embodiment of a body hair detection process.

Referring now to the flowchart shown in FIG. 20, the body hair detection process to be performed by the image processing system 301 is described.

Figure 21:
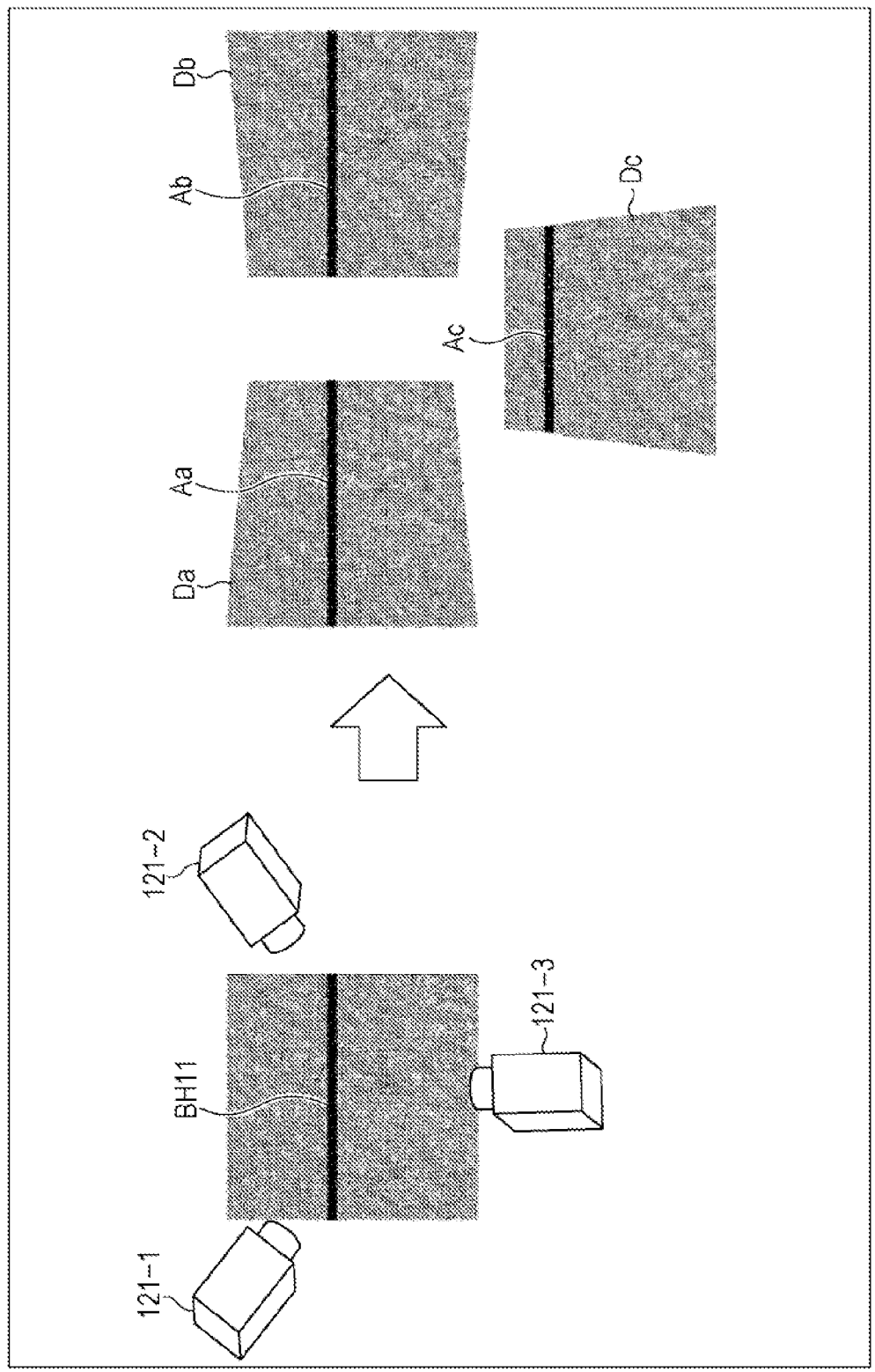
FIG. 21 is a diagram for explaining a specific example of the body hair detection process.

The following is a description of a process to be performed in a case where a region of the skin in which a body hair BH11 exists is photographed in an obliquely downward direction from the upper left by the photographing device 121-1, is photographed in an obliquely downward direction from the upper right by the photographing device 121-2, and is photographed in an obliquely downward from below by the photographing device 121-3, as shown in FIG. 21, appropriately accompanied with a specific example.

In step S201, the image processing system 301 acquires three or more skin images captured from different directions. Specifically, the photographing devices 121-1 through 121-*n* almost simultaneously photograph the skin of a person from different directions from one another. At this point, the photographing devices 121-1 through 121-*n* capture closeup images of the skin from short distances, with the probe 311 being in contact with or close proximity to the skin, for example. The photographing devices 121-1 through 121-*n* then supply the skin images obtained as a result of the photographing, to the image acquisition unit 331. The image acquisition unit 331 stores the acquired n skin images into the storage unit 133. The image acquisition unit 331 also notifies the image selection unit 332 of the acquisition of the skin images.

For example, as shown in FIG. 21, a skin image including an image Da is captured by the photographing device 121-1, a skin image including an image Db is captured by the photographing device 121-2, and a skin image including an image Dc is captured by the photographing device 121-3. The images Da through Dc are formed by extracting the portions corresponding to the same region of the skin from the respective skin images captured by the photographing devices 121-1 through 121-3.

In the images Da through Dc, there are respective body hair regions Aa through Ac each showing the body hair BH11. In those images, the skin region hidden by the body hair region Aa in the image Da is substantially the same as the skin region hidden by the body hair region Ab in the image Db. Meanwhile, the skin region hidden by the body hair region Aa in the image Da differs from the skin region hidden by the body hair region Ac in the image Dc. Likewise, the skin region hidden by the body hair region Ab in the image Db differs from the skin region hidden by the body hair region Ac in the image Dc.

In the following, a case where processing is performed on the images Da through Dc will be appropriately described as a specific example where appropriate.

In step S202, the image selection unit 332 selects two skin images as current images. Specifically, the image selection unit 332 selects, from the skin images stored in the storage unit 133, one skin image from which any body hair region has not been detected yet, as the projection destination image. The image selection unit 332 also selects one of the remaining skin images as the projection original image. At this point, it is preferable to select the projection original image so that the resultant combination is not the same as any of the combinations of skin images selected in the past. The image selection unit 332 then supplies the selected projection original image and projection destination image to the feature point detection unit 151 of the body hair region detection unit 132.

In step S203, a body hair region detection process is performed by using the selected projection original image and projection destination image, as in the procedure of step S2 in FIG. 5. As a result, the body hair region in the projection destination image is detected. The region detection unit 156 of the body hair region detection unit 132 supplies information indicating the results of the body hair region detection to the region combination unit 333.

In step S204, the image selection unit 332 determines whether the body hair regions in all the skin images have been detected. If it is determined that there is a skin image from which any body hair region has not been detected yet, the process returns to step S202.

After that, the procedures of steps S202 through S204 are repeated until it is determined in step S204 that the body hair regions in all the skin images have been detected. In this manner, the body hair regions in all the skin images are detected.

Figure 22:
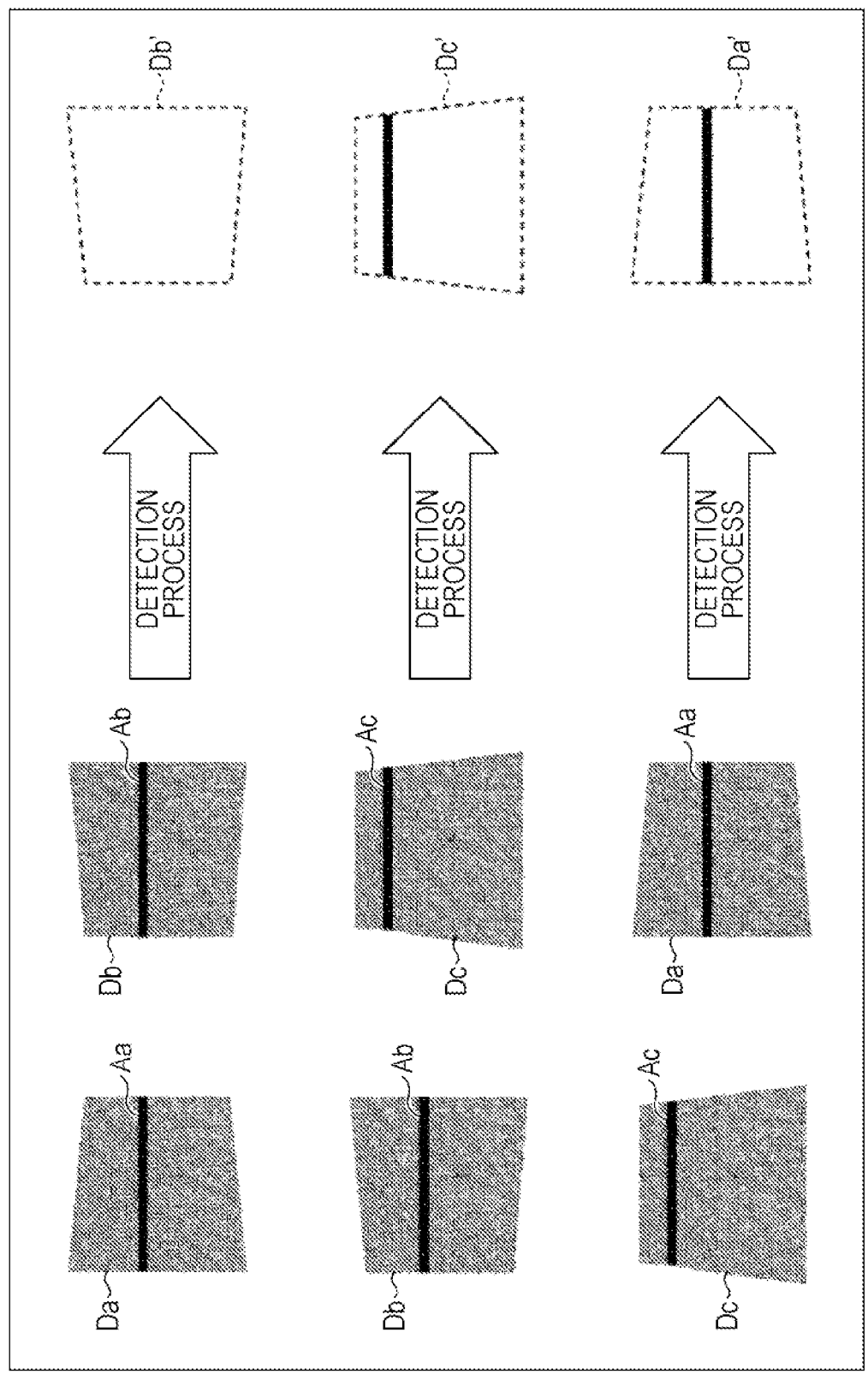
FIG. 22 is a diagram for explaining a specific example of the body hair detection process.

For example, as shown in FIG. 22, the image Da is set as the projection original image, the image Db is set as the projection destination image, and the body hair region in the image Db is detected. Likewise, the image Db is set as the projection original image, the image Dc is set as the projection destination image, and the body hair region in the image Dc is detected. The image Dc is set as the projection original image, the image Da is set as the projection destination image, and the body hair region in the image Da is detected.

An image Da', an image Db', and an image Dc' in FIG. 22 are the results of the detection of the body hair regions in the image Da, the image Db, and the image Dc. In this example, the body hair region Aa in the image Da overlaps the body hair region Ab in the image Db. Therefore, the body hair region in the image Db is not detected.

If it is determined in step S204 that the body hair regions in all the skin images have been detected, on the other hand, the process moves on to step S205. At this point, the image selection unit 332 notifies the region combination unit 333 that the body hair regions in all the skin images have been detected.

In step S205, the region combination unit 333 combines the detected body hair regions. Specifically, the region combination unit 333 selects a detection object image from the skin images stored in the storage unit 133. Using the homography matrix for projecting the respective skin images onto the coordinate system of the detection object image, the region combination unit 333 calculates the body hair regions obtained by projecting the detection object image of the respective skin images onto the coordinate system of the detection object image.

The homography matrix for projecting the respective skin images onto the coordinate system of the detection object image may be the homography matrix that has been used in a body hair region detection process and is stored in the storage unit 133, if any. If there is no homography matrix stored in the storage unit 133, on the other hand, a homography matrix is calculated by the above described method using the feature points in the regions other than the body hair region, for example.

The region combination unit 333 then calculates an eventual body hair region by combining (or joining) the body hair region in the detection object image and the body hair regions projected from the respective skin images onto the coordinate system of the detection object image. That is, the region formed by superimposing the body hair regions detected from the respective skin images one another is determined to be the eventual body hair region.

Figure 23:
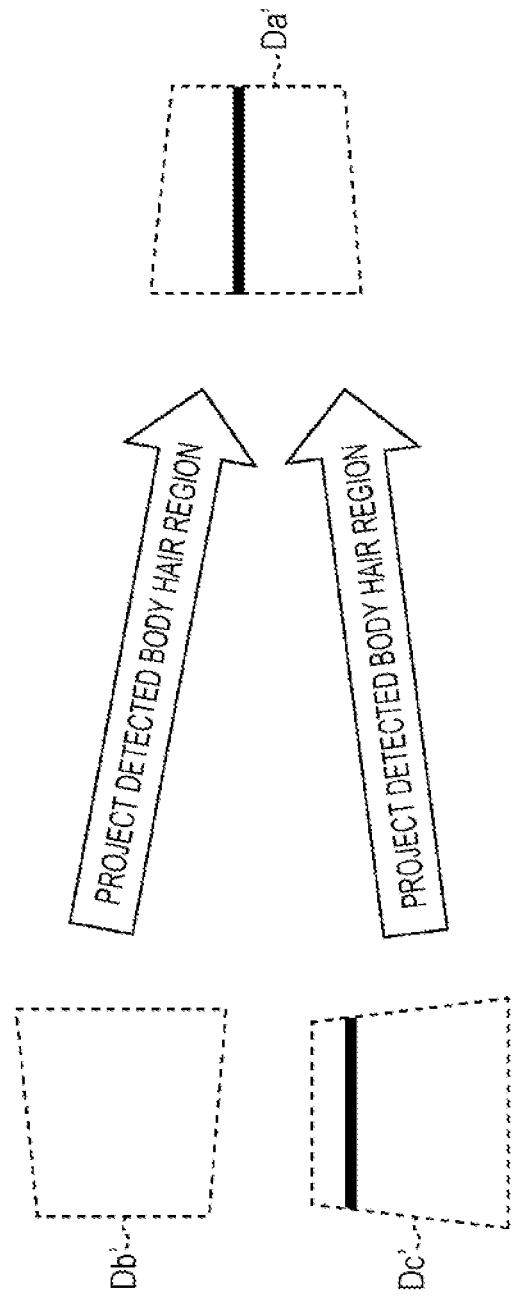
FIG. 23 is a diagram for explaining a method of combining body hair regions.

For example, as shown in FIG. 23, the body hair region detected in the image Db and the body hair region detected in the image Dc are projected onto the coordinate system of the image Da, and the region formed by superimposing the respective body hair regions on one another is determined to be the eventual body hair region.

The region combination unit 333 then outputs the detection object image and the result of the detection of the eventual body hair region to a later stage.

In the above described manner, body hair regions in skin images can be more accurately detected.

<4. Fourth Embodiment>

Figure 24:
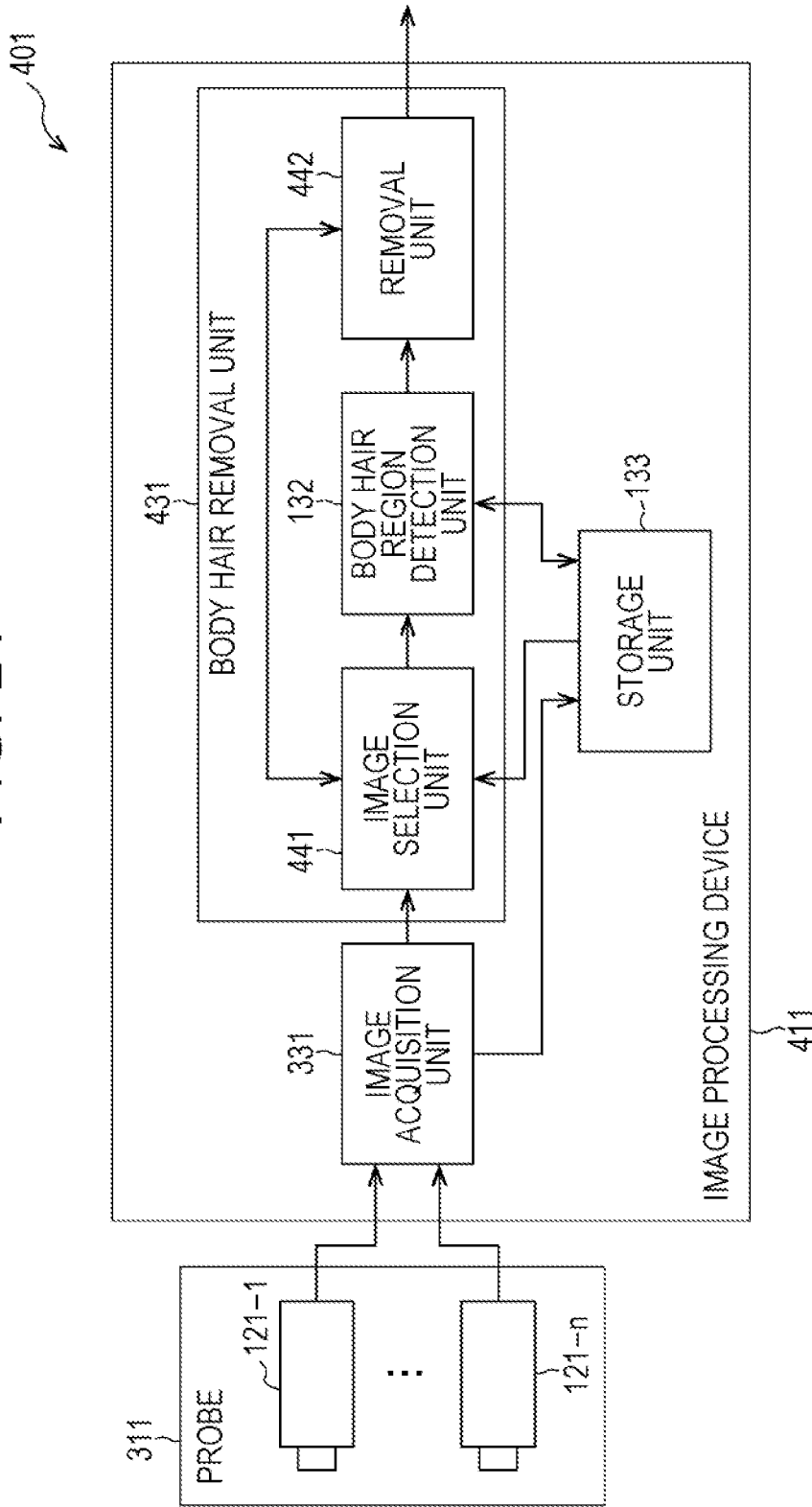
FIG. 24 is a block diagram showing a fourth embodiment of an image processing system to which the present technique is applied.
Figure 25:
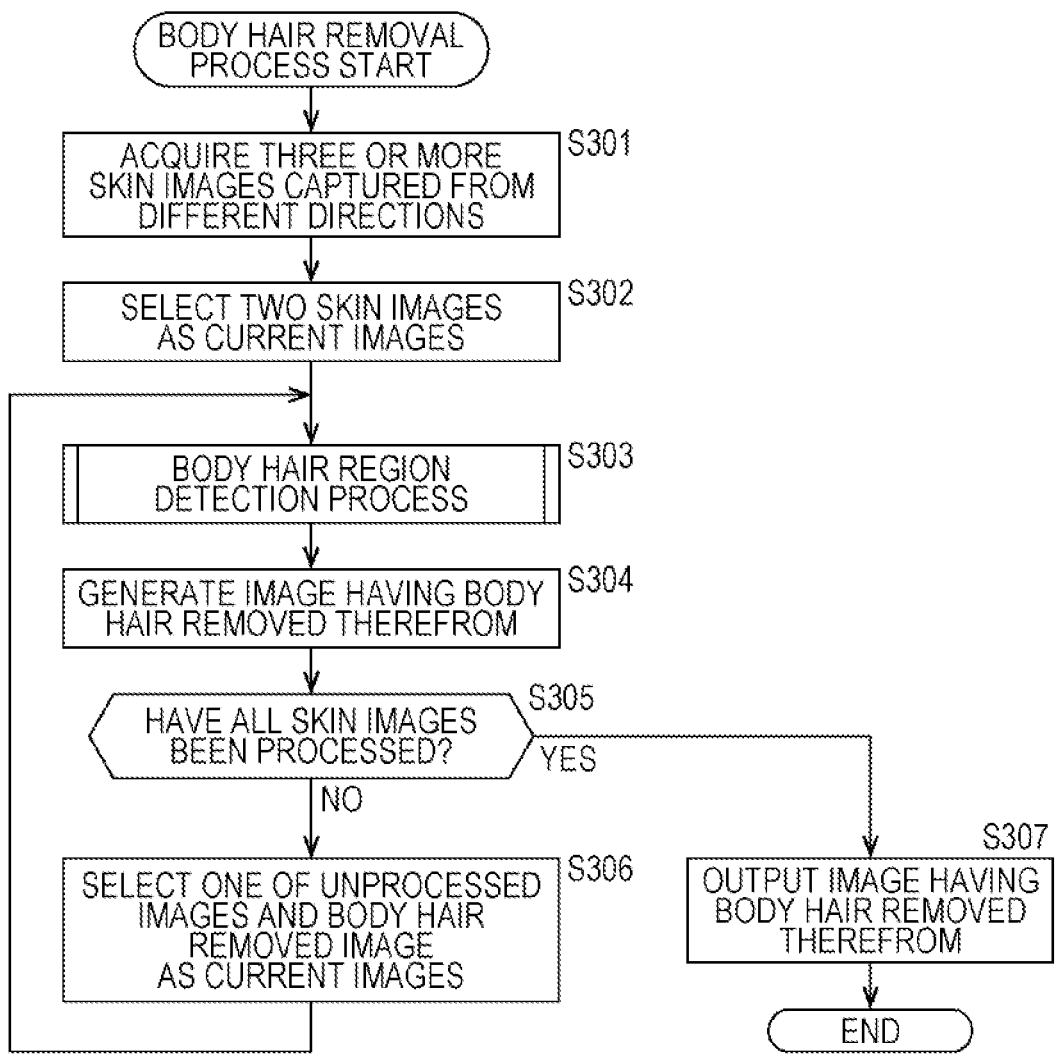
FIG. 25 is a flowchart for explaining a second embodiment of a body hair removal process.

Referring now to FIGS. 24 and 25, a fourth embodiment of the present technique is described. In the fourth embodiment of the present technique, a body hair is removed from skin images by using three or more skin images acquired by photographing the skin from three or more different directions.

[Structure Example of Image Processing System 401]

FIG. 24 is a block diagram showing an example of functional structure of an image processing system 401 as the fourth embodiment of an image processing system to which the present technique is applied. In the drawing, the components equivalent to those in FIG. 13 or 18 are denoted by the same reference numerals as those used in FIG. 13 or 18, and explanation of the components that perform the same processes as above is not repeated herein.

The image processing system 401 differs from the image processing system 201 of FIG. 13 in that the probe 111 is replaced with the same probe 311 as that of the image processing system 301 shown in FIG. 18, and the image processing device 211 is replaced with an image processing device 411. The image processing device 411 differs from the image processing device 211 in that the image acquisition unit 131 is replaced with the same image acquisition unit 331 as that of the image processing system 301 shown in FIG. 18, and the body hair removal unit 231 is replaced with a body hair removal unit 431. The body hair removal unit 431 differs from the body hair removal unit 231 in that the removal unit 241 is replaced with a removal unit 442, and an image selection unit 441 is added.

The image selection unit 441 first selects two of the skin images stored in the storage unit 133 as the current images, and supplies the selected skin images to the body hair region detection unit 132. Thereafter, the image selection unit 441 selects one of the unprocessed images stored in the storage unit 133 and a body-hair removed image supplied from the removal unit 442 as current images, and supplies the selected images to the body hair region detection unit 132. When the body hair regions in all the skin images have been detected, the image selection unit 441 notifies the removal unit 442 to that effect.

Based on the result of body hair region detection by the body hair region detection unit 132, the removal unit 442 generates a body-hair removed image that is a skin image having the body hair removed therefrom. The removal unit 442 supplies the generated body-hair removed image to the image selection unit 441, or outputs the generated body-hair removed image to a later stage.

[Image Processing by Image Processing System 401]

Referring now to the flowchart shown in FIG. 25, the body hair removal process to be performed by the image processing system 401 is described.

In step S301, three or more skin images captured from different directions are acquired, as in the procedure of step S201 in FIG. 20.

In step S302, the image selection unit 441 selects two skin images as current images. Specifically, the image selection unit 441 selects any two skin images from the skin images stored in the storage unit 133, and sets one of the two skin images as the projection original image and the other one as the projection destination image. The image selection unit 332 then supplies the selected projection original image and projection destination image to the feature point detection unit 151 of the body hair region detection unit 132.

In step S303, a body hair region detection process is performed by using the selected projection original image and projection destination image, as in the procedure of step S2 in FIG. 5. As a result, the body hair region in the projection destination image is detected.

In step S304, the removal unit 442 generates an image (a body-hair removed image) that is the projection destination image having the body hair removed therefrom, as in the procedure of step S103 in FIG. 14. The removal unit 442 supplies the generated body-hair removed image to the image selection unit 441.

In step S305, the image selection unit 441 determines whether all the skin images have been processed. If it is determined that there is a skin image yet to be processed, the process moves on to step S306.

In step S306, the image selection unit 441 selects one of the unprocessed skin images and the body-hair removed image as the current images. Specifically, the image selection unit 441 selects one of the unprocessed skin images stored in the storage unit 133 as the projection original image. The image selection unit 441 also selects the body-hair removed image supplied from the removal unit 442 as the projection destination image. The image selection unit 332 then supplies the selected projection original image and projection destination image to the feature point detection unit 151 of the body hair region detection unit 132.

After that, the process returns to step S303, and the procedures of steps S303 through S306 are repeated until it is determined in step S305 that all the skin images have been processed. That is, the following process is repeated: a body-hair removed image is newly generated by setting one of the unprocessed skin images as the projection original image and a newly generated body-hair removed image as the projection destination image, and removing the body hair from the body-hair removed image as the projection destination image.

If it is determined in step S305 that all the skin images have been processed, on the other hand, the process moves on to step S307. At this point, the image selection unit 441 notifies the removal unit 442 that all the skin images have been processed.

In step S307, the removal unit 442 outputs the image having the body hair removed therefrom. That is, the removal unit 442 outputs the latest body-hair removed image to a later stage.

An example case where a body-hair removed image is generated by using the images Da through Dc shown in FIG. 21 is now described. First, the image Da is set as the projection original image, and the image Db is set as the projection destination image. A body-hair removed image Db' (not shown) formed by removing the body hair from the image Db is then generated. Next, the image Dc is set as the projection original image, and the body-hair removed image Db' is set as the projection destination image. A body-hair removed image Db" formed by further removing the body hair from the body-hair removed image Db' is generated. The body-hair removed image Db" is output to a later stage.

In the above manner, a body hair can be more certainly removed from skin images.

<5. Fifth Embodiment>

Referring now to FIGS. 26 through 29, a fifth embodiment of the present technique is described. In the fifth embodiment of the present technique, an image from which a body hair has been removed is generated by using a skin image obtained by photographing the skin from different directions with one photographing device and a mirror.

[Structure Example of Image Processing System 501]

Figure 26:
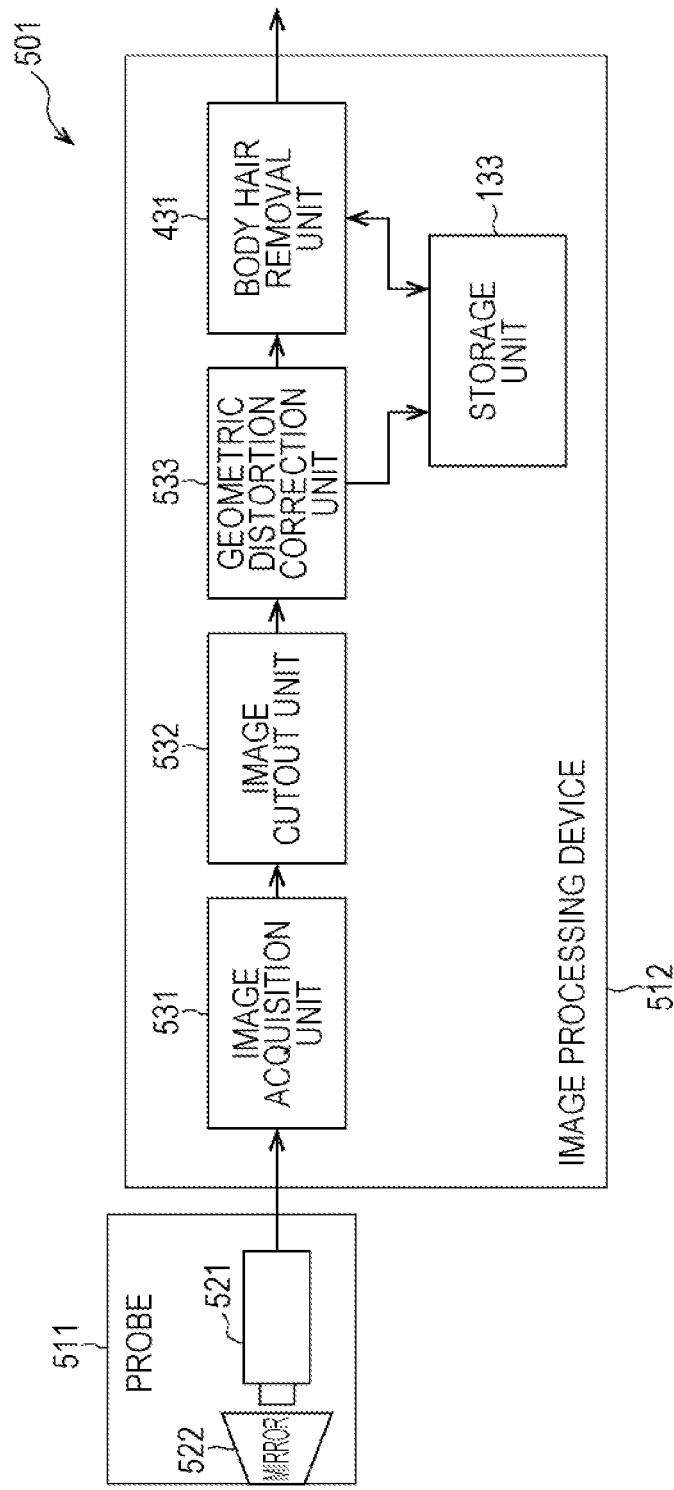
FIG. 26 is a block diagram showing a fifth embodiment of an image processing system to which the present technique is applied.

FIG. 26 is a block diagram showing an example of functional structure of an image processing system 501 as the fifth embodiment of an image processing system to which the present technique is applied. In the drawing, the components equivalent to those in FIG. 24 are denoted by the same reference numerals as those used in FIG. 24, and explanation of the components that perform the same processes as above is not repeated herein.

The image processing system 501 is designed to include a probe 511 and an image processing device 512.

The probe 511 is designed to include a photographing device 521 and a mirror 522.

Figure 27:
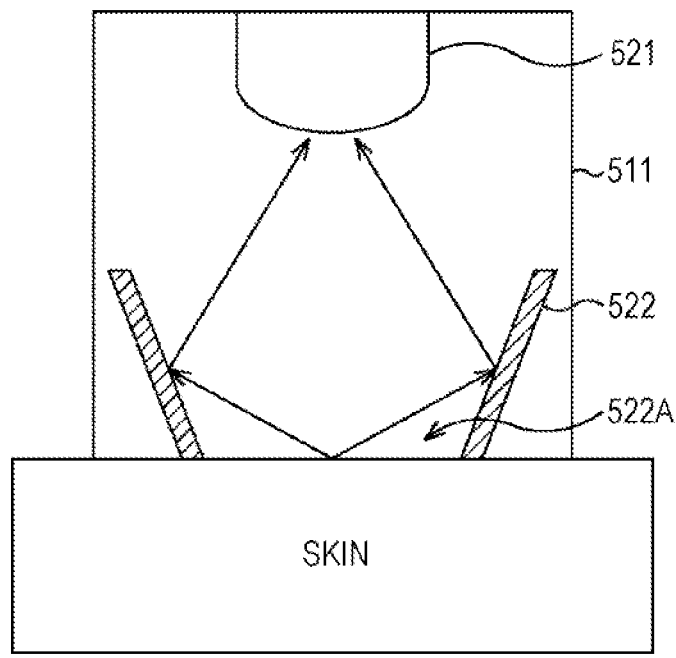
FIG. 27 is a schematic diagram showing an example structure of a probe.

FIG. 27 is a schematic view of the probe 511 seen from the side.

The mirror 522 has a cylindrical shape like a truncated cone having its side surface upside down, and a mirror is provided therein. The region of the skin to be photographed is put into an opening 522A of the mirror 522, and the photographing device 521 captures skin images, with the probe 511 being in contact with or proximity to the skin of the person while the region is radially surrounded by the mirror 522.

The photographing device 521 is formed with a wide-angle photographing device using a fisheye lens or the like. The photographing device 521 photographs the skin reflected in the mirror 522, to obtain an image of the region of the skin seen from every angle throughout 360 degrees in the opening 522A. The photographing device 521 supplies the captured skin image to the image processing device 512.

The image processing device 512 differs from the image processing device 411 of FIG. 24 in that the image acquisition unit 331 is replaced with an image acquisition unit 531, and an image cutout unit 532 and a geometric distortion correction unit 533 are included.

The image acquisition unit 531 acquires the skin image captured by the photographing device 521, and supplies the skin image to the image cutout unit 532.

The image cutout unit 532 cuts out images of the skin reflected in the mirror 522 from the skin image by a predetermined width and a predetermined cutout width. The image cutout unit 532 supplies the skin images obtained as a result to the geometric distortion correction unit 533.

The geometric distortion correction unit 533 performs geometric distortion correction on the respective skin images supplied from the image cutout unit 532, and stores the corrected skin images into the storage unit 133. The geometric distortion correction unit 533 also notifies the image selection unit 441 of the body hair removal unit 431 that the skin images have been acquired.

[Image Processing by Image Processing System 501]

Figure 28:
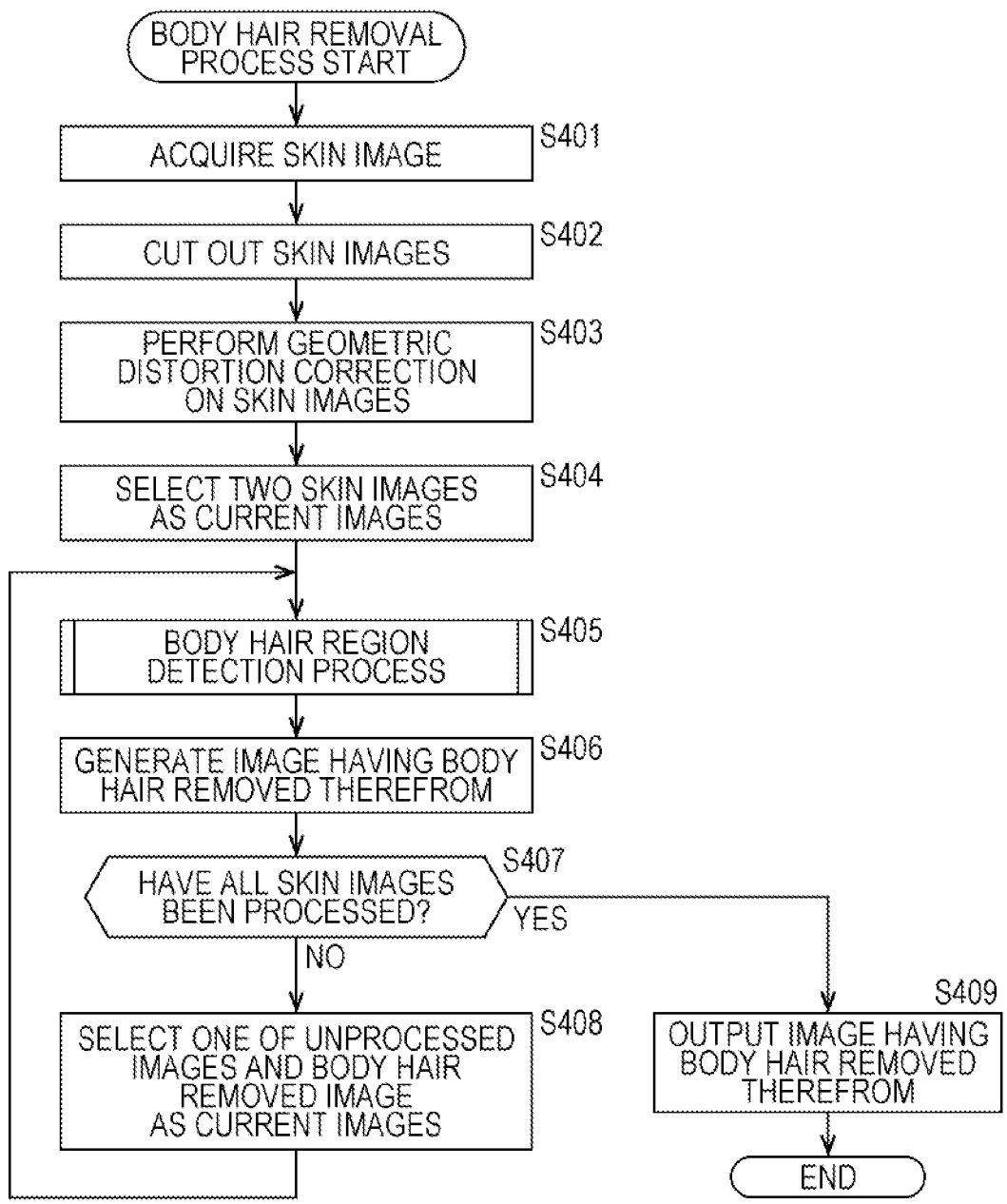
FIG. 28 is a flowchart for explaining a third embodiment of a body hair removal process.

Referring now to the flowchart shown in FIG. 28, the body hair removal process to be performed by the image processing system 501 is described.

In step S401, the image processing system 501 acquires a skin image. Specifically, the photographing device 521 photographs the skin of a person reflected in the mirror 522. At this point, the photographing device 521 captures a closeup image of the skin reflected in the mirror 522 from a short distance, with the probe 511 being in contact with or close proximity to the skin, for example. The photographing device 521 then supplies the skin image obtained as a result of the photographing, to the image acquisition unit 531. The image acquisition unit 531 supplies the acquired skin image to the image cutout unit 532.

Figure 29:
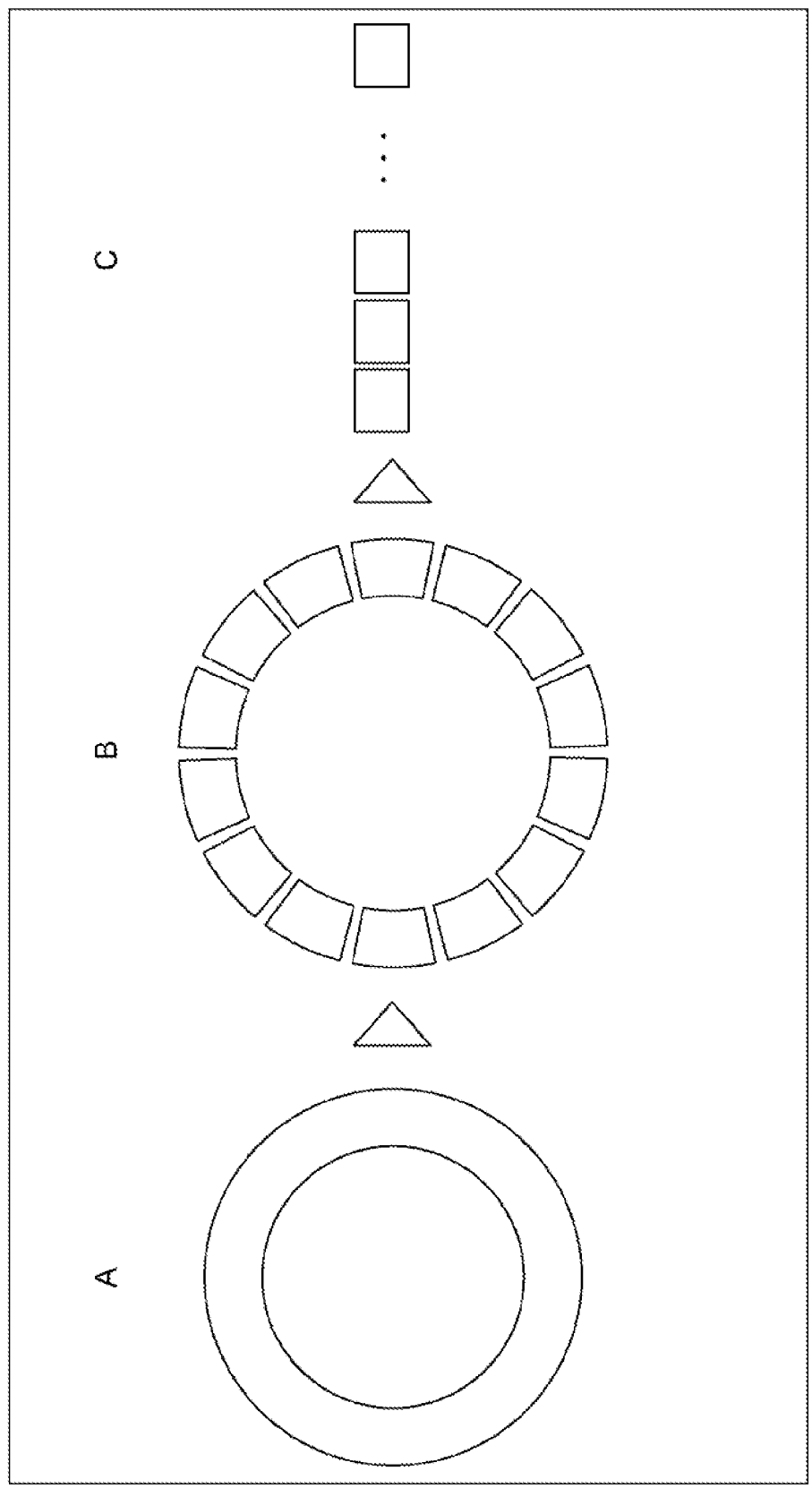
FIG. 29 is a diagram for explaining a method of generating skin images.

As the skin reflected in the mirror 522 is photographed, the skin image obtained at this point includes a ring-shaped (doughnut-shaped) image (hereinafter referred to as a ring-shaped image) of the same skin region seen from every angle throughout 360 degrees, as shown in A of FIG. 29.

In step S402, the image cutout unit 532 cuts out skin images. Specifically, as shown in B of FIG. 29, the image cutout unit 532 cuts out skin images from the ring-shaped image in the skin image by a predetermined width at predetermined intervals. The image cutout unit 532 then supplies the cut-out skin images to the geometric distortion correction unit 533.

At this point, there is no need to cut out all the regions in the ring-shaped image. For example, skin images may be cut out from the ring-shaped image at appropriate intervals, or skin images may be cut out from a part of a region in the ring-shaped image. Skin images may also be cut out so that the regions of adjacent skin images partially overlap with each other in terms of image processing, for example.

In step S403, the geometric distortion correction unit 533 performs geometric distortion correction on the skin images. Specifically, the geometric distortion correction unit 533 performs geometric distortion correction, such as distortion correction, affine transform, or projective transform, on the respective skin images cut out by the image cutout unit 532. As a result, the flat images of the skin shown in C of FIG. 29 are generated from the skin images shown in B of FIG. 29. The geometric distortion correction unit 533 stores the corrected skin images into the storage unit 133. The geometric distortion correction unit 533 also notifies the image selection unit 441 of the body hair removal unit 431 that the skin images have been acquired.

After that, in steps S404 through S409, the same procedures as those of steps S302 through S307 in FIG. 25 are carried out, and a body-hair removed image formed by removing the body hair from the skin image is generated and is output to a later stage.

In the above manner, an image formed by removing a body hair from skin images can be obtained without the use of a plurality of photographing devices.

The probe 511 may be applied to the image processing system 301 of FIG. 18, and body hair regions can be detected by using a ring-shaped image captured by the probe 511.

The mirror 522 does not necessarily have such a shape as to surround a skin region throughout 360 degrees, and may have such as shape as to surround only part of a skin region.

<6. Sixth Embodiment>

Figure 30:
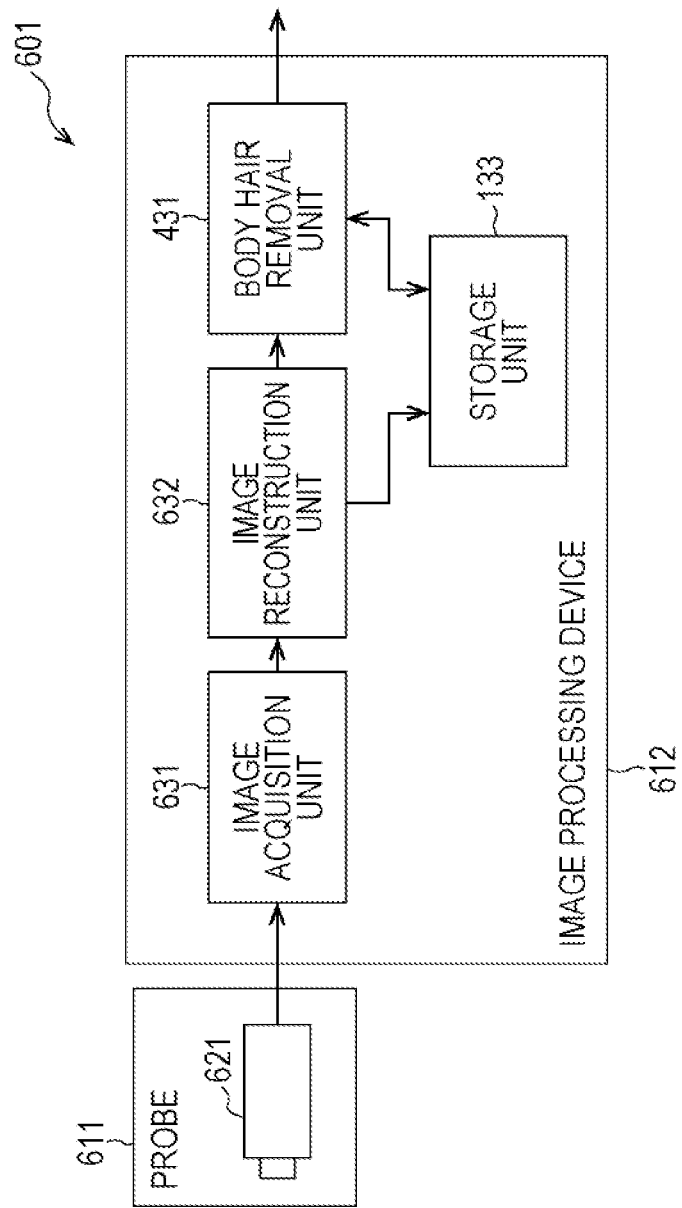
FIG. 30 is a block diagram showing a sixth embodiment of an image processing system to which the present technique is applied.
Figure 31:
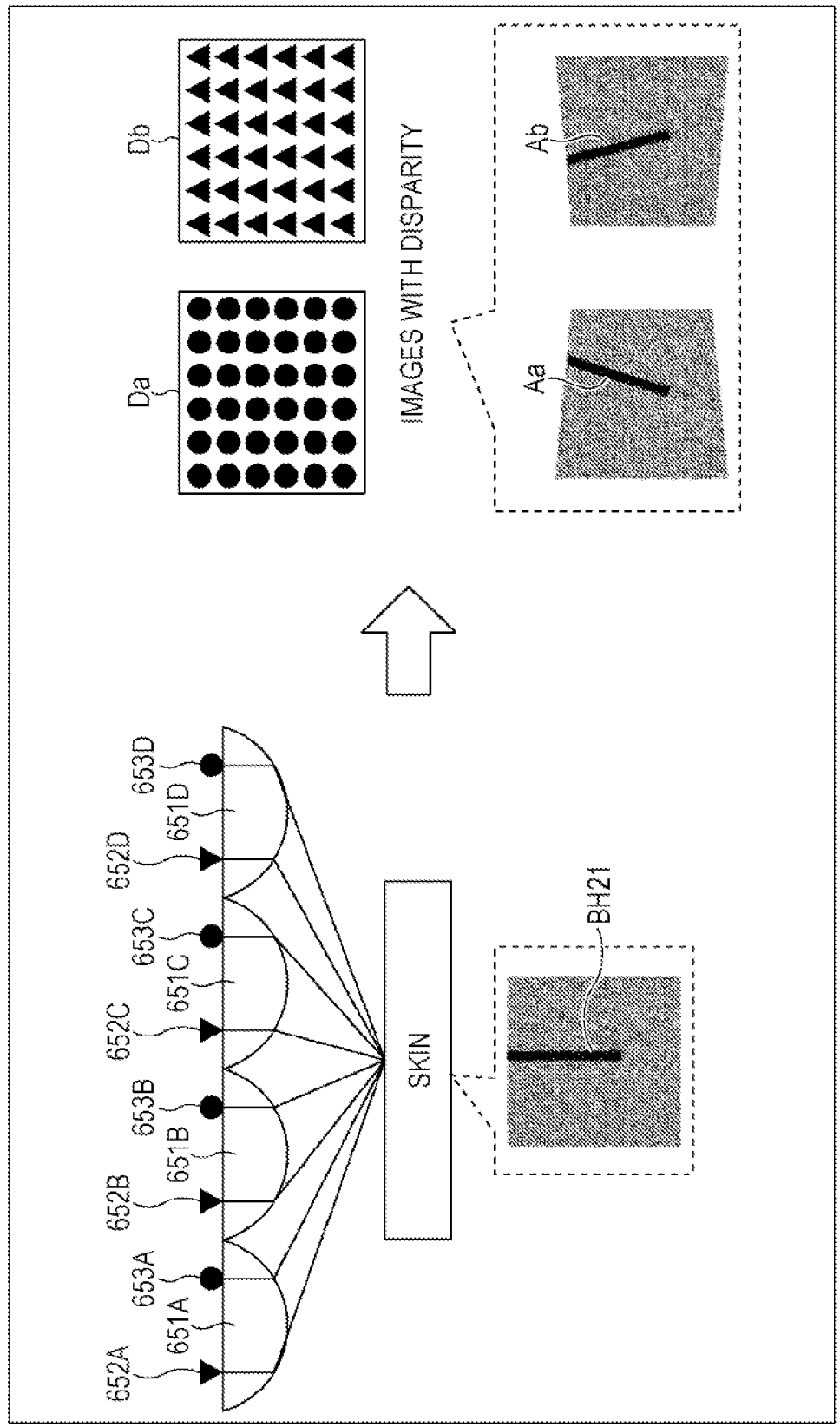
FIG. 31 is a diagram for explaining an example of positioning of microlenses and imaging elements, and a method of reconstructing skin images.
Figure 32:
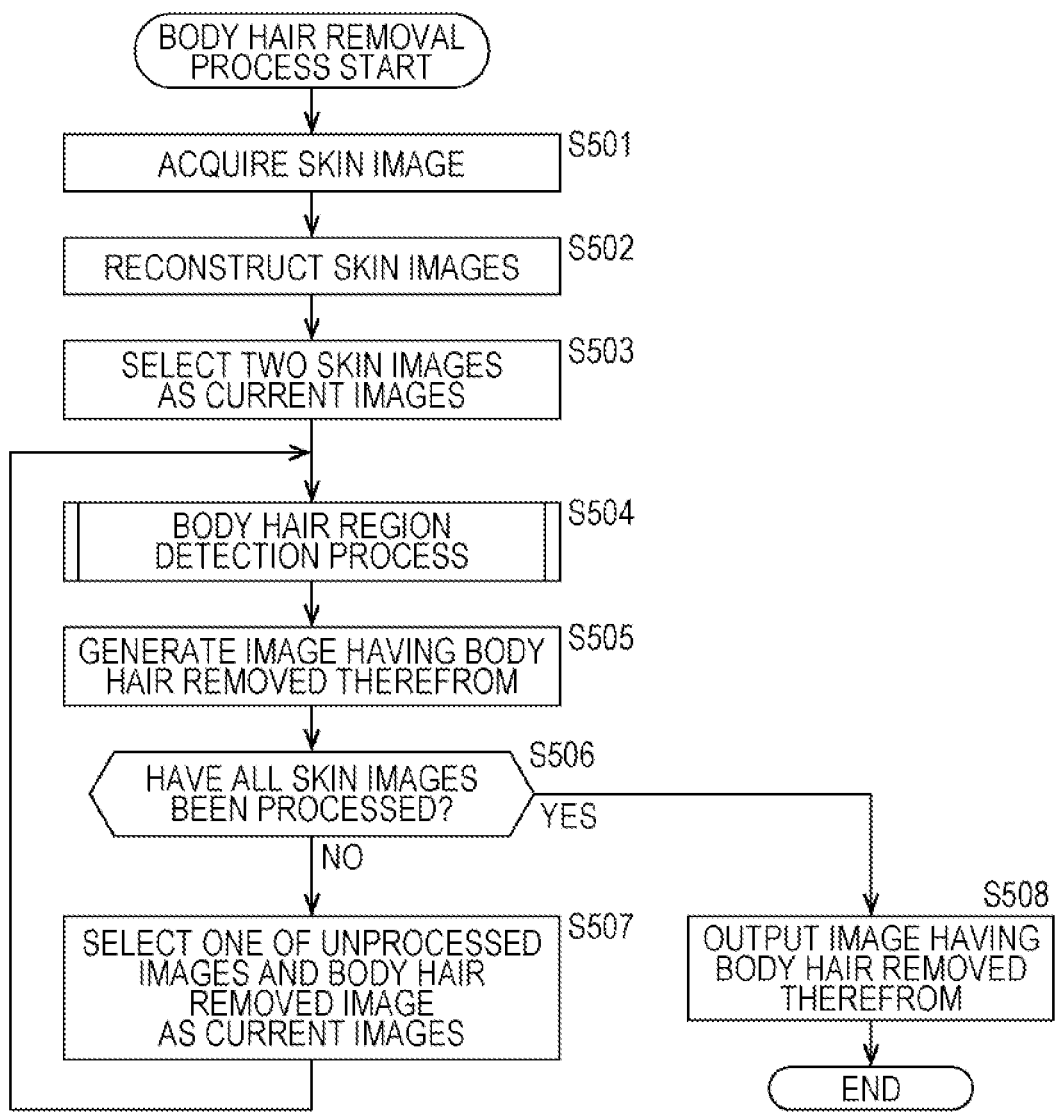
FIG. 32 is a flowchart for explaining a fourth embodiment of a body hair removal process.

Referring now to FIGS. 30 through 32, a sixth embodiment of the present technique is described. In the sixth embodiment of the present technique, an image from which a body hair has been removed is generated by using a skin image obtained by photographing the skin from different directions with one photographing device using a MLA (Micro Lens Array) technique.

[Structure Example of Image Processing System 601]

FIG. 30 is a block diagram showing an example of functional structure of an image processing system 601 as the sixth embodiment of an image processing system to which the present technique is applied. In the drawing, the components equivalent to those in FIG. 26 are denoted by the same reference numerals as those used in FIG. 26, and explanation of the components that perform the same processes as above is not repeated herein.

The image processing system 601 is designed to include a probe 611 and an image processing device 612.

The probe 611 is designed to include a photographing device 621 that uses the MLA technique. In the photographing device 621, microlenses are arranged in a lattice-like pattern, and imaging elements are arranged in a lattice-like pattern so that the imaging elements are provided for one microlens.

The diagram in the left side of FIG. 31 schematically shows an example array of microlenses and imaging elements.

Imaging elements 652A through 652D and imaging elements 653A through 653D are provided for microlenses 651A through 651D, respectively, which are aligned in the transverse direction. The imaging elements 652A through 652D are arranged so that the positions thereof relative to the microlenses 651A through 651D are the same. Also, the imaging elements 653A through 653D are arranged in different positions from the positions of the imaging elements 652A through 652D so that the positions thereof relative to the microlenses 651A through 651D are the same.

Hereinafter, the microlenses 651A through 651D will be referred to simply as the microlenses 651 when there is no need to distinguish them from one another. Also, hereinafter, the imaging elements 652A through 652D will be referred to simply as the imaging elements 652 when there is no need to distinguish them from one another, and the imaging elements 653A through 653D will be referred to simply as the imaging elements 653 when there is no need to distinguish them from one another.

Although only part of the arrangement is shown in this drawing, the microlenses 651, the imaging elements 652, and the imaging elements 653 are arranged in a lattice-like pattern, with uniform positional relationships being maintained among them.

The photographing device 621 then supplies a captured skin image to the image acquisition unit 631.

The image acquisition unit 631 supplies the skin image captured by the photographing device 621 to an image reconstruction unit 632.

The image reconstruction unit 632 classifies the respective pixels in the skin image into pixel groups corresponding to the imaging elements and gathers, to generate skin images. For example, as shown in FIG. 31, an image Da formed by gathering the pixels corresponding to the group of the imaging elements 652, and an image Db formed by gathering the pixels corresponding to the group of the imaging elements 653 are generated. The image Da and the image Db are images with a disparity as if the same region of the skin were seen from two different directions. Therefore, when a region of the skin in which a body hair BH21 exists is photographed, the skin region hidden by a body hair region Aa in the image Da differs from the skin region hidden by a body hair region Ab in the image Db, as in a case where the same skin region is photographed from different directions by two photographing devices.

The skin photographing directions can be changed by changing the positions of the imaging elements relative to the microlenses. Also, the number of skin photographing directions can be increased by increasing the number of imaging elements provided for one microlens.

The image reconstruction unit 632 then stores the generated skin images into the storage unit 133. The image reconstruction unit 632 also notifies the image selection unit 441 of the body hair removal unit 431 that the skin images have been acquired.

[Image Processing by Image Processing System 601]

Referring now to the flowchart shown in FIG. 32, the body hair removal process to be performed by the image processing system 601 is described.

In step S501, the image processing system 601 acquires a skin image. Specifically, the photographing device 621 photographs the skin of a person. At this point, the photographing device 621 captures a closeup image of the skin from a short distance, with the probe 611 being in contact with or close proximity to the skin, for example. The photographing device 621 then supplies the skin image obtained as a result of the photographing, to the image acquisition unit 631. The image acquisition unit 631 supplies the acquired skin image to an image reconstruction unit 632.

In step S502, the image reconstruction unit 632 reconstructs skin images. Specifically, the image reconstruction unit 632 classifies the pixels in the skin image captured by the photographing device 621 into the respective groups of the imaging elements that have performed the photographing and gathering, and generates skin images captured from different directions. The image reconstruction unit 632 then stores the generated skin images into the storage unit 133. The image reconstruction unit 632 also notifies the image selection unit 441 of the body hair removal unit 431 that the skin images have been acquired.

After that, in steps S503 through S508, the same procedures as those of steps S302 through S307 in FIG. 25 are carried out, and an image formed by removing the body hair from the skin image is generated.

In the above manner, an image formed by removing a body hair from skin images can be obtained without the use of the plurality of photographing devices.

The probe 611 may be applied to the image processing system 301 of FIG. 18, and body hair regions can be detected by using a skin image captured by the probe 611.

<7. Seventh Embodiment>

Referring now to FIGS. 33 through 37, a seventh embodiment of the present technique is described. In the seventh embodiment of the present technique, a cosmetic analysis function for analyzing skin conditions is added to the image processing system 601 of FIG. 30.

[Structure Example of Image Processing System 701]

Figure 33:
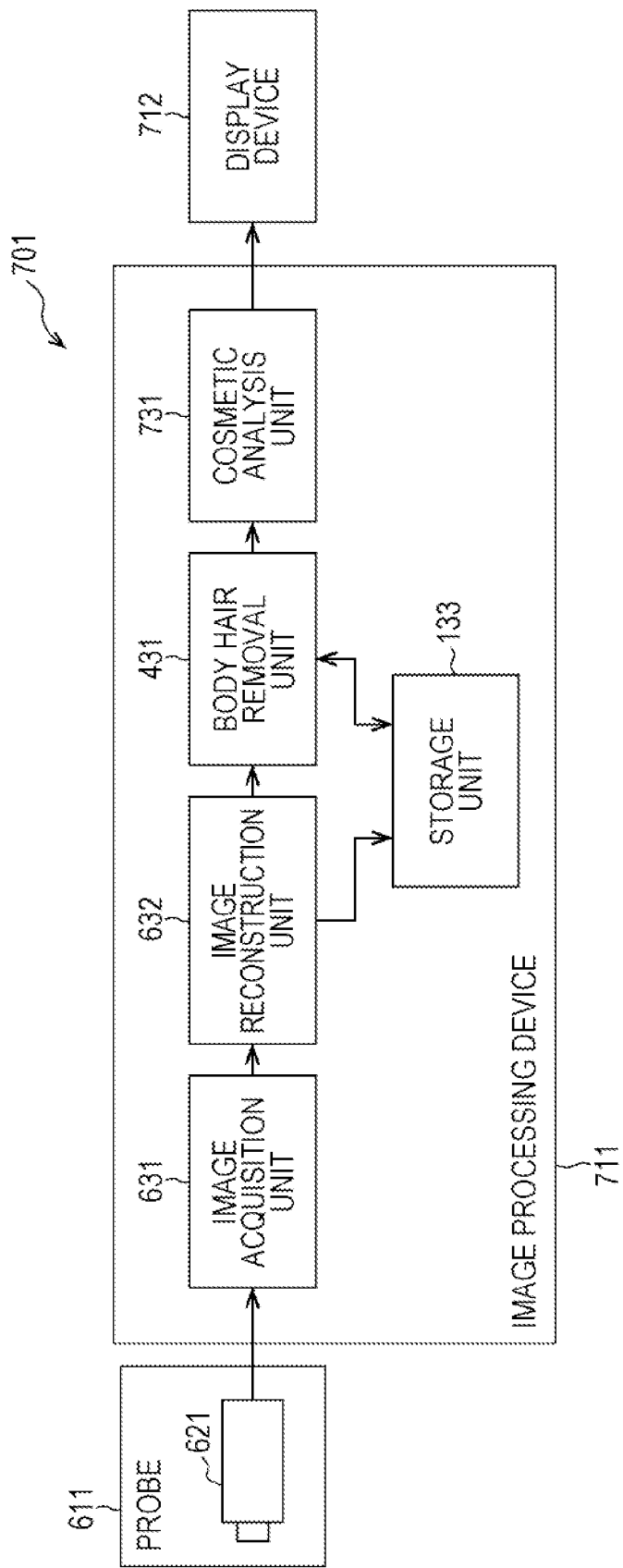
FIG. 33 is a block diagram showing a seventh embodiment of an image processing system to which the present technique is applied.

FIG. 33 is a block diagram showing an example of functional structure of an image processing system 701 as the seventh embodiment of an image processing system to which the present technique is applied. In the drawing, the components equivalent to those in FIG. 30 are denoted by the same reference numerals as those used in FIG. 30, and explanation of the components that perform the same processes as above is not repeated herein.

The image processing system 701 differs from the image processing system 601 of FIG. 30 in that the image processing device 612 is replaced with an image processing device 711, and a display device 712 is added. The image processing device 711 differs from the image processing device 612 in further including a cosmetic analysis unit 731.

The cosmetic analysis unit 731 analyzes a person's skin condition based on a body-hair removed image supplied from the body hair removal unit 431. The cosmetic analysis unit 731 supplies information indicating the result of the analysis to the display device 712.

The display device 712 displays the result of the analysis of the person's skin condition.

[Structure Example of Cosmetic Analysis Unit 731]

Figure 34:
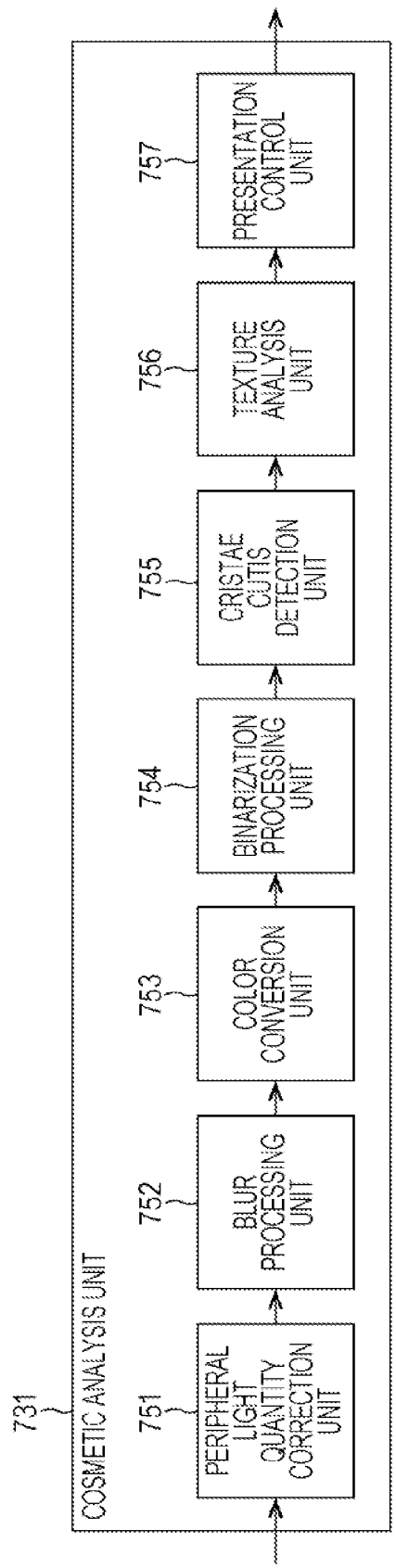
FIG. 34 is a block diagram showing an example structure of a cosmetic analysis unit.

FIG. 34 is a block diagram showing an example of functional structure of the cosmetic analysis unit 731. An example structure of the cosmetic analysis unit 731 that analyzes a person's skin texture is now described. The cosmetic analysis unit 731 is designed to include a peripheral light quantity correction unit 751, a blur processing unit 752, a color conversion unit 753, a binarization processing unit 754, a cristae cutis detection unit 755, a texture analysis unit 756, and a presentation control unit 757.

The peripheral light quantity correction unit 751 corrects the peripheral light quantity of a body-hair removed image, and supplies the corrected body-hair removed image to the blur processing unit 752.

The blur processing unit 752 performs a blurring process on the body-hair removed image, and supplies the body-hair removed image subjected to the blurring process, to the color conversion unit 753.

The color conversion unit 753 performs color conversion on the body-hair removed image, and supplies the body-hair removed image subjected to the color conversion, to the binarization processing unit 754.

The binarization processing unit 754 performs a binarization process on the body-hair removed image, and supplies the generated binarized image to the cristae cutis detection unit 755.

Based on the binarized image, the cristae cutis detection unit 755 detects the area of each of the cristae cutis in the skin image (the body-hair removed image), and generates a histogram showing the cristae cutis area distribution. The cristae cutis detection unit 755 supplies information indicating the generated histogram to the texture analysis unit 756.

The texture analysis unit 756 analyzes the skin texture based on the histogram showing the cristae cutis area distribution, and supplies the result of the analysis to the presentation control unit 757.

The presentation control unit 757 causes the display device 712 to display the result of the skin texture analysis.

[Cosmetic Analysis Process by Image Processing System 701]

Figure 35:
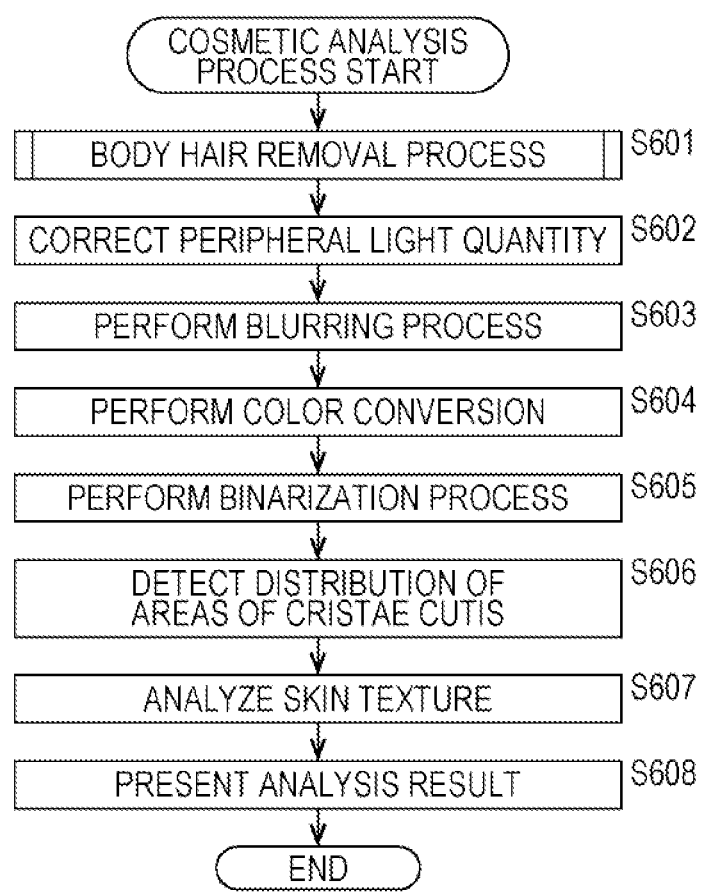
FIG. 35 is a flowchart for explaining a cosmetic analysis process.

Referring now to the flowchart shown in FIG. 35, a cosmetic analysis process to be performed by the image processing system 701 is described.

Figure 36:
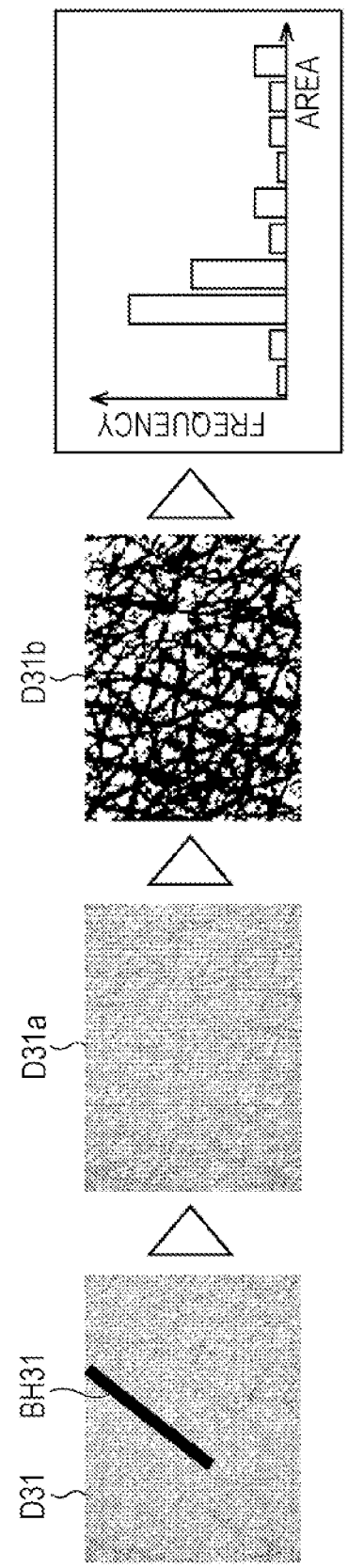
FIG. 36 is a diagram for explaining a specific example of the cosmetic analysis process.

In step S601, the body hair removal process described above with reference to FIG. 32 is performed. As a result, a body-hair removed image formed by removing a body hair from a skin image is generated, and the generated body-hair removed image is supplied from the body hair removal unit 431 to the peripheral light quantity correction unit 751 of the cosmetic analysis unit 731. For example, as shown in FIG. 36, an image D31a formed by removing a body hair BH31 from an image D31 showing the body hair BH31 is generated, and is supplied to the peripheral light quantity correction unit 751.

In step S602, the peripheral light quantity correction unit 751 corrects the peripheral light quantity of the body-hair removed image. The peripheral light quantity correction unit 751 supplies the corrected body-hair removed image to the blur processing unit 752.

In step S603, the blur processing unit 752 performs a blurring process on the body-hair removed image. The blur processing unit 752 supplies the body-hair removed image subjected to the blurring process, to the color conversion unit 753.

In step S604, the color conversion unit 753 performs color conversion. For example, the color conversion unit 753 converts the color space of the body-hair removed image into a predetermined color space such as an L*a*b* color system that separates luminance from chrominance, or an HSV space. The color conversion unit 753 supplies the body-hair removed image subjected to the color conversion, to the binarization processing unit 754.

In step S605, the binarization processing unit 754 performs a binarization process. For example, in a case where the color space of the body-hair removed image is converted into an L*a*b* color system or an HSV space, the binarization processing unit 754 converts the body-hair removed image into a black-and-white binarized image formed with pixels at two tone levels based on a predetermined threshold value. The pixels at the two tone levels are formed with pixels having luminosities equal to or higher than the threshold value and pixel having luminosities lower than the threshold value. The binarization processing unit 754 supplies the generated binarized image to the cristae cutis detection unit 755.

For example, as shown in FIG. 36, a binarized image D31b is generated from the image D31a by the processing in steps S602 through S605.

The skin image color conversion may not be performed, and the binarization process may be performed only with the use of one color (R, G, or B) in a RGB skin image.

In step S606, the cristae cutis detection unit 755 detects the distribution of the areas of cristae cutis. Specifically, the cristae cutis detection unit 755 recognizes the regions of white pixels surrounded by black pixels as the regions of cristae cutis surrounded by sulci cutis in the binarized image, and detects the areas of the respective cristae cutis. The cristae cutis detection unit 755 further generates a histogram showing the distribution of the detected areas of the cristae cutis. The cristae cutis detection unit 755 then supplies the information indicating the generated histogram to the texture analysis unit 756.

As a result, a histogram in which the abscissa axis indicates class based on the areas of the cristae cutis, and the ordinate axis indicates frequency, for example, is generated based on the binarized image D31b, as shown in FIG. 36.

In step S607, the texture analysis unit 756 analyzes the skin texture based on the distribution of the areas of the cristae cutis. For example, the texture analysis unit 756 determines whether the skin is a fine-textured skin based on deviation of the frequency in the histogram. In a case where there is large deviation of the frequency in the histogram to a certain class (area), for example, the texture analysis unit 756 determines that the skin is a fine-textured skin. Also, the texture analysis unit 756 analyzes the skin texture based on the class (area) in which the frequency in the histogram is higher, for example. In a case where the area of the class in which the highest frequency is small, for example, the texture analysis unit 756 determines that the skin is a fine-textured skin. The texture analysis unit 756 then supplies the result of the analysis to the presentation control unit 757.

In step S608, the display device 712 displays the result of the analysis. Specifically, the presentation control unit 757 generates the data for presenting the result of the skin texture analysis, and supplies the data to the display device 712. Based on the acquired data, the display device 712 displays an image showing the result of the skin texture analysis, to present the result of the analysis to the user.

The cosmetic analysis process then comes to an end.

FIG. 37 shows an example in a case where the body hair BH31 is not removed from the image D31, and the cosmetic analysis is then conducted. In this case, the body hair BH31 is not removed from a binarized image D31b' generated directly from the image D31. Therefore, the areas of cristae cutis are not accurately detected. More specifically, cristae cutis are further divided by the body hair BH31. As a result, cristae cutis having smaller areas than normal areas are detected, and a larger number of cristae cutis are detected. Therefore, in the histogram showing the distribution of the areas of cristae cutis, the frequency in the class corresponding to an area that does not normally exist becomes higher, and the frequency distribution becomes uneven. As a result, the precision of the skin texture analysis becomes lower.

On the contrary, the precision of the skin texture analysis is increased by conducting the cosmetic analysis with the use of an image formed by removing a body hair from a skin image as described above.

<8. Modifications>

The following is a description of modifications of the above described embodiments of the present technique.

[First Modification: Modification of a System Structure]

For example, the total sum of difference values of respective difference images, instead of difference images, may be stored, and, when a body hair region is detected, a difference image may be regenerated by using the homography matrix corresponding to the difference image with the smallest difference value. In this manner, the content in the storage unit 133 can be reduced.

Further, homography matrices may not be stored, for example. When a body hair region is detected, a homography matrix is recalculated based on the pairs of feature points used in the process of generating the difference image with the smallest difference value, and a difference image may be regenerated by using the recalculated homography matrix.

Also, in a case where a body hair is removed from a projection destination image, for example, the body hair can be removed not by projecting pixels from the projection original image on a pixel-by-pixel basis but by projecting pixels by the predetermined area unit with the use of a homography matrix. In this case, it is preferable to perform the projection after correcting distortion of images due to the difference in photographing direction.

In the above described example, a body hair is removed from a projection destination image by projecting pixels of the projection original image onto the projection destination image. Meanwhile, it is also possible to remove a body hair from the projection original image by calculating a homography matrix for projection from the projection destination image onto the coordinate system of the projection original image, and projecting the pixels outside the body hair region in the projection destination image onto the projection original image. That is, in the projection original image, the pixels outside the region corresponding to the body hair region of the projection destination image are replaced with the corresponding pixels of the projection destination image, so that a body-hair removed image formed by removing the body hair from the projection original image can be generated.

Alternatively, a body hair can be removed from the projection original image by projecting the pixels of the non-body-hair region of the projection destination image onto the projection original image. That is, in the projection original image, the pixels of the region (the body hair region of the projection original image) corresponding to the non-body-hair region of the projection destination image are replaced with the corresponding pixels (the pixels of the non-body-hair region) of the projection destination image, so that a body-hair removed image formed by removing the body hair from the projection original image can be generated.

For example, in a case where there is a photographing device that photographs the skin from directly above, like the above described photographing device 121-2 of FIG. 2 or 19, it is preferable to remove body hairs from a skin image captured by the photographing device so as to eventually obtain an image with smaller distortion.

Also, in the body hair region detection unit 132 of FIGS. 13 and 24, a body hair region can be detected with the use of skin images by an appropriate method that differs from the above described method. In this case, the homography matrix between images is calculated after a body hair region is detected, and a body hair is removed from a skin image by projecting pixels between the images with the use of the calculated homography matrix.

In a case where the positional relationship between the photographing device and the skin hardly changes when a probe is brought into close contact with the skin, the feature point extraction and the homography matrix calculation process may be skipped, and projective transform may be performed with the use of a homography matrix that has been calculated in advance.

In this case, it is assumed that the distance and the like between the photographing device and the skin change due to the force pressing the probe against the skin, and an error in the homography matrix occurs. To counter this, the force pressing the probe against the skin is measured with a pressure sensor or the like, and the probe may be controlled to maintain a fixed pressing force, or the user may be warned. Also, the influence of the error in the homography matrix may be reduced by performing the processing with lower skin image resolution.

In the above described example, difference images are generated by using combinations of four pairs of feature points, and a body hair region is then detected by using the difference image with the smallest difference value. In a case where priority is given to processing speed, for example, only one difference image may be generated by using one combination of four pairs of feature points, and a body hair region may be then detected. In a case where priority is given to detection precision, for example, the largest possible number of difference images may be generated by using all the combinations of four pairs of feature points, and a body hair region may be then detected by using the difference image with the smallest difference value.

Further, in the above described example, projective transform is performed by using a homography matrix. However, projective transform may be performed by using some other projection matrix or some other method. For example, projective transform can be performed by using a method that is developed by enhancing affine transform as described in JP 2009-258868 A.

[Second Modification: Example Application of Result of Body Hair Region Detection]

In the above described example, a body hair is removed from a skin image based on a result of body hair region detection. However, a result of body hair region detection can be used for other purposes.

For example, a body hair region masking image in which body hair regions are represented by 1, and the other skin regions are represented by 0 can be generated.

It is also possible to generate an image in which the body hair region in a skin image is shown in a different color from the rest.

Furthermore, it is possible to detect the amount of body hair based on a result of body hair region detection, for example. It is possible to calculate the degree of hairiness or the like based on the proportion of the area of the body hair region in a skin image, for example.

It is also possible to determine a hair type (damaged, dry, or the like) based on the shape, the length, the width, and the like of a detected body hair region, for example.

In the above described example, skin texture analysis is conducted as the cosmetic analysis process using a body-hair removed image. However, the cosmetic analysis object is not particularly limited, as long as analysis can be conducted with the use of a skin image. For example, with a body-hair removed image, it is possible to analyze the conditions (such as wrinkles) of the skin other than texture, the shade (redness, dullness, an amount of melanin, or the like) of the skin, and the like. The skin health (eczema, rash, or the like) can also be analyzed with the use of a body-hair removed image, for example.

[Third Modification: Modifications of Detection Object]

In the present technique, the detection object is not limited to a body hair. For example, in a case where at least part of the detection object is located in front of (or on the photographing device side of) the background, and the background regions hidden by the detection object differ from one another among images generated by photographing the detection object from different directions so that the backgrounds overlap at least partially, the region showing the detection object can be detected by the present technique. In the above described series of embodiments, the detection object is a body hair, and the background is the skin.

Figure 38:
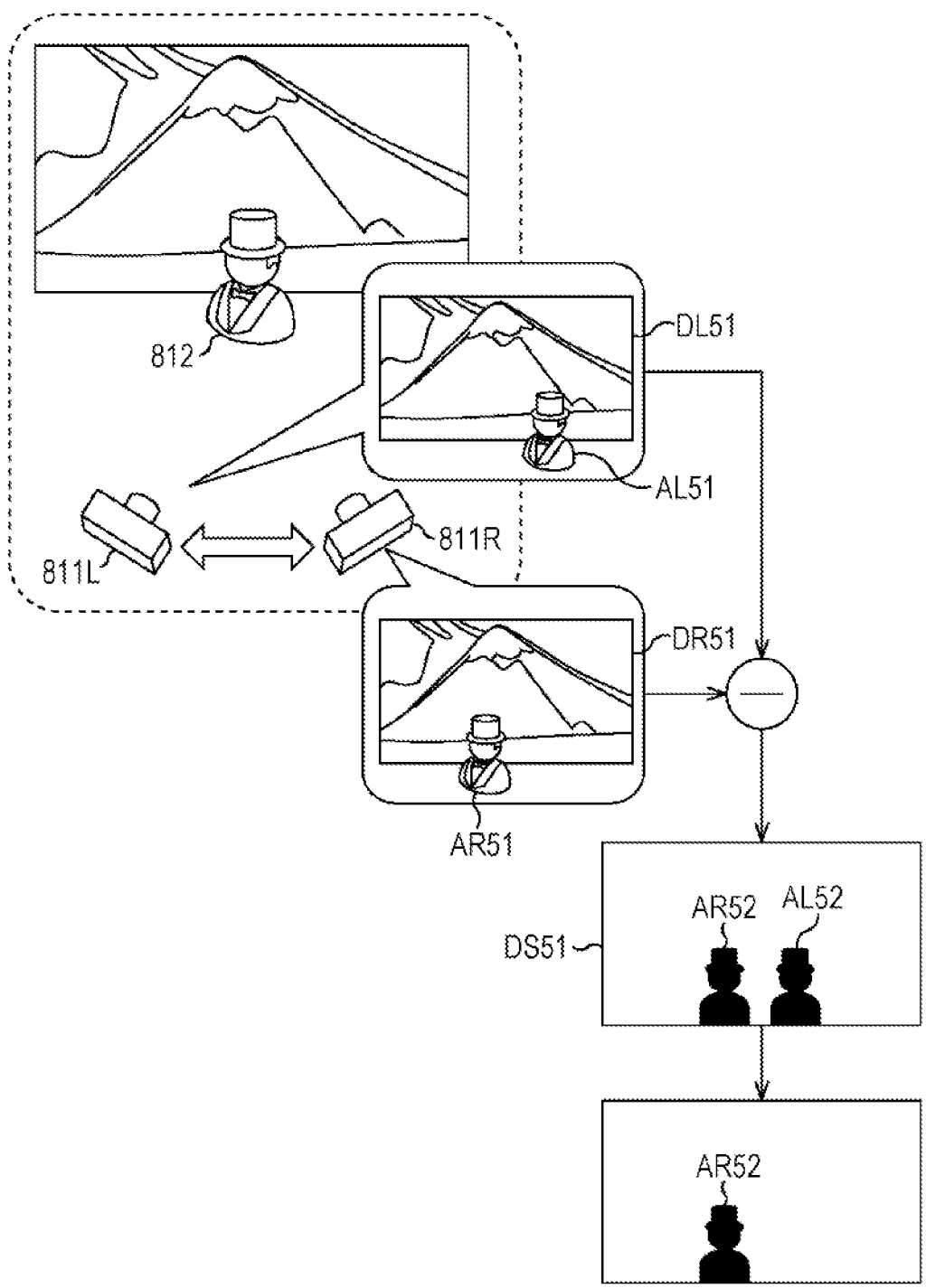
FIG. 38 is a diagram for explaining a modification of a detection object.

For example, the present technique can also be applied in a case where the detection object is a person 812, and the background is a landscape, as shown in FIG. 38. Specifically, the person 812 is photographed by a photographing device 811L and a photographing device 811R from different directions, so that at least some parts of the landscape overlap in the background. An image DL51 is an image captured by the photographing device 811L, and an image DR51 is an image captured by the photographing device 811R.

The image DL51 is set as the projection original image, the image DR51 is set as the projection destination image, and a difference image DS51 is generated by the above described process. In this difference image DS51, the difference values are large in a region AL52 corresponding to a region AL51 showing the person 812 in the image DL51, and in a region AR52 corresponding to a region AR51 showing the person 812 in the image DR51. Therefore, the region formed with the region AL52 and the region AR52 is detected as a candidate detection object region. The candidate detection object region is then divided into a region (hereinafter referred to as the detection object region) actually showing the person 812 in the DR51 as the projection destination image, and the other region (hereinafter referred to as the non-detection-object region).

In this case, the number of colors both in the person 812 as the detection object and in the landscape as the background is larger than that in a case where a body hair is detected. The candidate detection object region is detected as the two separate regions: the detection object region and the non-detection-object region. At this point, the detection object region and the non-detection-object region are separated by a different method from the method used in a case where a body hair is detected.

Figure 39:
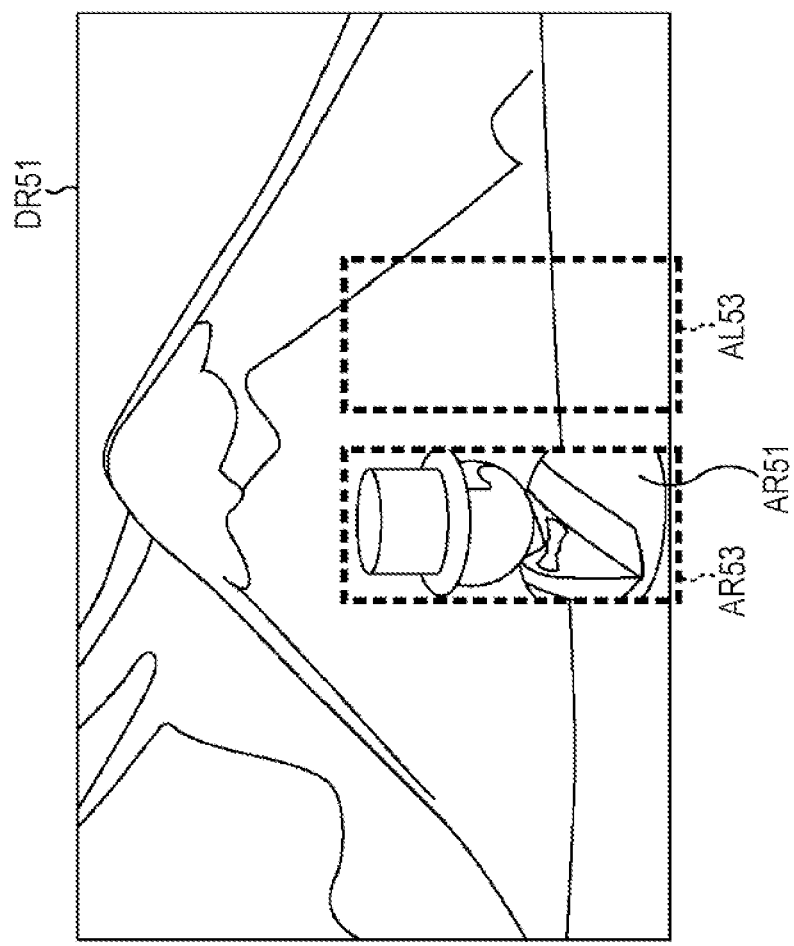
FIG. 39 is a diagram for explaining a method of detecting a detection object region in a case where the detection object is a person.

As shown in FIG. 39, in the image DR51 as the projection destination image, for example, the image in a region AR53 that corresponds to the region AR52 in the difference image DS51 and actually shows the person 812 greatly differs from the image in the surrounding region. In the image DR51, the image in a region AL53 corresponding to the region AL52 in the difference image DS51 is similar to the image in the surrounding region. The two regions are separated by using those features. In practice, the region AR53 and the region AL53 are regions having substantially the same shapes as the region AR51 and the AL51, respectively, but are simplified and shown as rectangular regions for ease of explanation.

Figure 40:
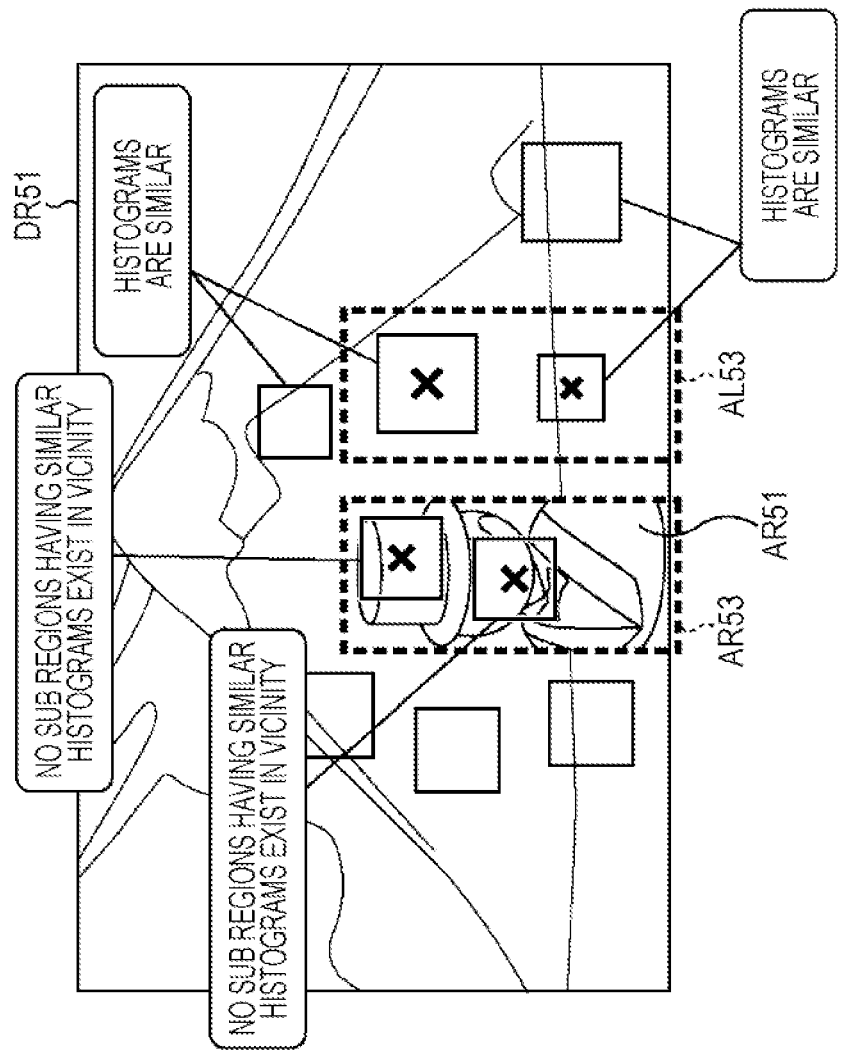
FIG. 40 is a diagram for explaining a method of detecting a detection object region in a case where the detection object is a person.

Specifically, as shown in FIG. 40, sub regions are set in the region AR53, the region AL53, and the region surrounding the two regions, and histograms showing the distributions of the feature quantities of the pixels in the respective sub regions are generated. As the feature quantities of the pixels, luminance, color signals, frequency information about the peripheral region, and the like can be used, for example. One of those feature quantities may be used independently, or a combination of some of the feature quantities may be used.

The shapes and the areas of the respective sub regions can be arbitrarily set. For example, each of the sub regions may have a rectangular shape or an elliptical shape, and the sub regions may have different areas from one another. In a case where the respective sub regions have different areas, the histogram of each of the sub regions is normalized so that the frequency sum becomes invariably 1. The respective sub regions may have overlapping portions. However, the sub regions around the candidate detection object region do not overlap the candidate detection object region, and are preferably located as close to the candidate detection object region as possible.

The degree of similarity in histogram between the sub regions in the candidate detection object region and the sub regions around the candidate detection object region is then calculated. The histogram similarity index indicating the degree of similarity in histogram may be the Bhattacharyya coefficient, the Cos similarity, the Pearson's correlation coefficient, an intervector distance (such as the Euclidean distance), or the like. One of those indexes may be used independently, or a combination of some of the indexes may be used.

A check is then made to determine whether the histograms are similar based on the histogram similarity index and a predetermined threshold value. Of the two regions constituting the candidate detection object region, the region having the larger number of sub regions that are similar in histogram to the sub regions in the surrounding region is set as the non-detection-object region, and the other region is set as the detection object region. In the example shown in FIG. 40, the region AL53 is set as the non-detection-object region, and the region AR53 is set as the detection object region.

In this case, the area of the person 812 as the detection object is large, and the distances from the photographing devices 811L and 811R to the person 812 are long. Therefore, the distance between the photographing device 811L and the photographing device 811R needs to be sufficiently long, so as to prevent the background region hidden by the region AL51 in the image DL51 from overlapping the background region hidden by the region AR51 in the image DR51, and prevent the region AR52 in the difference image DS51 from overlapping the region AR52.

In a case where it is difficult to set the photographing device 811L and the photographing device 811R at the necessary distance from each other, a photographer may move between two spots located at a distance from each other while taking photographs. This is particularly effective in a case where the detection object is a still object such as an architectural structure.

Also, images taken by some photographers photographing the detection object from respective spots may be used. In this case, the images taken from the respective spots can be shared by using a network service such as an SNS (Social Networking Service) or a cloud service.

In a case where the respective images vary in image quality due to different photographing conditions such as the dates and weather at the respective spots, the process of detecting the detection object is preferably performed after the respective images are corrected to achieve uniform image quality.

Depending on the detection object, the detection object is not removed but remains, and the background is removed in some application.

In a case where the detection object is a body hair, a sample image showing the body hair can be generated. For example, images are formed by extracting only body hairs from skin images of respective body sites, so that comparisons can be made among an arm hair, a leg hair, a head hair, and the like.

Figure 41:
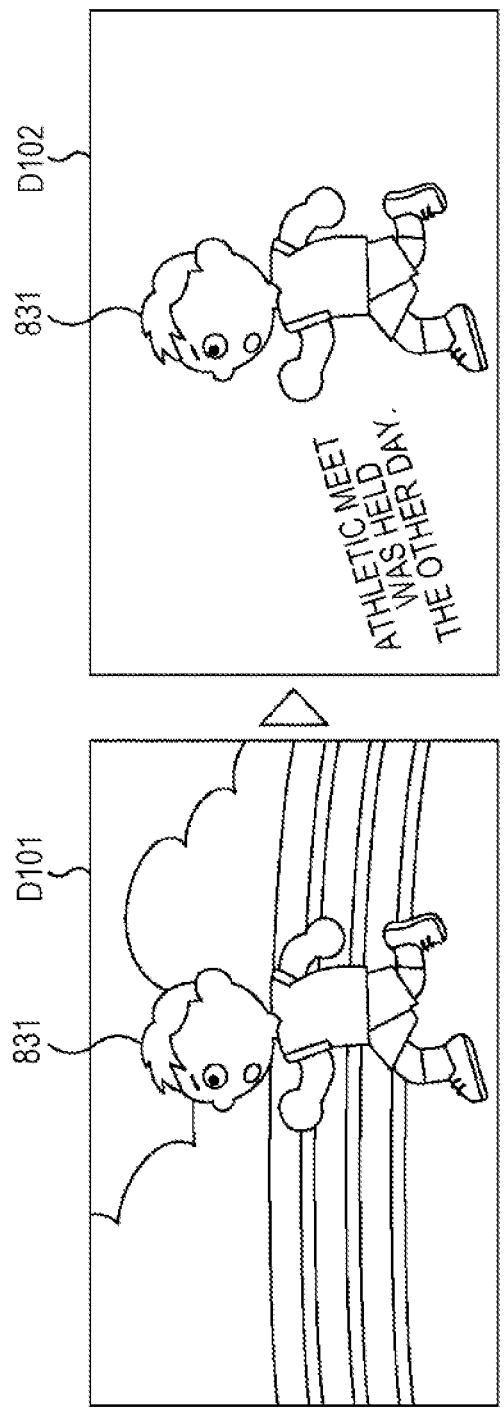
FIG. 41 is a diagram for explaining a first example application of the present technique.
Figure 42:
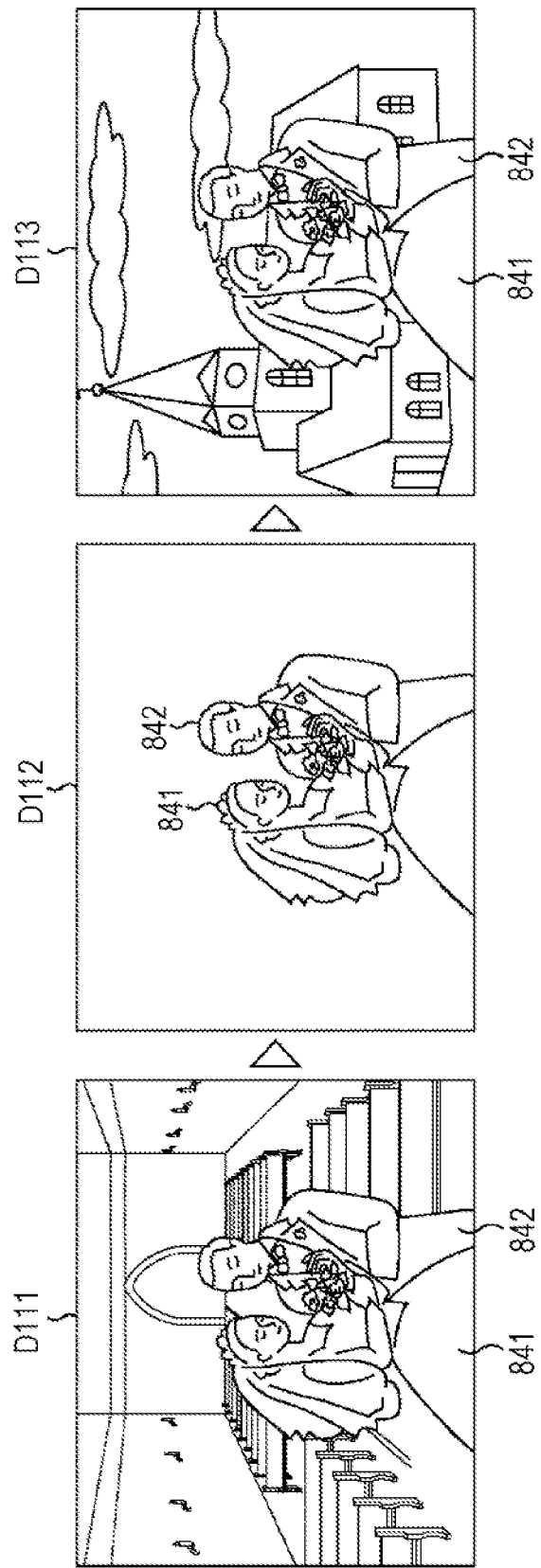
FIG. 42 is a diagram for explaining a second example application of the present technique.

Also, as shown in FIG. 41, after a person 831 as the detection object is detected from an image D101, the background other than the person 831 is removed from the image D101, and text or the like is added so as to create a picture postcard D102 in some application.

Further, in some application, persons 841 and 842 as detection objects are detected from an image D111, and an image D112 formed by removing the background other than the persons 841 and 842 from the image D111 is generated. Another background is then added to the image D112, to create an image D113. [Configuration Example of Computer]

The above described series of processes can be performed by hardware, and can also be performed by software. When the series of processes described above is performed by software, the programs forming the software are installed in a computer. Here, the computer may be a computer incorporated into special-purpose hardware, or may be a general-purpose personal computer that can execute various kinds of functions as various kinds of programs are installed thereinto.

Figure 43:
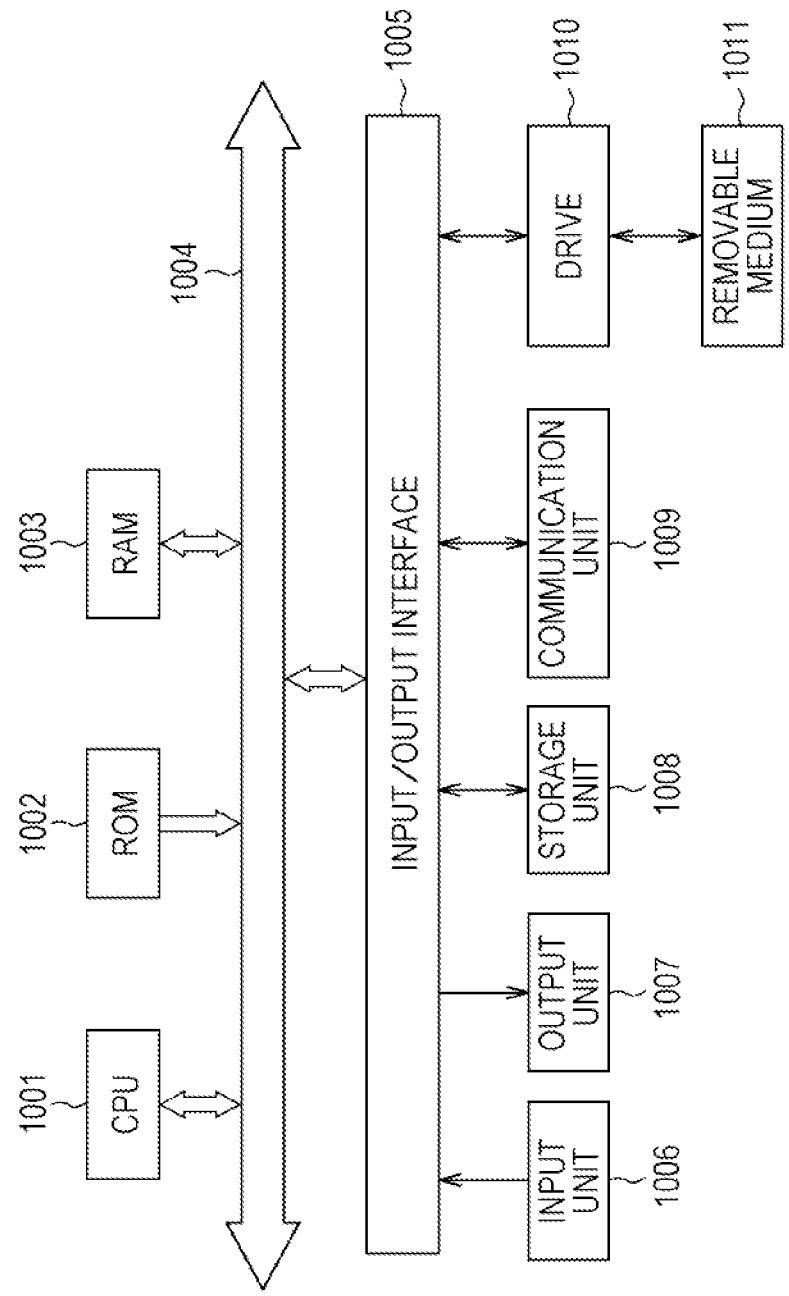
FIG. 43 is a block diagram showing an example structure of a computer.

FIG. 43 is a block diagram showing an example of configuration of the hardware of a computer that performs the above described series of processes in accordance with a program.

In the computer, a CPU (Central Processing Unit) 1001, a ROM (Read Only Memory) 1002, and a RAM (Random Access Memory) 1003 are connected to one another by a bus 1004.

An input/output interface 1005 is further connected to the bus 1004. An input unit 1006, an output unit 1007, a storage unit 1008, a communication unit 1009, and a drive 1010 are connected to the input/output interface 1005.

The input unit 1006 is formed with a keyboard, a mouse, a microphone, and the like. The output unit 1007 is formed with a display, a speaker, and the like. The storage unit 1008 is formed with a hard disk, a nonvolatile memory, or the like. The communication unit 1009 is formed with a network interface or the like. The drive 1010 drives a removable medium 1011 such as a magnetic disk, an optical disk, a magnetooptical disk, or a semiconductor memory.

In the computer having the above described structure, the CPU 1001 loads the programs stored in the storage unit 1008 into the RAM 1003 via the input/output interface 1005 and the bus 1004, and executes the programs, so that the above described series of processes are performed.

The programs to be executed by the computer (the CPU 1001) may be recorded on the removable medium 1011 as a package medium to be provided, for example. Alternatively, the programs can be provided via a wired or wireless transmission medium such as a local area network, the Internet, or the digital satellite broadcasting.

In the computer, the programs can be installed into the storage unit 1008 via the input/output interface 1005 when the removable medium 1011 is mounted on the drive 1010. Also, the programs may be received by the communication unit 1009 via a wired or wireless transmission medium, and be installed into the storage unit 1008. Alternatively, the programs may be installed beforehand into the ROM 1002 or the storage unit 1008.

The programs to be executed by the computer may be programs for carrying out processes in chronological order in accordance with the sequence described in this specification, or programs for carrying out processes in parallel or whenever necessary such as in response to a call.

In this specification, a system means an assembly of a plurality of components (apparatuses, modules (parts), and the like), and not all the components need to be provided in the same housing. In view of this, apparatuses that are housed in different housings and are connected to each other via a network form a system, and one apparatus having modules housed in one housing is also a system.

Further, it should be noted that embodiments of the present technique are not limited to the above described embodiments, and various modifications may be made to them without departing from the scope of the present technique.

For example, the present technique can be embodied in a cloud computing structure in which one function is shared among apparatuses via a network, and processing is performed by the apparatuses cooperating with one another.

The respective steps described with reference to the above described flowcharts can be carried out by one apparatus or can be shared among apparatuses.

In a case where more than one process is included in one step, the processes included in the one step can be performed by one apparatus or can be shared among apparatuses.

The present technique can also be in the following forms, for example.

(1) An image processing device including
a detection object region detection unit that detects a region showing a detection object in an image generated by photographing the detection object,
wherein the detection object region detection unit includes:
a projective transform unit that generates a projected image by projectively transforming a first image generated by photographing the detection object into the coordinate system of a second image generated by photographing the detection object from a different direction from the first image;
a difference image generation unit that generates a difference image between the second image and the projected image; and
a region detection unit that detects a candidate region formed with pixels having difference values equal to or larger than a predetermined threshold value in the difference image, and divides the region corresponding to the candidate region in the second image into a detection object region showing the detection object and a non-detection-object region outside the detection object region.

(2) The image processing device of (1), further including
a detection object removal unit that removes the detection object from an image generated by photographing the detection object,
wherein the detection object removal unit includes:
the detection object region detection unit; and
a removal unit that removes the detection object from one of the first image and the second image by projecting at least pixels in a region corresponding to a region showing the detection object in the one of the first image and the second image onto pixels in the one of the images to replace the corresponding pixels based on a result of the detection performed by the detection object region detection unit, the pixels projected being in the other one of the first image and the second image.

(3) The image processing device of (2), wherein the removal unit removes the detection object from the second image by projecting at least pixels in a region in the first image corresponding to the detection object region in the second image onto the second image, and replacing the corresponding pixels.

(4) The image processing device of (2), wherein the removal unit removes the detection object from the first image by projecting at least pixels in the non-detection-object region in the second image onto the first image, and replacing the corresponding pixels.

(5) The image processing device of any of (2) through (4), wherein the detection object removal unit selects two images from three or more images generated by photographing the detection object from different directions from one another, newly generates an image having the detection object removed therefrom by using the selected two images, and repeats the process of newly generating an image having the detection object removed therefrom by using the newly generated image and one of the remaining images until there are no remaining images.

(6) The image processing device of any of (1) through (5), wherein
the detection object region detection unit further includes:
a feature point extraction unit that extracts a feature point of the first image and a feature point of the second image;
an association unit that associates the feature point of the first image with the feature point of the second image; and
a projection matrix calculation unit that calculates a projection matrix generated by projecting the first image onto the coordinate system of the second image based on at least part of the pair of the feature point of the first image and the feature point of the second image associated with each other by the association unit, and
the projective transform unit generates the projected image by using the projection matrix.

(7) The image processing device of (6), wherein
the projection matrix calculation unit calculates a plurality of the projection matrices based on a combination of a plurality of pairs of the feature points,
the projective transform unit generates a plurality of the projected images by using the respective projection matrices,
the difference image generation unit generates a plurality of the difference images between the second image and the respective projected images, and
the region detection unit detects the candidate region by using the difference image having the smallest difference from the second image among the difference images.

(8) The image processing device of any of (1) through (7), wherein the region detection unit separates the detection object region from the non-detection-object region by comparing an image in the region of the second image corresponding to the candidate region with surrounding images.

(9) The image processing device of any of (1) through (8), wherein
the detection object region detection unit detects the detection object region in each of three or more images generated by photographing the detection object from different directions from one another, and
the image processing device further includes a region combination unit that combines the detection object region in an image selected from the three or more images with a region generated by projecting the detection object regions of the remaining images onto the coordinate system of the selected image.

(10) An image processing method, wherein an image processing device performs the step of:
generating a projected image by projectively transforming a first image generated by photographing a detection object into the coordinate system of a second image generated by photographing the detection object from a different direction from the first image;
generating a difference image between the second image and the projected image;
detecting a candidate region formed with pixels having difference values equal to or larger than a predetermined threshold value in the difference image; and
dividing the region corresponding to the candidate region in the second image into a detection object region showing the detection object and a non-detection-object region outside the detection object region.

(11) A program for causing a computer to perform a process including the steps of:

generating a projected image by projectively transforming a first image generated by photographing a detection object into the coordinate system of a second image generated by photographing the detection object from a different direction from the first image;

generating a difference image between the second image and the projected image;

detecting a candidate region formed with pixels having difference values equal to or larger than a predetermined threshold value in the difference image; and dividing the region corresponding to the candidate region in the second image into a detection object region showing the detection object and a non-detection-object region outside the detection object region.

(12) An image processing system including:

a photographing unit that photographs a detection object; and a detection object region detection unit that detects a region showing the detection object in an image captured by the photographing unit, wherein the detection object region detection unit includes:

a projective transform unit that generates a projected image by projectively transforming a first image generated by photographing the detection object with the photographing unit into the coordinate system of a second image generated by photographing the detection object with the photographing unit from a different direction from the first image;

a difference image generation unit that generates a difference image between the second image and the projected image; and a region detection unit that detects a candidate region formed with pixels having difference values equal to or larger than a predetermined threshold value in the difference image, and divides the region corresponding to the candidate region in the second image into a detection object region showing the detection object and a non-detection-object region outside the detection object region.

(13) The image processing system of (12), further including a detection object removal unit that removes the detection object from an image generated by photographing the detection object with the photographing unit, wherein the detection object removal unit includes:

the detection object region detection unit; and a removal unit that removes the detection object from one of the first image and the second image by projecting at least pixels in a region corresponding to a region showing the detection object in the one of the first image and the second image onto pixels in the one of the images to replace the corresponding pixels based on a result of the detection performed by the detection object region detection unit, the pixels projected being in the other one of the first image and the second image.

(14) The image processing system of (13), wherein the detection object removal unit selects two images from three or more images generated by photographing the detection object with the photographing unit from different directions from one another, newly generates an image having the detection object removed therefrom by using the selected two images, and repeats the process of newly generating an image having the detection object removed therefrom by using the newly generated image and one of the remaining images until there are no remaining images.

(15) The image processing system of any of (12) through (14), wherein the detection object region detection unit further includes:

a feature point extraction unit that extracts a feature point of the first image and a feature point of the second image;

an association unit that associates the feature point of the first image with the feature point of the second image; and a projection matrix calculation unit that calculates a projection matrix generated by projecting the first image onto the coordinate system of the second image based on at least part of the pair of the feature point of the first image and the feature point of the second image associated with each other by the association unit, and the projective transform unit generates the projected image by using the projection matrix.

(16) The image processing system of any of (12) through (15), wherein the detection object region detection unit detects the detection object region in each of three or more images generated by photographing the detection object with the photographing unit from different directions from one another, and the image processing system further includes a region combination unit that combines the detection object region in an image selected from the three or more images with a region generated by projecting the detection object regions of the remaining images onto the coordinate system of the selected image.

(17) The image processing system of any of (12) through (16), wherein the photographing unit includes:

a plurality of lenses two-dimensionally arrayed; and a plurality of imaging elements, the imaging elements is provided for each one of the lenses, with positions of the imaging elements relative to the respective lenses being the same, and the image processing system further includes an image generation unit that generates a plurality of images captured by the imaging elements having the same positions relative to the lenses.

(18) The image processing system of any of (12) through (16), wherein the photographing unit captures an image reflected in a mirror that radially surrounds at least part of a region including the detecting object, and the image processing system further includes:

an image cutout unit that cuts out a plurality of images from the image generated by the photographing unit capturing the image reflected in the mirror; and a geometric distortion correction unit that performs geometric distortion correction on the cut-out images.

(19) The image processing system of any of (12) through (18), wherein the first image and the second image are images captured by the photographing unit taking a closeup image of the detection object.

(20) An image processing device including:

a projective transform unit that generates a projected image by projectively transforming a first image generated by photographing a body hair into the coordinate system of a second image generated by photographing the body hair from a different direction from the first image;

a difference image generation unit that generates a difference image between the second image and the projected image;

a region detection unit that detects a candidate region formed with pixels having difference values equal to or larger than a predetermined threshold value in the difference image, and divides the region corresponding to the candidate region in the second image into a body hair region showing the body hair and a non-body-hair region outside the body hair region; and a removal unit that removes the body hair from one of the first image and the second image by projecting at least the pixels in the region corresponding to the region showing the body hair in the one of the first image and the second image onto pixels in the one of the images to replace the corresponding pixel based on a result of the detection performed by the region detection unit, the pixels projected being in the other one of the first image and the second image.

REFERENCE SIGNS LIST

101 Image processing system
111 Probe
112 Image processing device
121-1 to 121-n Photographing devices
131 Image acquisition unit
132 Body hair region detection unit
151 Feature point extraction unit
152 Association unit
153 Homography matrix calculation unit
154 Projective transform unit
155 Difference image generation unit
156 Region detection unit
201 Image processing system
231 Body hair removal unit
241 Removal unit
301 Image processing system
311 Probe
312 Image processing device
331 Image acquisition unit
332 Image selection unit
333 Region detection unit
401 Image processing system
411 Image processing device
431 Body hair removal unit
441 Image selection unit
442 Removal unit
501 Image processing system
511 Probe
512 Image processing device
521 Photographing device
522 Mirror
531 Image acquisition unit
532 Image cutout unit
533 Geometric distortion correction unit
601 Image processing system
611 Probe
612 Image processing device
621 Photographing device
631 Image acquisition unit
632 Image reconstruction unit
651A to 651D Microlens
652A to 652D, 653A to 653D Imaging elements
701 Image processing system
711 Image processing device
731 Cosmetic analysis unit

The invention claimed is:

1. An image processing device comprising
a detection object region detection unit configured to detect a region showing a detection object in an image generated by photographing the detection object,
wherein the detection object region detection unit includes:
a projective transform unit configured to generate a projected image by projectively transforming a first image generated by photographing the detection object into a coordinate system of a second image generated by photographing the detection object from a different direction from the first image;
a difference image generation unit configured to generate a difference image between the second image and the projected image; and
a region detection unit configured to detect a candidate region formed with a pixel having a difference value equal to or larger than a predetermined threshold value in the difference image, and divide a region corresponding to the candidate region in the second image into a detection object region showing the detection object and a non-detection-object region outside the detection object region,
in which the detection object is a body hair of a person such that the detection object region detection unit is configured to detect the region in the image which shows the body hair.

2. An image processing device comprising:
a detection object region detection unit configured to detect a region showing a detection object in an image generated by photographing the detection object,
wherein the detection object region detection unit includes:
a projective transform unit configured to generate a projected image by projectively transforming a first image generated by photographing the detection object into a coordinate system of a second image generated by photographing the detection object from a different direction from the first image;
a difference image generation unit configured to generate a difference image between the second image and the projected image; and
a region detection unit configured to detect a candidate region formed with a pixel having a difference value equal to or larger than a predetermined threshold value in the difference image, and divide a region corresponding to the candidate region in the second image into a detection object region showing the detection object and a non-detection-object region outside the detection object region,
further comprising a detection object removal unit configured to remove the detection object from an image generated by photographing the detection object,
wherein the detection object removal unit includes:
the detection object region detection unit; and
a removal unit configured to remove the detection object from one of the first image and the second image by projecting at least pixels in a region corresponding to a region showing the detection object in the one of the first image and the second image onto pixels in the one of the images to replace the corresponding pixels based on a result of the detection performed by the detection object region detection unit, the pixels projected being in the other one of the first image and the second image.

3. The image processing device according to claim 2, wherein the removal unit removes the detection object from the second image by projecting at least pixels in a region in the first image corresponding to the detection object region in the second image onto the second image, and replacing the corresponding pixels.

4. The image processing device according to claim 2, wherein the removal unit removes the detection object from the first image by projecting at least pixels in the non-detection-object region in the second image onto the first image, and replacing the corresponding pixels.

5. The image processing device according to claim 2, wherein the detection object removal unit selects two images from three or more images generated by photographing the detection object from different directions from one another, newly generates an image having the detection object removed therefrom by using the selected two images, and repeats the process of newly generating an image having the detection object removed therefrom by using the newly generated image and one of the remaining images until there are no remaining images.

6. The image processing device according to claim 1, wherein the detection object region detection unit further includes:
  a feature point extraction unit configured to extract a feature point of the first image and a feature point of the second image;
  an association unit configured to associate the feature point of the first image with the feature point of the second image; and
  a projection matrix calculation unit configured to calculate a projection matrix generated by projecting the first image onto the coordinate system of the second image based on at least part of the pair of the feature point of the first image and the feature point of the second image associated with each other by the association unit, and
  the projective transform unit generates the projected image by using the projection matrix.

7. An image processing device comprising:
  a detection object region detection unit configured to detect a region showing a detection object in an image generated by photographing the detection object,
  wherein the detection object region detection unit includes:
    a projective transform unit configured to generate a projected image by projectively transforming a first image generated by photographing the detection object into a coordinate system of a second image generated by photographing the detection object from a different direction from the first image;
    a difference image generation unit configured to generate a difference image between the second image and the projected image;
    a region detection unit configured to detect a candidate region formed with a pixel having a difference value equal to or larger than a predetermined threshold value in the difference image, and divide a region corresponding to the candidate region in the second image into a detection object region showing the detection object and a non-detection-object region outside the detection object region;
    a feature point extraction unit configured to extract a feature point of the first image and a feature point of the second image; and
    a projection matrix calculation unit configured to calculate a projection matrix generated by projecting the first image onto the coordinate system of the second image based on at least part of the pair of the feature point of the first image and the feature point of the second image associated with each other by the association unit,
  the projective transform unit generates the projected image by using the projection matrix,
  the projection matrix calculation unit calculates a plurality of projection matrices based on a combination of a plurality of pairs of the feature points,
  the projective transform unit generates a plurality of the projected images by using the respective projection matrices,
  the difference image generation unit generates a plurality of the difference images 5 between the second image and the respective projected images, and
  the region detection unit detects the candidate region by using the difference image having the smallest difference from the second image among the difference images.

8. The image processing device according to claim 1, wherein the region detection unit separates the detection object region from the non-detection-object region by comparing an image in a region of the second image corresponding to the candidate region with surrounding images.

9. An image processing device comprising
  a detection object region detection unit configured to detect a region showing a detection object in an image generated by photographing the detection object,
  wherein the detection object region detection unit includes:
    a projective transform unit configured to generate a projected image by projectively transforming a first image generated by photographing the detection object into a coordinate system of a second image generated by photographing the detection object from a different direction from the first image;
    a difference image generation unit configured to generate a difference image between the second image and the projected image; and
    a region detection unit configured to detect a candidate region formed with a pixel having a difference value equal to or larger than a predetermined threshold value in the difference image, and divide a region corresponding to the candidate region in the second image into a detection object region showing the detection object and a non-detection-object region outside the detection object region,
  wherein
  the detection object region detection unit detects the detection object region in each of three or more images generated by photographing the detection object from different directions from one another, and
  the image processing device further includes a region combination unit configured to combine the detection object region in an image selected from the three or more images with a region generated by projecting the detection object regions of the remaining images onto a coordinate system of the selected image.

10. An image processing method, wherein an image processing device performs the steps of:
  generating a projected image by projectively transforming a first image generated by photographing a detection object into a coordinate system of a second image generated by photographing the detection object from a different direction from the first image;
  generating a difference image between the second image and the projected image;
  detecting a candidate region formed with a pixel having a difference value equal to or larger than a predetermined threshold value in the difference image; and
  dividing the region corresponding to the candidate region in the second image into a detection object region showing the detection object and a non-detection-object region outside the detection object region,
  in which the detection object is a body hair of a person.

11. A non-transitory computer readable medium having stored thereon a program for causing a computer to perform a process including the steps of:
   generating a projected image by projectively transforming a first image generated by photographing a detection object into a coordinate system of a second image generated by photographing the detection object from a different direction from the first image;
   generating a difference image between the second image and the projected image;
   detecting a candidate region formed with a pixel having a difference value equal to or larger than a predetermined threshold value in the difference image; and
   dividing the region corresponding to the candidate region in the second image into a detection object region showing the detection object and a non-detection-object region outside the detection object region,
in which the detection object is a body hair of a person.

12. An image processing system comprising:
   a photographing unit configured to photograph a detection object; and
   a detection object region detection unit configured to detect a detection object region showing the detection object in an image captured by the photographing unit,
   wherein the detection object region detection unit includes:
      a projective transform unit configured to generate a projected image by projectively transforming a first image generated by photographing the detection object with the photographing unit into a coordinate system of a second image generated by photographing the detection object with the photographing unit from a different direction from the first image;
      a difference image generation unit configured to generate a difference image between the second image and the projected image; and
      a region detection unit configured to detect a candidate region formed with a pixel having a difference value equal to or larger than a predetermined threshold value in the difference image, and divides a region corresponding to the candidate region in the second image into a detection object region showing the detection object and a non-detection-object region outside the detection object region,
   in which the detection object is a body hair of a person such that the detection object region detection unit is configured to detect the region in the image which shows the body hair.

13. An image processing system comprising:
   a photographing unit configured to photograph a detection object;
   a detection object region detection unit configured to detect a detection object region showing the detection object in an image captured by the photographing unit,
   wherein the detection object region detection unit includes:
      a projective transform unit configured to generate a projected image by projectively transforming a first image generated by photographing the detection object with the photographing unit into a coordinate system of a second image generated by photographing the detection object with the photographing unit from a different direction from the first image;
      a difference image generation unit configured to generate a difference image between the second image and the projected image; and
      a region detection unit configured to detect a candidate region formed with a pixel having a difference value equal to or larger than a predetermined threshold value in the difference image, and divides a region corresponding to the candidate region in the second image into a detection object region showing the detection object and a non-detection-object region outside the detection object region; and
   further comprising a detection object removal unit configured to remove the detection object from an image generated by photographing the detection object with the photographing unit,
   wherein the detection object removal unit includes:
      the detection object region detection unit; and
      a removal unit configured to remove the detection object from one of the first image and the second image by projecting at least pixels in a region corresponding to a region showing the detection object in the one of the first image and the second image onto pixels in the one of the images to replace the corresponding pixels based on a result of the detection performed by the detection object region detection unit, the pixels projected being in the other one of the first image and the second image.

14. The image processing system according to claim 13, wherein the detection object removal unit selects two images from three or more images generated by photographing the detection object with the photographing unit from different directions from one another, newly generates an image having the detection object removed therefrom by using the selected two images, and repeats the process of newly generating an image having the detection object removed therefrom by using the newly generated image and one of the remaining images until there are no remaining images.

15. The image processing system according to claim 12, wherein
   the detection object region detection unit further includes:
      a feature point extraction unit configured to extract a feature point of the first image and a feature point of the second image;
      an association unit configured to associate the feature point of the first image with the feature point of the second image; and
      a projection matrix calculation unit configured to calculate a projection matrix generated by projecting the first image onto the coordinate system of the second image based on at least part of the pair of the feature point of the first image and the feature point of the second image associated with each other by the association unit, and
   the projective transform unit generates the projected image by using the projection matrix.

16. An image processing system comprising:
   a photographing unit configured to photograph a detection object; and
   a detection object region detection unit configured to detect a detection object region showing the detection object in an image captured by the photographing unit,
   wherein the detection object region detection unit includes:
      a projective transform unit configured to generate a projected image by projectively transforming a first image generated by photographing the detection object with the photographing unit into a coordinate system of a second image generated by photographing the detection object with the photographing unit from a different direction from the first image;
      a difference image generation unit configured to generate a difference image between the second image and the projected image; and
      a region detection unit configured to detect a candidate region formed with a pixel having a difference value equal to or larger than a predetermined threshold value in the difference image, and divides a region corresponding to the candidate region in the second image into a detection object region showing the detection object and a non-detection-object region outside the detection object region, wherein the detection object region detection unit detects the detection object region in each of three or more images generated by photographing the detection object with the photographing unit from different directions from one another, and the image processing system further includes a region combination unit configured to combine the detection object region in an image selected from the three or more images with a region generated by projecting the detection object regions of the remaining images onto a coordinate system of the selected image.

17. The image processing system according to claim 12, wherein the photographing unit includes:

a plurality of lenses two-dimensionally arranged; and a plurality of imaging elements, the plurality of the imaging elements is provided for each one of the lenses, with positions of the imaging elements relative to the respective lenses being the same, and the image processing system further comprises an image generation unit configured to generate a plurality of images captured by the imaging elements having the same positions relative to the lenses.

18. An image processing system comprising:

a photographing unit configured to photograph a detection object; and a detection object region detection unit configured to detect a detection object region showing the detection object in an image captured by the photographing unit, wherein the detection object region detection unit includes:

a projective transform unit configured to generate a projected image by projectively transforming a first image generated by photographing the detection object with the photographing unit into a coordinate system of a second image generated by photographing the detection object with the photographing unit from a different direction from the first image;

a difference image generation unit configured to generate a difference image between the second image and the projected image; and a region detection unit configured to detect a candidate region formed with a pixel having a difference value equal to or larger than a predetermined threshold value in the difference image, and divides a region corresponding to the candidate region in the second image into a detection object region showing the detection object and a non-detection-object region outside the detection object region, wherein the photographing unit captures an image reflected in a minor that radially surrounds at least part of a region including the detecting object, and the image processing system further comprises:

an image cutout unit configured to cut out a plurality of images from the image generated by the photographing unit capturing the image reflected in the minor; and a geometric distortion correction unit configured to perform geometric distortion correction on the cut-out images.

19. The image processing system according to claim 12, wherein the first image and the second image are images captured by the photographing unit taking a closeup image of a region including the detection object.

20. An image processing device comprising:

a projective transform unit configured to generate a projected image by projectively transforming a first image generated by photographing a body hair into a coordinate system of a second image generated by photographing the body hair from a different direction from the first image;

a difference image generation unit configured to generate a difference image between the second image and the projected image;

a region detection unit configured to detect a candidate region formed with a pixel having a difference value equal to or larger than a predetermined threshold value in the difference image, and divide a region corresponding to the candidate region in the second image into a body hair region showing the body hair and a nonbody-hair region outside the body hair region; and a removal unit configured to remove the body hair from one of the first image and the second image by projecting at least pixels in a region corresponding to a region showing the body hair in the one of the first image and the second image onto pixels in the one of the images to replace the corresponding pixel based on a result of the detection performed by the region detection unit, the pixels projected being in the other one of the first and the second image.

* * * * *